(12) United States Patent
Avner et al.

(10) Patent No.: US 7,960,107 B2
(45) Date of Patent: Jun. 14, 2011

(54) METHOD OF DETERMINING THE SUSCEPTIBILITY OF A SUBJECT TO DEVELOPING INSULIN-DEPENDENT DIABETES

(75) Inventors: Philip Avner, Paris (FR); Ute Christine Rogner, Paris (FR); Ming-Shiu Hung, Taoyuan (TW)

(73) Assignee: Institut Pasteur, Paris (FR)

( * ) Notice: Subject to any disclaimer, the term of this patent is extended or adjusted under 35 U.S.C. 154(b) by 903 days.

(21) Appl. No.: 11/679,492

(22) Filed: Feb. 27, 2007

(65) Prior Publication Data

US 2007/0214510 A1  Sep. 13, 2007

Related U.S. Application Data

(60) Provisional application No. 60/776,662, filed on Feb. 27, 2006.

(51) Int. Cl.
  *C12Q 1/68* (2006.01)
  *G01N 33/53* (2006.01)
  *C07H 21/04* (2006.01)
  *C07K 14/435* (2006.01)

(52) U.S. Cl. ............. 435/6; 435/7.1; 536/23.5; 530/350

(58) Field of Classification Search ........................ None
  See application file for complete search history.

(56) References Cited

U.S. PATENT DOCUMENTS

2009/0181915 A1  7/2009  Avner et al.

FOREIGN PATENT DOCUMENTS

WO   WO 2006019824 A2 *  2/2006

OTHER PUBLICATIONS

Gunton, J.E. et al. Cell 122:337-349 (Aug. 2005).*
Rudic, R.D. et al. Methods in Enzymology 393:524-539 (Apr. 2005).*
Hung, M-S et al. Human Molecular Genetics 15(18):2732-2742 (Aug. 2006).*

* cited by examiner

*Primary Examiner* — Diana B Johannsen
(74) *Attorney, Agent, or Firm* — Oblon, Spivak, McClelland, Maier & Neustadt, L.L.P.

(57) ABSTRACT

The present application identifies the involvement of the HIFβ-homologous Arntl2 gene in the control of type 1 (insulin-dependent) diabetes. Accordingly, the present invention provides a method of determining the susceptibility of a subject to developing insulin-dependent diabetes based on the expressing level of the Arntl2 gene. The present invention also provides a method for identifying compounds effective for treating or preventing insulin-dependent diabetes in a subject in need thereof and a method of treating or preventing insulin-dependent diabetes by administering an effective amount of compound identified by the identification method. The present invention also provides a method of enhancing protection against insulitis progression or autoimmune diabetes development in a subject in need thereof comprising, enhancing expression of the Arntl2 gene or modulating the expression of target genes thereof.

5 Claims, 25 Drawing Sheets

NOD control (1737 nts)

ATGGAGTTTCCAAGGAAACGCAGAGGCAGAGATTCCCAGCCACTCCAGTCAGAA
TTCATGACAGACACAACAGTGGAAAGTCTTCCCCAGAATCCCTTTGCCTCTCTTCT
TTCAACAAGAACAGGAGTATCGGCGCCCAGTGGCATCAGGGAAGCTCACAGCCA
GATGGAAAAGCGTCGGAGAGACAAGATGAACCATCTGATTCAGAAAATGTCATCT
ATGATCCCTCCACACATCCCCACGGCCCACAAACTGGACAAGCTCAGCGTCTTGA
GGAGGGCGGTGCAGTACTTGAGGTCTCTGAGAGGCATGACAGAGCTTTACTTAGG
AGAAAACTCTAAACCTTCATTTATTCAGGATAAGGAACTCAGTCACTTAATCCTCA
AGGCAGCAGAAGGCTTCCTGTTTGTGGTTGGATGCGAAAGAGGGAGAATTTTTA
CGTTTCTAAGTCTGTCTCCAAAACACTGCGTTATGATCAGGCTAGCTTGATGGGAC
AGAATTTGTTTGACTTCTTACACCCAAAAGACGTCGCCAAAGTAAAGGAACAACT
TTCTTGTGATGGTTCACCAAGAGAGAAACCTATAGACACCAAAACCTCTCAGGTTT
ACAGTCACCCCCACACTGGGCGACCACGCGTGCATTCTGGCTCCAGACGATCTTT
CTTCTTTAGAATGAAGAGCTGTACCGTCCCTGTCAAAGAAGAGCAGCCATGCTCG
TCCTGCTCAAAGAAGAAAGACCATAGAAAATTCCACACCGTCCATTGCACTGGAT
ACTTGAGAAGCTGGCCTCTGAATGTTGTTGGCATGGAGAAAGAGTCGGGTGGTGG
GAAGGACAGCGGTCCTCTTACCTGCCTTGTGGCTATGGGACGGTTGCATCCATACA
TTGTCCCTCAAAAGAGTGGCAAGATCAACGTGAGACCGGCTGAGTTCATAACTCG
CTTCGCAATGAACGGGAAATTCGTCTATGTTGACCAAAGGGCAACGGCAATTTTA
GGATACCTGCCTCAGGAACTTTTGGGAACTTCATGTTATGAATATTTTCATCAGGAT
GACCACAGTAGTTTGACTGACAAGCACAAAGCAGTTCTGCAGAGTAAGGAGAAA
ATACTTACAGACTCATACAAATTCAGAGTGAAGGATGGTGcctTCGTGACTCTGAAG
AGTGAGTGGTTCAGCTTCACAAACCCTTGGACCAAAGAGCTGGAGTACATTGTGT
CTGTCAACACGTTGGTTTTGGGGCGCAGTGAGACCAGGCTGTCTTTGCTTCAGTG
CGGCGGCAGCAGCCAGTCCTCGGAAGACTCATTTAGACAATCCTGCATCAATGTG
CCCGGCGTATCCACGGGGACCATCCTTGGTGCTGGGGGTATTGGAACAGATATTGC
AAATGAGGTTCTGAGTTTACAGAGATTACACTCTTCATCCCCAGAAGATGCAAACC
CTTCAGAAGTGAGAGATGACTGCAGTGTAAACGGTGGGAGCGCCTATGGGCCTGC
ATCCACTAGGGAGCTTTTTGCAGTGAGTCCTTCTAAAACAGAGGTCCTGGAGGCT
GCCAGGCAACACCAGAGCACTGAACCCGCCCACCCTCACGGACCACTTCCCAGT
GACAGTGCCCAGCTGGGTTTTGATGTCCTGTGTGACAGTGACAGCATAGACATGG
CTGCATTCATGAATTACCTCGAAGCAGAGGGGGGCCTGGGTGACCCTGGGGACTT
CAGTGACATCCAGTGGGCACTCTAG

FIGURE 12B

6.VIII (1740 nts)
ATGGAGTTTCCAAGGAAACGCAGAGGCAGAGATTCCCAGCCACTCCAGTCAGAA
TTCATGACAGACACAACAGTGGAAAGTCTTCCCCAGAATCCCTTTGCCTCTCTTCT
TTCAACAAGAACAGGAGTATCGGCGCCCAGTGGCATCAGGGAAGCTCACAGCCA
GATGGAAAAGCGTCGGAGAGACAAGATGAACCATCTGATTCAGAAACTGTCATCT
ATGATCCCTCCACACATCCCCACGGCCCACAAACTGGACAAGCTCAGCGTCTTGA
GGAGGGCAGTGCAGTACTTGAGGTCTCTGAGAGGCATGACAGAGCTTTACTTAGG
AGAAAACTCTAAACCTTCATTTATTCAGGATAAGGAACTCAGTCACTTAATCCTCA
AGGCAGCAGAAGGCTTCCTGTTTGTGGTTGGATGCGAAAGAGGGAGAATTTTTA
CGTTTCTAAGTCTGTCTCCAAAACACTGCGTTATGATCAGGCTAGCTTGATGGGAC
AGAATTTGTTTGACTTCTTACACCCAAAAGACGTCGCCAAAGTAAAGGAACAACT
TTCTTGTGATGGTTCACCAAGAGAGAAACCTATAGACACCAAAACCTCTCAGGTTT
ACAGTCACCCCCACACTGGGCGACCACGCGTGCATTCTGGCTCCAGACGATCTTT
CTTCTTTAGAATGAAGAGCTGTACCGTCCCTGTCAAAGAAGAGCAGCCATGCTCG
TCCTGCTCAAAGAAGAAAGACCATAGAAAATTCCACACCGTCCATTGCACTGGAT
ACTTGAGAAGCTGGCCTCTGAATGTTGTTGGCATGGAGAAAGAGTCGGGTGGTGG
GAAGGACAGCGGTCCTCTTACCTGCCTTGTGGCTATGGGACGGTTGCATCCATACA
TTGTCCCTCAAAAGAGTGGCAAGATCAACGTGAGACCGGCTGAGTTCATAACTCG
CTTCGCAATGAACGGGAAATTCGTCTATGTTGACCAAAGGGCAACGGCAATTTTA
GGATACCTGCCTCAGGAACTTTTGGGAACTTCATGTTATGAATATTTTCATCAGGAT
GACCACAGTAGTTTGACTGACAAGCACAAAGCAGTTCTGCAGAGTAAGGAGAAA
ATACTTACAGACTCATACAAATTCAGAGTGAAGGATGGTGCCTTCGTGACTCTGAA
GAGTGAGTGGTTCAGCTTCACAAACCCTTGGACCAAAGAGCTGGAGTACATTGTG
TCTGTCAACACGTTGGTTTTGGGGCGCAGTGAGACCAGGCTGTCTTTGCTTCAGT
GCAGCAGCAGCAGCCAGTCCTCGGAAGACTCATTTAGACAATCCTGCATCAATGT
GCCCGGCGTATCCACGGGGACCGTCCTTGGTGCTGGGAGTATTGGAACAGATATTG
CAAATGAGGTTCTGAGTTTACAGAGATTACACTCTTCATCCCCAGAAGATGCAAAC
CCTTCAGAAGAAGTGAGAGATGACTGCAGTGTAAACGGTGGGAGCGCCTATGGG
CCTGCATCCACTAGGGAGCTTTTTGCAGTGAGTCCTTCTAAAACAGAGGTCCTGG
AGGCTGCCAGGCAACACCAGAGCACTGAACCCGCCCACCCTCACGGACCACTTC
CCAGTGACAGTGCCCAGCTGGGTTTTGATGTCCTGTGTGACAGTGACAGCATAGA
CATGGCTGCATTCATGAATTACCTCGAAGCAGAGGGGGGCCTGGGTGACCCTGGG
GACTTCAGTGACATCCAGTGGGCACTCTAG

FIGURE 13A

NOD control (504 bases)
CATCTCCTAGATGACTGTAAATGTCATCAAGGTGAAGATGGAGATTCACCACTCCC
AGGGGTGACCGGAGACCTCCTTTCTTCCAG<u>GTCAGAATTCATGACAGACACAACA
GTGGAAAGTCTTCCCCAGAATCCCTTTGCCTCTCTTCTTTCAACAAGAACAGGAGT
ATCGGCGCCCAGTGGCATCAGG</u>TAAGTTTCCCTGCTGATCTCCCTGCCATGGAAGA
GGCTGCTCCTCAGAGTTTCGCCCTGGCCCAGTTCTCCTCTGCTCCCACCATTTTAT
GTGATTTCTCAGACTGTAGTTCTTGCCAAATGCTGGATGTTTGTGATATCTCACCCA
GGGTGAGAAAGGCAGTCCAGGGACGTATGAGCATTTTGTGCCCATAGCCCCAGA
CTTTTTTTAATACTTGTAAAGAAGATCCCATGAGAATGGCCACTTTCTTGTGGTCCT
ATTGGCTTTGGGTAGATAGCTGATCCTCTCAAAGAGATGGTGACCAGATTCCTGTG

6.VIII (504 bases)
CATCTCCTAGATGACTGTAAATGTCATCAAGGTGAAGATGGAGATTCACCACTCCC
AGGGGTGACCGGAGACCTCCTTTCTTCCAG<u>GTCAGAATTCATGACAGACACAACA
GTGGAAAGTCTTCCCCAGAATCCCTTTGCCTCTCTTCTTTCAACAAGAACAGGAGT
ATCGGCGCCCAGTGGCATCAG</u>GTAAGTTTCCCTGCTGATCTCCCTGCCATGGAAGA
GGCTGCTCCTCAGAGTTTTGCCCTGGCCCAGTTCTCCTCTGCTCCCACCATTTTATG
TGATTTCTCAGACTGTAGTTCTTGCCAAATGCTGGATGTTTGTGATATCTCACCCAG
GGTGAGAAAGGCAGTCCAGGGACGTATGAGCATTTTGTGCCCATAGCCCCAGAC
TTTTTTTAATACTTGTAAAGAAGATCCCATGAGAATGACCACTTTCTTGTGGTCCTA
TTGGCTTTGGGTAGATAGCTGATCCTCTCAAAAGATGGTGACCAGATTCCTGTG

FIGURE 13B

NOD control (332 bases)
GCACACACAGGCATGCACTTGGTACATAGACATTCACTTGGATGAACACAACACA
CATAAAATAAACATAGTTTTTAAAAGTTAAAGAAATAATGATCTAACCAGTTTTTAA
TTTTTGTTTGAGACAGGTTTTACTATGTAGCCTTTGCTGGTCTGTAGCTCCTTATGT
AGACCAGGCTGGCTTTGAACTCACTCCCTGAAGGAAGTCTTAAGATAAATTGCAA
GTGTTTTAAATTGTTGAGTGTGGTGATCCATGCCTGCAACTCCAACACTCTAAAGT
TTGAGCCCCCCACCCCCCAGACCTACACTCTCCTCGAAAACAAAACACTG

6.VIII (332 bases)
GCACACACAGGCATGCACTTGGTACATAGACATTCACTTGGATGAACACAACACA
CATAAAATAAACGTAGTTTTTAAAAGTTAAAGAAATAATGATCTAACCAGTTTTTAA
TTTTTGTTTGAGACAGGTTTTACTATGTAGCCTTTGCTGGTCTGTAGCTCCTTATGT
AGACCAGGCTGGCTTTGAACTCACTCCCTGAAGGAAGTCTTAAGATAAATTGCAA
GTGTTTTAAATTGTTGAGTGTGGTGATCCATGCCTGCAACTCCAACACTCTAAAGT
TTGAGCCCCCCACCCCCCAGACCTACACTCTCCTCGAAAACAAAACACTG

FIGURE 13C

NOD control (493 bases)
TGAGACCACTGGGGCATTTGCCATAGATCCTGATCTTAGCTGAAGTGAACAATAAA
ATACAAATGAGTGGAAATTTGGCAAATCAAATACTTGGAGCCAACATGGATGCATT
AATAGATTCCCTGCCCCTCAGGGAGTGTCATGTGCTTTTCTGACCTCCAG<u>GGGGCG</u>
<u>CAGTGAGACCAGGCTGTCTTTGCTTCAGTGCGGCGGCAGCAGCCAGTCCTCGGA</u>
<u>A</u>GGTAAGACGGAGCTTCAGGTCAGGCGTGGTAACTCAGATGCATCATCCGGTAAG
GATTCCATGAAGACGTGCTTTTCTGTCTAAGAATGGAGAAACTTTCCAGGGAAAG
TTAGAAAACATTTTGACTGGACAGGTCCGTGCACTGGGCTATAGGAGGAGATAGG
GGCAGGAGAGGTGGTTCAGAAATTCCGGGCCCTTCTTGTATACAGATACTGATCTG
AGTTTAATCTCCAAAACATACATGAAGGTAGAAGGAAAGGACTGACATCA

6.VIII (493 bases)
TGAGACCACTGGGGCATTTGCCACAGATCCTGATCTTAGCTGAAGTGAACAATAA
AATACAAATGAGTGGAAATTTGGCAAATCAAATACTTGGAGCCAACGTGGATGCA
TTAATAGATTCCCTGCCCCTCAGGGAGTGTCATGTGCTTTTCTGACCTCCAG<u>GGGG</u>
<u>CGCAGTGAGACCAGGCTGTCTTTGCTTCAGTGCAGCAGCAGCAGCCAGTCCTCGG</u>
<u>AA</u>GGTAAGACGGAGCTTCAGGTCAGGCGTGGTAACTCAGATGCATCATCCGGTAA
GGATTCCATGAAGACGTGCTTTTCTGTCTAAGAATGGAGAAACTTTCCAGGGAAA
GTTAGAAAACATTTTGACTGGACAGGTCCGTGCACTGGGCTATAGGAGGAGATAG
GGGCAGGAGAGGTGGTTCAGAAAGTCCGGGCCCTTCTTGTATACAGATACTGATC
TGAGTTTAATCTCCAAAACATACATGAAGGTAGAAGGAAAGGACTGACATCA

FIGURE 13D

NOD control (367 bases)
TCGCTCACTGAGACTCTCCTCCCAGGTTCTAGATTGCAGCAAATTGACATTTAAAG
CTAAGACTTGGGGGCTGGAGAAATGTCTCAATGGCTAAGAGCACTGACTGTTCTT
CCGAGAGGATCTGGGTTCAATCTCCAGCACCCACATGGCAGCTCACCACTGTCTG
TACCTCCAATATTTGACACCCTCACATCAGACATATGTGGAGGCAAAACACCAATG
CAGATAAAATAAAATAAAACGCTAAGCCTCACCCAGGTTTACCTCTTGTATCCCGG
GTTGGGCTCTCACATGTCTGTAGCTAAAGATCACCTGGAACTTCTGGTTCTCCCAC
CTCATGCTGGGGTTGCAGGTGTATACCACCATG

6.VIII (367 bases)
TCGCTCACTGAGACTCTCCTCCCAGGTTCTAGATTGCAGCAAATTGACATTTAAAG
CTAAGACTTGGGGGCTGGAGAAATGTCTCAATGGCTAAGAGCACTGACTGTTCTT
CCGAGAGGATCTGGGTTCAATCTCCAGCACCCACATGGCAGCTCACCACTGTCTG
TACCTCCAATATTTGACACCCTCACACCAGACATATGTGGAGGCAAAACACCAATG
CAGATAAAATAAAATAAAACGCTAAGCCTCACCCAGGTTTACCTCTTGTATCCCGG
GTTGGGCTCTCACATGTCTGTAGCTAAAGATCACCTGGAACTTCTGGTTCTCCCAC
CTCATGCTGGGGTTGCAGGTGTATACCACCATG Bmal2 coding region - exons marked by different colors (CO as example)

NOD control (CO, 1737 nts)

ATGGAGTTTCCAAGGAAACGCAGAGGCAGAGATTCCCAGCCACTCCA GTCAGAATTCATGACA
GACACAACAGTGGAAAGTCTTCCCCAGAATCCCTTTGCCTCTCTTCTTTCAACAAGAACAGGAGTA
TCGGCGCCCAGTGGCATCAGGGAAGCTCACAGCCAGATGGAAAAGCGTCGGAGAGACAAGAT
GAACCATCTGATTCAGAAAATGTCATCTATGATCCCTCCACACATCCCCACGGCCCACAAACT
GGACAAGCTCAGCGTCTTGAGGAGGGCGGTGCAGTACTTGAGGTCTCTGAGAGGCATGACAG
AGCTTTACTTAGGAGAAAACTCTAAACCTTCATTTATTCAGGATAAGGAACTCAGTCACTTAATCCTC
AAG GCAGCAGAAGGCTTCCTGTTTGTGGTTGGATGCGAAAGAGGGAGAATTTTTTACGTTTC
TAAGTCTGTCTCCAAAACACTGCGTTATGATCAGGCTAGCTTGATGGGACAGAATTTGTTTGACT
TCTTACACCCAAAAGACGTCGCCAAAGTAAAGGAACAACTTTCTTGTGATGGTTCACCAAGAGAGA
AACCTATAGACACCAAAA<u>CCTCTCAGGTTTACAGTCACCCCCACACTGGGCGACCACGCGTGC</u>
<u>ATTCTGGCTCCAGACGATCTTTCTTCTTTAGAATGAAGAGCTGTACCGTCCCTGTCAAAGAAG</u>
<u>AGCAGCCATGCTCGTCCTGCTCAAAGAAGAAAGACCATAGAAAATTCCACACCGTCCATTGCAC</u>
<u>TGGATACTTGAGAAGCTGGCCTCTGAATGTTGTTGGCATGGAGAAAGAGTCGGGTGGTGGGAAGGA</u>
<u>CAGCGGTCCTCTTACCTGCCTTGTGGCTATGGGACGGTTGCATCCATACATTGTCCCTCAAAAGAGT</u>
<u>GGCAAGATCAACGTGAGACCGGCTGAGTTCATAACTCGCTTCGCAATGAACGGGAAATTCGTCTAT</u>
<u>GTTGACCAAAGGGCAACGGCAATTTTAGGATACCTGCCTCAGGAACTTTTGGGAACTTCATGT</u>
<u>TATGAATATTTTCATCAGGATGACCACAGTAGTTTGACTGCAAGCACAAAGCAG</u>*TTCTGCAGA*
*GTAAGGAGAAAATACTTACAGACTCATACAAATTCAGAGTGAAGGATGGTGCCTTCGTGACTCTGAAGAGT*
*GAGTGGTTCAGCTTCACAAACCCTTGGACCAAAGAGCTGGAGTACATTGTGTCTGTCAACACGTTGGTTTT*
GGGGCGCAGTGAGACCAGGCTGTCTTTGCTTCAGTGCGGCGGCAGCAGCCAGTCCTCGGAAG*ACTC*
*ATTTAGACAATCCTGCATCAATGTGCCCGGCGTATCCACGGGGACCATCCTTGGTGCTGGGGGTATTGGA*
*ACAGATATTGCAAATGAGGTTCTGAGTTTACAGAG*ATTACACTCTTCATCCCCAGAAGATGCAAACCCTT
CAGAAGTGAGAGATGACTGCAGTGTAAACGGTGGGAGCGCCTATGGGCCTGCATCCATCAGGGAG
CTTTTTGCAGTGAGTCCTTCTAAAACAGAGGTCCTGGAGGCTGCCAGGCAACACCAGAGCAC
TGAACCCGCCCACCCTCACGGACCACTTCCCAGTGACAGTGCCCAGCTGGGTTTTGATGTCCTG
TGTGACAGTGACAGCATAGACATGGCTGCATTCATGAATTACCTCGAAGCAGAGGGGGGCCTGGGT
GACCCTGGGGACTTCAGTGACATCCAGTGGGCACTCTAG

NOD control (1280 bases)
GGGAGGATTGTTAGCACGTCTGTGATTATTCTGTTCTCATTCCTGCTGCTGTGA
AAGCCTCTCAGGTTTACAGTCACCCCCACACTGGGCGACCACGCGTGCATTCT
GGCTCCAGACGATCTTTCTTCTTTAGAATGAAGAGCTGTACCGTCCCTGTCAAA
GAAGAGCAGCCATGCTCGTCCTGCTCAAAGAAGAAAGACCATAGAAAATTCC
ACACCGTCCATTGCACTGGATACTTGAGAAGCTGGCCTCTGAATGTTGTTGGCA
TGGAGAAAGAGTCGGGTGGTGGGAAGGACAGCGGTCCTCTTACCTGCCTTGT
GGCTATGGGACGGTTGCATCCATACATTGTCCCTCAAAAGAGTGGCAAGATCA
ACGTGAGACCGGCTGAGTTCATAACTCGCTTCGCAATGAACGGGAAATTCGTC
TATGTTGACCAAAGGGCAACGGCAATTTTAGGATACCTGCCTCAGGAACTTTT
GGGAACTTCATGTTATGAATATTTTCATCAGGATGACCACAGTAGTTTGACTGA
CAAGCACAAAGCAGTTCTGCAGAGTAAGGAGAAAATACTTACAGACTCATAC
AAATTCAGAGTGAAGGATGGTGcctTCGTGACTCTGAAGAGTGAGTGGTTCAGC
TTCACAAACCCTTGGACCAAAGAGCTGGAGTACATTGTGTCTGTCAACACGTT
GGTTTTGGGGCGCAGTGAGACCAGGCTGTCTTTGCTTCAGTGCGGCGGCAGC
AGCCAGTCCTCGGAAGACTCATTTAGACAATCCTGCATCAATGTGCCCGGCGTA
TCCACGGGGACCATCCTTGGTGCTGGGGGTATTGGAACAGATATTGCAAATGA
GGTTCTGAGTTTACAGAGATTACACTCTTCATCCCCAGAAGATGCAAACCCTTC
AGAAGTGAGAGATGACTGCAGTGTAAACGGTGGGAGCGCCTATGGGCCTGCA
TCCACTAGGGAGCTTTTTGCAGTGAGTCCTTCTAAAACAGAGGTCCTGGAGGC
TGCCAGGCAACACCAGAGCACTGAACCCGCCCACCCTCACGGACCACTTCCC
AGTGACAGTGCCCAGCTGGGTTTTGATGTCCTGTGTGACAGTGACAGCATAGA
CATGGCTGCATTCATGAATTACCTCGAAGCAGAGGGGGCCTGGGTGACCCTG
GGGACTTCAGTGACATCCAGTGGGCACTCTAGCATTTTGGCTTTGTACTTTAAC
ATGAGAATCATTTCAGAGTGTTTCATTGACAAAACACTGTACTCTTGAGCACTG
TATTG

FIGURE 15B

6.VIII (1283 bases)

GGGAGGATTGtTAGCACGTCTGTGATTATTCTGTTCTCATTCCTGCTGCTGTGAA
AGCCTCTCAGGTTTACAGTCACCCCCACACTGGGCGACCACGCGTGCATTCTG
GCTCCAGACGATCTTTCTTCTTTAGAATGAAGAGCTGTACCGTCCCTGTCAAAG
AAGAGCAGCCATGCTCGTCCTGCTCAAAGAAGAAAGACCATAGAAAATTCCA
CACCGTCCATTGCACTGGATACTTGAGAAGCTGGCCTCTGAATGTTGTTGGCAT
GGAGAAAGAGTCGGGTGGTGGGAAGGACAGCGGTCCTCTTACCTGCCTTGTG
GCTATGGGACGGTTGCATCCATACATTGTCCCTCAAAAGAGTGGCAAGATCAA
CGTGAGACCGGCTGAGTTCATAACTCGCTTCGCAATGAACGGGAAATTCGTCT
ATGTTGACCAAAGGGCAACGGCAATTTTAGGATACCTGCCTCAGGAACTTTTG
GGAACTTCATGTTATGAATATTTTCATCAGGATGACCACAGTAGTTTGACTGAC
AAGCACAAAGCAGTTCTGCAGAGTAAGGAGAAAATACTTACAGACTCATACA
AATTCAGAGTGAAGGATGGTGCCTTCGTGACTCTGAAGAGTGAGTGGTTCAGC
TTCACAAACCCTTGGACCAAAGAGCTGGAGTACATTGTGTCTGTCAACACGTT
GGTTTTGGGGCGCAGTGAGACCAGGCTGTCTTTGCTTCAGTGCAGCAGCAGC
AGCCAGTCCTCGGAAGACTCATTTAGACAATCCTGCATCAATGTGCCCGGCGTA
TCCACGGGGACCGTCCTTGGTGCTGGGAGTATTGGAACAGATATTGCAAATGA
GGTTCTGAGTTTACAGAGATTACACTCTTCATCCCCAGAAGATGCAAACCCTTC
AGAAGAAGTGAGAGATGACTGCAGTGTAAACGGTGGGAGCGCCTATGGGCCT
GCATCCACTAGGGAGCTTTTGCAGTGAGTCCTTCTAAAACAGAGGTCCTGGA
GGCTGCCAGGCAACACCAGAGCACTGAACCCGCCCACCCTCACGGACCACTT
CCCAGTGACAGTGCCCAGCTGGGTTTTGATGTCCTGTGTGACAGTGACAGCAT
AGACATGGCTGCATTCATGAATTACCTCGAAGCAGAGGGGGCCTGGGTGACC
CTGGGGACTTCAGTGACATCCAGTGGGCACTCTAGCATTTTGGCTTTGTACTTT
AACATGAGAATCATTTCAGAGTGTTTCATTGACAAAACACTGTACTCTTGAGC
ACTGTATTG

FIGURE 16

NOD control (CO)
CATTTTGGCTTTGTACTTTAACATGAGAATCATTTCAGAGTGTTTCATTGACAAAAC
ACTGTACTCTTGAGCACTGTATTGGTACATTTATCTCTTATTACTAGTCTACTGACTT
TTATAATATATCTGCCCTTTATTCTCACTGGGATGTGCGGAGTCACACATGCTCCTCC
AAAGAGAAACAGCCAAGTTTATCAGTCCCTCTTTACACAGTGAGAAGGCAGCTTG
GGGGTCAGGCTGCCATATTTTGCTAAAATATTCTGACCAAAAACTGCTACCAACC
ATATTGTTAGGGCTTTTTTTTTACATTTATTTATTTACTATATGTAAGTACACTGTAG
CTGTCCTCAGATACTCCAGAAAAGGGAATCAGATTTCGTTGGGGATGGTTGTGTGC
CACCATGTGGTTGCTGGGATTTGAACTCGGGACTTTCGGAAGAGCAGTCGGCGCT
CTTAACCACTGAGCCATCTCACCAGCCCTGTTCTTGTTTTCAAGACAAGGTTTCT
CTGTGTATCCCTGGCTGTCTTGTAACTCACTCTGTAGACCAGGCTGGCCTTGAACT
CAAAGATCTGCCTGCCTCCTCTTCCTCCCAAGTGTTGAGATTAAAGCCATACATCA
CAATTCCCAGCTTA

6.VIII
CATTTTGGCTTTGTACTTTAACATGAGAATCATTTCAGAGTGTTTCATTGACAAAAC
ACTGTACTCTTGAGCACTGTATTGGTACATTTTTATCTCTTATTACTAGTCTACTGA
CTTTTATATATCTGCCCTTTATTCTCACTGGGATGTGCGGAGTCACACATGCTCCTC
CAAAGAGAAACAGCCAAGTTTATCAATCCCTCTTTACACAGTGAGAAGGCAGCTT
GGGGGTCAGGCTGCCATATTTTGCTAAAATATTCTGACCAAAAACTGCTACCAAC
CATATTGTTAGGGCTTTTTTAAATATATATACTTTTGTTTTTGAGTTTGGGATTTT
TGTTTTGTTCTGTCTGTTTTCTGTTTTGTCTTCAAGACAGGGTTTCTCTGTGTAGC
CCTGGCTGTCTTGTAACTCACTCTGTAGACCAGGCTGGCCTTGAACTCAAAGATCC
GCCTGCCTCTTCCTCCCAAGTGTTGAGATTAAAGCCATATATCACAATTCCCAGCTT
A

FIGURE 17A

NOD control ( 774 bases)
TTACTGGAGGGATTACAGATAGGTGGGTTTGGAGTCACCCGGTTGGAGGAGGAAA
GACAGGGGAAGGTGGAAGAACGGGAAGAGAAAGGAAGCTGCCATGAGAGGAGA
TGGACCACAAGCACGTGGCCAGGAGAAACAGCAAGTATCCCGGGTACATCCCTG
GGGAGGTAGCCAGGCCAGCAGTTAGAAGAGTAGATTAGGGGTGACCTCCCAGTAA
TTTTCAAAGCCAAATAAAATAACCATAGTTTGAGTCTCATTTATTTGTAAGCTAGTC
TGGGATAAGCTTACATTGCTTGCACTACAAGATTTCCTCCGGTTCTGCAGTGCTCAT
TTCTTAGACTTTCCCCGACTGAGAAAACAGAAGCGAATGGGTGGGTGTTCATTCA
TTTCGGCGGTGGCTGAGGGAATGGCTGGGTGACAGAGGTAAGGGCAGCATTGTG
CAGTCAGGACAGGATAACTCTGCCTCGCTGCTGGAGTGGAACTTCGATCAAGCTC
CTGTCCACGAGGCTTGGTCTCTCTCTGAACAACGGTCTGTCTAGAAAGCCAGAGT
TCGGGCGACCTGGGTGGATCTCCGACCTATGCGGCAGAGTCGGTGAGTTCTTTCT
GAGCTGTAGTTTATTAGCTTTCGGGGTTTTGAGTGGTTTTTGCGTGTGATAGGAAC
AGCAGCTTGGGAACCCATTTGCCACACTGTATTAACTAAGAAGGTCCACACCCTCT
TGCCCTCTGGACCTAACAAAAAGAGTGTGCGACCCAGTCCTTGGAGATCCAGTGA
C

6.VIII (775 bases)
TTACTGGAGGGATTACAGATAGGTGGGTTTGGAGTCACCCGGTTGGAGGAGGAAA
GACAGGGGAAGGTGGAAGAACGGGAAGAGAAAGGAAGCTGCCATGAGAGGAGA
TGGACCACAAGCACGTGGCCAGGAGAAACAGCAAGTATCCCGGGTACATCCCTG
GGGAGGTAGCCAGGCCAGCAGTTAGAAGAGTAGATTAGGGGTGACCTCCCAGTAA
TTTTCAAAGCCAAATAAAATAACCATAGTTTGAGTCTCATTTATTTGTAAGCTAGTC
AGGGATAAGCTTACATTGCTTGCACTACAAGATTTCCTCCAGTTCTGCAGTGTTCA
TTTCTTAGACTTTCCCCGACTGAGAAAACAGAAGCGAATGGGTGGGTGTTCATTC
ATTTCTGGCGGTGGCTGAGGGAATGGCTGGGTGACAGAGGTAAGGGCAGCATTGT
GCAGTCAGGACAGGATAACTCTGCCTCGCTGCTGGAGTGGAACTTCGATCAAGCT
CCTGTCCACGAGGCTTGGTCTCTCTCTGAACAACGGTCTGTCTAGAAAGCCAGAG
TTTCGGGCGACCTGGGTGGATCTCCGACCTATGCGGCAGAGTCGGTGAGTTCTTTC
TGAGCTGTAGTTTATTAGCTTTCGGGGTTTTGAGTGGTTTTTGCGTGTGATAGGAA
CAGCAGCTTGGGAACCCATTTGCCACACTGTATTAACTAAGAAGGTCCACACCCT
CTTGCCCTCTGGACCTAACAAAAAGAGTGTGCGACCCAGTCCTTGGAGATCCAGT
GAC

FIGURE 17B

NOD control ( 683 bases)
ATTTATGTGGGCAGAGTGAGTGTAACTGAGGAATCCCCCTCGCGACCGTAGGATG
AAGGGAGCTCCGGAGCTCCAAGGAGTCTTGGTTACATATGTGCCTAACTGTTACA
GGAGTCCCTGGGGCGGTTGTAAAAAGAAAAGGGTCAGGACCACAGACCAGTCTT
TCTTGCACCATGAAGGGTCTCCCTGTCCTCCACCTCTTGCTTTTCCTCTTGCCTTTT
CAGCGCCACTGAGGGCGTTCCTCTTGGTTTAGGGCGGATCTCAACGCTGCTCCGC
CAGCCTCTGCGCTTGGGGCTCTGCTGAGGCTCCGCCGGTGCGGGTGCCTTGTCCC
GCCCGGGGCTGGCTAGGGCTGCCGGGCCTGCGATGCCCAAGCCCTGTGCGCCAG
GGCCGAATGCAGGGAGCCGCGGGGCTGCAGCTCCAGGTGAGTGGCTTGTCGAGA
CCCCGAAACTGTGTCGGGCGTCCTTGACAGCAAGCCAGTACCCCATTCCAAGCTG
GGGGAGGGGTCCCCGCATGTCTACACCAGGGTCTCATCTGATGGCTGTGGATCAA
GGCGGTAGGTTCGCACAGCCCCAGCGCAGTTGTATCACCTCCGGGACCCAGTCCG
GCGTGTGGGGTCCAGTCCCAGCTGCGTCCTACAGTGGGCGAGCTGCGGGTACAAT
CCAGAGTCTGCATACTCTACAGTT

6.VIII (683 bases)
ATTTATGTGGGCAGAGTGAGTGTAACTGAGGAATCCCCCTCGCGACCGTAGGATG
AAGGGAGCTCCGGAGCTCCAAGGAGTCTTGATTACATATGTGCCTAACTGTTACAG
GAGTCCCTGGGGCGGTTGTAAAAAGAAAAGGGTCAGGACCACAGACCAGTCTTT
CTTGCACCATGAAGGGTCTCCCTGTCCTCCACCTCTTGCTTTTCCTCTTGCCTTTTC
AGCGCCACTGAGGGCGTTCCTCTTGGTTTAGGGCGGATCTCAACGCTGCTCCGCC
AGCCTCTGCGCTTGGGGCTCTGCTGAGGCTCCGCCCGTGCGGGTGCCTTGTCCCG
CCCGGGGCTGGCTAGGGCTGCCGGGCCTGCGATGCCCAAGCCCTGTGCGCCAGG
GCCGAATGCAGGGAGCCGCGGGGCTGCAGCTCCAGGTGAGTGGCTTGTCGAGAC
CCCGAAACTGTGTCGGGCGTCCCTGACAGCAAGCCAGTACCCCATTACAAGCTGG
AGGAGGGGTCCCCGCATGTCTACACCAGGGTCTCATCTGATGGCTGTGGATCAAG
GCGGTAGGTTCGCACAGCCCCAGCGCAGTTGTATCACCTCCGGGACCCAGTCCGG
CGTGTGGGGTCCAGTCCCAGCTGCGTCCTACAGTGGGCGAGCTGCGGGTACAATC
CAGAGTCTGCATACTCTACAGTT

FIGURE 17C

NOD control (867 bases)
TCCAGAGTCTGCATACTCTACAGTTTGCTCCTCTCTGGAAGAAGCACCAGGATCCA
GGGTGCTGCTGGAGGCCTCGTTGTGCTGCGTTCCAATGGCCAAGTCCAGGCCTGG
GGAGTGCAGAGGCGCGCGCAAGCACCCTCTTATCACGGTCTCTCTGGGCTTGTGG
TGGGAATGGGGAAGCAAACCTCTTATCTTCCGGGGCTGGGTATTGAACCCAGGAC
TCCAGGCTAGTACTGTAATCTCTGCTCCTTTCATTTTGTGAGTCAAGTTGGGAGTTT
TGCCTCACCTGTCCTTTCTGTTGCTCTCAGTGATAAACTGGGAGGTGTCTCCCTGG
GAACATGGTGACCATTATTTCACAGAGGATAATCATAAAAAGCTGTTATTTATGGCA
GGCGGAAGTCAGGAAGAAAAGAACACACCAATAAATAAAAGCAGGCATGGAAGT
CAAGGTCACAGTTATTTTGATTAACAGACTAGCTGGCTGACTGAGATTGATGCTTG
ATTGATTGGTTGATTGATTGGTTGATTGGTTGATTGATTGATTAATTGATTGATTGAT
GTGTAGCCTTTGGCTAGCCTGTAACTTGCTGTACCACCAACTTAACCTGGACTTGC
ATCTGAAGAGCTGGCTACAGGTTTGTCTCATCTTTCTGGTGTAACTTTAATCAATGA
TGGGGAAATTTCTGTCTGTGACCTTTCAAGGGTTCCTGTGGTCTCCCTGCCTGCAT
GGTGCTCAAATCCATTTTGCTAAAAGAAGGTCCCTTCTTGCTCTAAGCTCTGCTT
CACTCTCTTCTGGGTGCCTCAGTTTCCTCCCTGTAATATGGGGGTAATGACTACATA
GGTCTCTGCATTCTGCAACTGTAAGG

6.VIII (867 bases)
TCCAGAGTCTGCATACTCTACAGTTTGCTCCTCTCTGGAAGAAGCACCAGGATCCA
GGGTGCTGCTGGAGGCCTCGTTGTGCTGCGTTCCAATGGCCAAGTCCAGGCCTGG
GGAGTGCAGAGGCGCGCGCAAGCACCCTCTTATCACGGTCTCTCTGGGCTTGTGG
TGGGAGTGGGGAAGCAAACCTCTTATCTTCCGGGGCTGGGTATTGAACCCAGGAC
TCCAGGCTAGTACTGTAATCTCTGCTCCTTTCATTTTGTGAGTCAAGTTGGGAGTTT
TGCCTCACCTGTCCTTTCTGTTGCTCTCAGTGATAAACTGGGAGGTGTCTCCCTGG
GAACATGGTGACCATTATTTCACAGAGGATAATCATAAAAAGCTGTTATTTATGGCA
GGCGGAAGTCAGGAAGAAAAGAACACACCAATAAATAAAAGCAGGCATGGAAGT
CAAGGTCACAGTTATTTTGATTAACAGACTAGCTGGCTGACTGAGATTGATGCTTG
ATTGATTGGTTGATTGATTGGTTGATTGGTTGATTGATTGATTAATTGATTGATTGAT
GTGTAGCCTTTGGCTAGCCTGTAACTTGCTGTACCACCAACTTAACCTGGACTTGC
ATCTGAAGAGCTGGCTACAGGTTTGTCTCATCTTTCTGGTGTAACTTTAATCAATGA
TGGGGAAATTTCTGTCTGTGACCTTTCAAGGGTTCCTGTGGTCTCCCTGCCTGCAT
GGTGCTCAAATCCATTTTGCTAAAAGAAGGTCCCTTCTTGCTCTAAGCTCTGCTT
CACTCTCTTCTGGGTGCCTCAGTTTCCTCCCTGTAAGATGGGGGTAATGACTACAT
AGGTCTCTGCATTCTGCAACTGTAAGG

FIGURE 17D

NOD control (577 bases)
ACACACACACACACACACACTAGGTGGGGCCAAACATAACTGCCTGCTCAGTT
AACATTTTATGAGAGCAGCTTATGGATTAGACACTGATGCTGAGCCTGCTGCCCTG
CCCAGCAGTTGAGCATCCTCTTGGAAGACGGTCCCAGAACCCTTGGAGCTAGAGG
GAGGACCCTTCCAGAAAGCCACACACTGGCCAGAATCGCCTGCAGGGGCAGCTT
CTTTAATAGCATCTCACCTCCTCCCCTTCTCAGCTGCTCATCTCTTCTGTGATGTTAC
TGGACCTAGCTCTTTTGAGTTGTCGTTTTGCAACGGTGGTGGCTTAAATTCATGC
TCCTGACTCAGAAGGCATCCCAATCTGCTTTGCATAAACTGTTGTTCCTGGCCTGT
GTGTCCTAGGCAGTTCCTTCCAGGAGTGCATCACACAAGCTAATCCAGGATGGGC
TTGGGCCCTGACTTGCTCTGGTGTGGGGATCGAGTTCATTAGTCAGCCCAGAACC
CTCTCGACATTATCAGGGACTCAGTGTTGGCCTATAAGGCCCAAAGGAAGCTGAG
CCATCTGCCTGCCCTGAAGGTT

6.VIII (577 bases)
ACACACACACACACACACACACAAGGTGGGGCCAAACATAACTGCCTGCTCAGT
TAACATTTTATGAGAGCAGCTTATGGATTAGACACTGATGCTGAGCCTGCTGCCCT
GCCCAGCAGTTGAGCATCCTCTTGGAAGACGGTCCCAGAACCCTTGGAGCTAGAG
GGAGGACCCTTCCAGAAAGCTACACAGTGGCCAGAAGCGCCTGCAGGGGCAGCT
TCTTTAACAGCATCTCACCTCCTCCCCTTCTCAGCTGCTCATCTCTTCTGTGATGTT
ATTGGACCTAGCTCTTTTGAGTTGTCGTTTTGCAACGGTGGTGGCTTAAATTCAT
GCTCCTGACTCAGAAGGCATCCCAATCTGCTTTGCATAAACTGTTGTTCCTGGCCT
GTGTGTCCTAGGCAGTTCCTTCCAGGAGTGCATCACACAAGCTAATCCAGGATGG
GCTTGGGCCCTGACTTGCTCTGGTGTGGGGATCGAGTTCATTAGTCAGCCCAGAA
CCCTCTCGACATTATCAGGGACTCAGTGTTGGCCTATAAGGCCCAAAGGAAGCTG
AGCCATCTGCCTGCCCTGAAGGTT

METHOD OF DETERMINING THE SUSCEPTIBILITY OF A SUBJECT TO DEVELOPING INSULIN-DEPENDENT DIABETES

CROSS-REFERENCE TO RELATED APPLICATIONS

This application claims priority to U.S. provisional application 60/776,662, filed on Feb. 27, 2006, the entire contents of which is incorporated herein by reference.

BACKGROUND OF THE INVENTION

1. Field of the Invention

The present application implicates the involvement of the HIFβ-homologous Arntl2 gene in the control of type 1 (insulin-dependent) diabetes. Accordingly, the present invention provides a method of determining the susceptibility of a subject to developing insulin-dependent diabetes based on the expressing level of the Arntl2 gene. The present invention also provides a method for identifying compounds effective for treating or preventing having insulin-dependent diabetes in a subject in need thereof and a method of treating or preventing insulin-dependent diabetes by administering an effective amount of compound identified by the identification method. The present invention also provides a method of enhancing protection against insulitis progression or autoimmune diabetes development in a subject in need thereof comprising, enhancing expression of the Arntl2 gene.

2. Discussion of the Background

Type 1 or insulin dependent diabetes (IDDM) is an autoimmune disease characterized by the progressive destruction of insulin-producing β-cells of the islets of Langerhans by infiltrating lymphocytes (1, 2). The disease, which affects about 0.3% of the Caucasian population, is both multifactorial and polygenic, with the MHC class II locus and the insulin locus being the two best studied genetic loci (3, 4).

The non-obese diabetes (NOD) mouse (5, 6) is a well-characterized animal model of IDDM. More than twenty murine insulin dependent diabetes susceptibility loci (Idd) have been genetically identified (7), but little information has been obtained about the nature of these non-MHC Idd genes. Construction of congenic strains, differing from the NOD receiver strain by only a selected genetic region derived from a non-diabetes prone parental donor strain (8, 9), is a widely used approach allowing the definition of disease-related candidate regions. A promising strategy for candidate gene identification is to combine a variety of phenotypic studies of congenic mice with expression profiling, haplotype and mutational analysis (10-13).

Several Idd loci have been identified on mouse chromosome 6. (14-16). Recently, the IDDM associated loci Idd6, Idd19, and Idd20 on distal chromosome 6 have been further defined by the analysis of a series of congenic strains, carrying C3H/HeJ genomic material for distal chromosome 6 introgressed onto the NOD/Lt genetic background, with their candidate regions being refined respectively to 4.5, 7 and 4 cM (17).

NOD/Lt alleles at the Idd6 locus on distal mouse chromosome 6 confer susceptibility to IDDM, whilst C57BL/6, C57BL/10 and C3H/HeJ alleles all confer resistance to diabetes (14, 17, 18). The NOD.C3H congenic strain described in this study carries NOD alleles at both the Natural Killer gene complex (18) and the candidate region for the islet-specific BDC-6.9 autoantigen gene (19), which excludes both these loci as responsible for the disease resistance. The Idd6 candidate region does however overlap with the candidate region for the resistance of immature T-cells to dexamethasone (20-22). Idd6 has also been suggested to control low rates of proliferation in immature NOD-thymocytes (23).

Recently we have undertaken a detailed phenotypic analysis of the Idd6 locus containing congenic strain NOD.C3H 6.VIII (17), which shows resistance to the spontaneous development of diabetes. We have shown that this resistance is not ascribable to the resistance of islet β-cells to immune destruction or to a default in pathogenic T cells. Protection of the congenic strain likely involves changes in the proportions of the various leukocyte subsets infiltrating the pancreatic islet, and in particular that of $CD4^+$ T cells. Critical to our understanding of the reduced diabetes susceptibility of the Idd6 congenic mice has been our finding that their splenocytes conferred enhanced disease protection in diabetes transfer assays (24).

However, heretofore, there remained a critical need for the identification of specific genes that control and/or regulate type 1 or insulin dependent diabetes. Additionally, heretofore, there remained a critical need for the identification and development of safe therapeutics for treating or preventing type 1 or insulin dependent diabetes.

SUMMARY OF THE INVENTION

To address the aforementioned critical needs, in the present application the inventors describe the transcriptional profiling of all identified transcripts within the Idd6 interval of the murine model system. A total of six transcripts distributed throughout the interval were found to have strongly altered expression profiles when comparing splenic tissues of the disease protected congenic NOD.C3H 6.VIII and a NOD control strain. Analysis of newly created subcongenic strains showed the presence of at least three diabetes related sub-loci within the Idd6 locus. The recently identified control of disease protection mediated splenocytes was mapped to a 700 kb interval, which contains the Aryl hydrocarbon receptor nuclear translocator-like 2 (Arntl2, Bmal2) encoding gene. This candidate gene was strongly upregulated in the NOD.C3H 6.VIII congenic strain and exhibited a large number of sequence polymorphisms and alternative splice variants. Arntl2 upregulation correlated with the upregulation of the ARNT-binding site containing Pla2g4a gene that has recently been shown to be required for protection against insulitis progression and autoimmune diabetes development. Accordingly, the present invention targets Arntl2 and its downstream targets for controlling type 1 diabetes resistance.

It is an object of the present invention to provide a method of determining the susceptibility of a subject to developing insulin-dependent diabetes by:

a) acquiring a sample from the subject;

b) determining the expression level of the Arntl2 gene in the sample;

c) comparing the expression level of the Arntl2 gene determined in (b) with that of the average expression level of the Arntl2 gene in samples of the corresponding type obtained from the population to which the subject belongs, wherein an expression level of the Arntl2 gene in the subject that is lower than that of the average expression level of the Arntl2 gene is correlated with an increased susceptibility in developing insulin-dependent diabetes.

Another object of the present invention is to provide a method for identifying a compound effective for treating or preventing insulin-dependent diabetes in a subject in need thereof by:

a) acquiring a control sample from a diabetes-sensitive NOD mouse;

b) determining the expression level of the Arntl2 gene in the control sample;

c) administering at least one candidate compound to the diabetes-sensitive NOD mouse;

d) acquiring a test sample from the diabetes-sensitive NOD mouse;

e) determining the expression level of the Arntl2 gene in the test sample; and e) comparing the expression level of the Arntl2 gene determined in (b) with that determined in (e), wherein an increase in the expression level of the Arntl2 gene in (e) as compared to (b) is correlated with an increase in insulin-dependent diabetes resistance.

It is yet another object of the present invention to provide a method of treating insulin-dependent diabetes in a subject in need thereof by administering an effective amount of a composition containing the compound identified by the method above.

Another object of the present invention to provide a method of preventing insulin-dependent diabetes in a subject in need thereof by administering an effective amount of a composition containing the compound identified by the method above.

It is still another object of the present invention to provide a method of enhancing protection against insulitis progression or autoimmune diabetes development in a subject in need thereof by enhancing expression of the Arntl2 gene in cells of the subject.

It is yet another object of the present invention to provide a method of enhancing protection against insulitis progression or autoimmune diabetes development in a subject in need thereof comprising modulating expression of a target gene of the Arntl2 gene in cells of the subject. Within this object, the target genes may be one or more of Pla2g4a, Gpx, Chi3l3, and Mpo.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

FIG. 11 shows the SNPs and Indels of mBmal2. The sequence depicted as "Query" is SEQ ID NO: 35 and the sequence depicted as "Sbjct" is SEQ ID NO: 36.

FIGS. 12A-B shows the Bmal2 coding region. NOD control is shown in SEQ ID NO: 33, while 6.VIII is shown in SEQ ID NO: 34.

FIGS. 13A-D shows the designation of the intron and exon portions of the genomic sequence. FIG. 13A: 071-E1 (118F-668R)-3 SNP (Ensembl Chr.6 147727278 to 147727780), Exon: underlined; NOD control is shown in SEQ ID NO: 37, while 6.VIII is shown in SEQ ID NO: 38. FIG. 13B: SNP35-38 (SNP35-38-64F+SNP35-38-465R)-1 SNP (Ensembl Chr.6 147746092-147746427); NOD control is shown in SEQ ID NO: 39, while 6.VIII is shown in SEQ ID NO: 40. FIG. 13C: 071-E5 (131F+465R)-5 SNPs (Ensembl Chr.6 147751781 to 147752273) Exon: underlined; NOD control is shown in SEQ ID NO: 41, while 6.VIII is shown in SEQ ID NO: 42. FIG. 13D: 071-SNP 75-80 (114F+440R)-1 SNPs (Ensembl Chr.6 starting from the 3rd base 147758806 to 147759169); NOD control is shown in SEQ ID NO: 43, while 6.VIII is shown in SEQ ID NO: 44.

FIG. 14 shows the Bmal2 coding region which marked exons. Bmal2 coding region (SEQ ID NO: 45)—exons marked by different colors (CO as example) Bold: the same exon but with splice forms (The part in bold and underlined is spliced out in mBmal2b sequence resulting in the early stop of translation. The present inventors found the same types of sequences in NOD and 6.VIII.) Underline and and italics with underline: the alternative exons of 6.VIII Italics: the alternative exons of NOD control.

FIGS. 15A-B shows the Sequencing files (071-43F to 071-2122R) corresponding to Bmal2c. More specifically, these figures show the sequencing data corresponding to Bmal2c by amplification using SEQ ID NO: 31 as the forward primer and the reverse complement of SEQ ID NO: 32 as the reverse primer. Bmal2c was cloned into a pGEM-T vector. The coding region is underlined. NOD control (FIG. 15A) is shown in SEQ ID NO: 46 with the encoded polypeptide appearing as SEQ ID NO: 47, while 6.VIII (FIG. 15B) is shown in SEQ ID NO: 48 with the encoded polypeptide appearing as SEQ ID NO: 49.

FIG. 16 shows the 3' UTR (right after the stop codon), the first base corresponds to Ensembl v37 chr.6 147759660. NOD control is shown in SEQ ID NO: 50, while 6.VIII is shown in SEQ ID NO: 51.

FIGS. 17A-D shows the upstream genomic sequence (primers: 071-16798F+071-17695R). FIG. 17A: Upstream genomic sequence (primers: 071-16798F+071-17695R)-4 SNPs (6.VIII sequence blast to Ensembl Chr.6: starting from the 100st base to the end 147715903 to 147716583- did not see the result of 1-99); NOD control is shown in SEQ ID NO: 52, while 6.VIII is shown in SEQ ID NO: 53. FIG. 17B: Upstream genomic sequence (primers: 071-17610F-18412R)-5 SNPs (Ensembl Chr.6 147716616 to 147717298); NOD control is shown in SEQ ID NO: 54, while 6.VIII is shown in SEQ ID NO: 55. FIG. 17C: Upstream genomic sequence (primers: 071-18235F-19236R)-2 SNPs (The $1^{st}$ base=Ensembl Chr.6 147717274- the sequence has been broken to several pieces in the blast result); NOD control is shown in SEQ ID NO: 56, while 6.VIII is shown in SEQ ID NO: 57. FIG. 17D: Upstream genomic sequence (primers: 071-19129F+071-19896R)-6SNPs (The $24^{th}$ nt to the end=Ensembl Chr.6 147718263 to 147718817); NOD control is shown in SEQ ID NO: 58, while 6.VIII is shown in SEQ ID NO: 59.

DETAILED DESCRIPTION OF THE INVENTION

Figure 1:
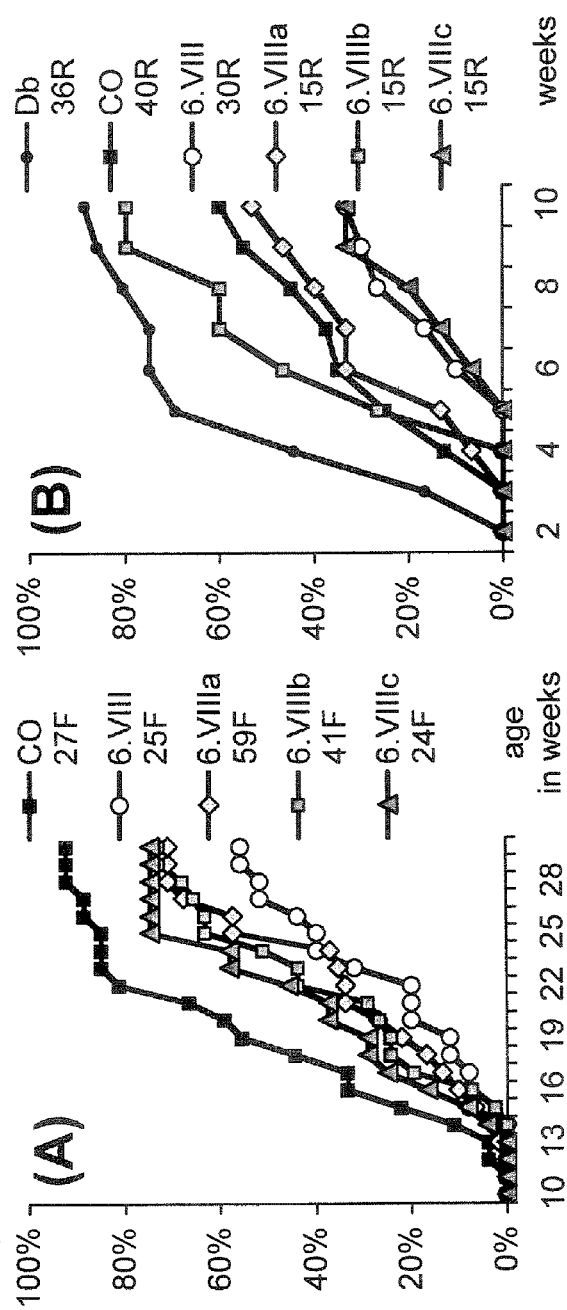
FIG. 1 shows genotyping using a large marker panel for distal chromosome 6, which permits estimation of the size of the C3H derived intervals. (A) Cumulative incidence of different mouse strains and (B) diabetes protection in splenocyte co-transfer. P-values are <0.0001 for 6.VIII, <0.0001 for 6.VIIIa, 0.01 for 6.VIII c, 0.026 for 6.VIIIc against CO in diabetes incidence; 0.012 for 6.VIII, 0.568 for 6.VIIIa, 0.339 for 6.VIIIb, and 0.048 for 6.VIIIc against CO, and <0.0001 for CO against diabetogenic splenocytes (Db) in diabetes transfer assay.

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The Idd6 murine type 1 diabetes locus has been shown to control diabetes by regulating the protective activity of the peripheral immune system as demonstrated by diabetes transfer assays using splenocytes. The analysis of three novel subcongenic NOD.C3H strains has confirmed the presence of at least two diabetes related genes within the 5.4 Mb Idd6 interval with the disease protection conferred by splenocyte co-transfer being located to a 700 kb subregion. This subinterval contains the circadian rhythm related transcription factor Arntl2 (Bmal2), a homologue of the type 2 diabetes associated ARNT (HIF1β) gene. As shown in the Examples herein, Arntl2 exhibited a six-fold upregulation in spleens of the NOD.C3H 6.VIII congenic strain compared to the NOD control strain, strain-specific splice variants and a large number of polymorphisms in both coding and non-coding regions. Arntl2 upregulation was not associated with changes in the expression levels of other circadian genes in the spleen, but did correlate with the upregulation of the ARNT-binding motif containing Pla2g4a gene, that has recently been described as being protective for the progression of insulitis and autoimmune diabetes in the NOD mouse. The present application provides that the HIFβ-homologous Arntl2 gene is involved in the control of type 1 diabetes.

Both others and we have previously shown that the immune system, notably spleen and thymus, are required for Idd6 mediated disease susceptibility in the NOD mouse. In the present application a systematic transcriptional profiling approach to genes located within the candidate region for the murine type 1 diabetes locus Idd6 is described. In a comparison of the disease protected NOD.C3H congenic strain 6.VIII to its NOD control strain, six genes were found to be differentially expressed in the spleen. We mapped the subphenotype of diabetes disease protection in splenocyte co-transfer assays to a restricted interval of 700 kb by analysis of three newly created NOD.C3H congenic strains. Whilst this region (Idd6.3) contains ten transcripts, only the bHLH-PAS transcription factor superfamily member Arntl2 (Bmal2), a component of the circadian clock pathway, was found to be differentially expressed in the disease protected 6.VIII strain.

Arntl2 contains a large number of NOD/C3H polymorphisms within the 5'UTR, exonic, and 3'UTR sequences of its transcript. Several polymophisms in Arnt2 will lead to changes in its functional domains, and could be expected to influence its dimerization, transcriptional activity and/or specificity. In addition, putative alternative strain-specific splice forms were identified. It has previously been suggested that such alternative splicing of ARNTL2 (BMAL2) might provide tissues with a rheostat capable of regulating CLOCK: BMAL2 heterodimer function across a broad continuum of potential transcriptional activities, and that this might be important in accommodating a variety of metabolic demands and physiological roles (36).

In the Examples of the present application, it is shown that changes in Arntl2 transcript levels are not associated with widespread generalized changes in the expression levels of other circadian and hypoxia-induced genes in spleen. The BMAL-CLOCK heterodimers are however known to activate E-box element-dependent transcription (27) and our microarray analysis and quantitative RT-PCR on spleen samples have revealed the Cytosolic phospholipase A(2)alpha (cPLA(2) alpha), which contains an ARNT binding motif, as a potential downstream target of Arntl2. The Cytosolic phospholipase A(2)alpha (cPLA(2)alpha, Pla2g4a) gene is known to play an important role in arachidonate pathway. Non-obese diabetic (NOD) mice deficient in cPLA(2)alpha show severe insulitis and an increased incidence of diabetes. In the macrophages of these knockout mice, prostaglandin E(2) (PGE(2)) production is decreased and tumour necrosis factor (TNF)-alpha production is increased. Overall the results suggest that cPLA (2)alpha plays a protective role in the progression of insulitis and the development of autoimmune diabetes via suppression of TNF-alpha production from macrophages (37). This observation correlates with our finding that peritoneal macrophages of pre-diabetic 6.VIII mice show a 2.8 fold decrease in Tnf-alpha expression (unpublished data), data that could suggest that Arntl2 may be involved in the control the Tnf-alpha pathway in macrophages of 6.VIII mice.

A more precise understanding of how the upregulation and polymorphisms of the widely expressed Arntl2 gene in the 6.VIII strain interact in the regulation of different aspects of the immune system will benefit from additional studies, in particular as it can be expected that the role of Arntl2 may vary from tissue to tissue and between cell types. For example, it is possible to identify and characterize tissue-specific splice variants that effectuate enhanced effects. In relation with previously described phenotypes for Idd6 whose alleles appear to be involved in the regulation of proliferation and apoptosis in the thymus (22, 23), it is important to note that Arntl2 downregulation was found to enhance cell proliferation (26). Another study has identified Arntl2 as being differentially expressed in various $CD4^+CD25^+$ regulatory T cell subpopulations (38). This finding is of interested because $CD4^+CD25^+$ T cell activity has been found to be modulated by Idd6 alleles (24).

Of particular interest is recent data showing that a homologue of Arntl2, ARNT (HIF1β) is associated with type 2 diabetes in both human and mouse and as being essential for normal pancreatic beta cell function and insulin production (39, 40). ARNT, also known as the Hypoxia-Inducible Factor 1, heterodimerizes with both BMAL1 and BMAL2 to regulate gene transcription. These and our data implicating Arntl2 in type 1 diabetes in the mouse suggest some communality of genetic and molecular pathways of type 1 and type 2 diabetes, and that ARNT like genes may set the clock for mechanisms of disease protection.

In view of the foregoing, the present invention provides a method of diagnosing the susceptibility of a subject to developing insulin-dependent diabetes by:
a) acquiring a sample from said subject;
b) determining the expression level of the Arntl2 gene in said sample;
c) comparing the expression level of the Arntl2 gene determined in (b) with that of the average expression level of the Arntl2 gene in samples of the corresponding type obtained from the population to which said subject belongs, wherein an expression level of the Arntl2 gene in said subject that is lower than that of the average expression level of the Arntl2 gene is correlated with an increased susceptibility in developing insulin-dependent diabetes.

Within this embodiment, any mammal may be used as the subject. Examples of mammals suitable for use in the present invention include humans, rats, and mice.

In this embodiment, it is preferred that the Arntl2 gene is at least 70% homologous, preferably at least 80% homologous, more preferably at least 90% homologous, and most preferably at least 95% homologous to the sequence of SEQ ID NO: 3. Further, it is preferred that the Arntl2 gene encodes a protein that is at least 70% homologous, preferably at least 80% homologous, more preferably at least 90% homologous, and most preferably at least 95% homologous to the sequence of SEQ ID NO: 4. Still further, it is preferred that the Arntl2 gene product possess aryl hydrocarbon receptor nuclear translocator activity.

In this embodiment, the term "% homologous" includes "% similarity" and "% identity". Incidentally, it is preferred that the Arntl2 gene is at least 70% identical, preferably at least 80% identical, more preferably at least 90% identical, and most preferably at least 95% identical to the sequence of SEQ ID NO: 3. Further, it is preferred that the Arntl2 gene encodes a protein that is at least 70% identical, preferably at least 80% identical, more preferably at least 90% identical, and most preferably at least 95% identical to the sequence of SEQ ID NO: 4. Still further, it is preferred that the Arntl2 gene product possess aryl hydrocarbon receptor nuclear translocator activity.

Since the Arntl2 gene is found to be ubiquitously expressed (see, for example, Schoenhard et al, Am. J. Physiol Cell Physiol. 2002 July; 283(1):C103-114), within this embodiment, the sample may be obtained from one of several sources. These sources include many other body tissues and/or cells. Particular exemplary cell types include: mucosa, spleen, thymus, blood, and pancreas. The skilled artisan would know how to and would select the most appropriate source for the samples for use in the methods of the present invention.

Preferably, the sample contains at least one type of cells selected from the group consisting of CD4(+) T cells, CD8(+) T cells, B cells, and macrophages. In an aspect of this embodiment, the sample is obtained from the spleen.

Within this embodiment, the sample may be acquired by conventional techniques that are readily known to the skilled artisan. For example, the sample may be obtained by tissue biopsy, a blood sample, or a mucosa sample.

The determination method of the expression level of the Arntl2 gene may be achieved by any known method. For example, it is possible to quantitate the amount of Arntl2 transcripts by quantitative PCR techniques using primers designed based upon the known sequence of the Arntl2 gene. The artisan is referred to Current Protocols in Molecular Biology, Ausubel, et al., Eds., Greene Publishing and Wiley-Interscience, New York (2000), among other well known treatises for a discussion of standard PCR protocols. Other quantitation techniques that may be used to effectuate the expression level determination include ELISA and/or Western blot techniques.

Within this embodiment, the expression level of the Anrtl2 gene of the candidate subject is compared to that of the average expression level of the Arntl2 gene in splenic samples of the corresponding type (i.e., where the sample from the subject is acquired from the spleen the comparative expression level would be from spleen, etc.) obtained from the population to which said subject belongs. It is also envisioned in the present invention that the sample may be from a variable source (e.g., thymus, spleen, pancreas, blood, mucosa, etc.) while the comparative expression level is that for a known standard source (e.g., blood).

To this end, the basal expression level for each individual member of the population may be obtained via the same procedure as that of the candidate subject. Following collection of a representative number of members in the population to which the candidate subject belongs an average expression level is determined to which the expression level of the candidate subject can be compared. Within this embodiment, it is preferred that the representatives of the population be clinically screened as to their type 1 diabetes status so as to ensure an unbiased population.

As set forth in the Examples of the present application, in subjects that are resistant to diabetes the expression level of the Arntl2 gene is significantly higher than that found in diabetes-sensitive subjects. As such, where the expression level of the Arntl2 gene in the candidate subject is lower than that of the average expression level of the Arntl2 gene this decreased expression may be correlated to an increased susceptibility in developing insulin-dependent diabetes.

In another embodiment of the present invention is a method for identifying a compound effective for treating or preventing insulin-dependent diabetes in a subject in need thereof by:

a) acquiring a control sample from a diabetes-sensitive NOD mouse;

b) determining the expression level of the Arntl2 gene in said control sample;

c) administering at least one candidate compound to said diabetes-sensitive NOD mouse;

d) acquiring a test sample from said diabetes-sensitive NOD mouse after said administering;

e) determining the expression level of the Arntl2 gene in said test sample; and e) comparing the expression level of the Arntl2 gene determined in (b) with that determined in (e), wherein an increase in the expression level of the Arntl2 gene in (e) as compared to (b) is correlated with an increase in insulin-dependent diabetes resistance.

In this embodiment, it is preferred that the Arntl2 gene is at least 70% homologous, preferably at least 80% homologous, more preferably at least 90% homologous, and most preferably at least 95% homologous to the sequence of SEQ ID NO: 1. Further, it is preferred that the Arntl2 gene encodes a protein that is at least 70% homologous, preferably at least 80% homologous, more preferably at least 90% homologous, and most preferably at least 95% homologous to the sequence of SEQ ID NO: 2. Still further, it is preferred that the Arntl2 gene product possess aryl hydrocarbon receptor nuclear translocator activity.

In this embodiment, the term "% homologous" includes "% similarity" and "% identity". Incidentally, it is preferred that the Arntl2 gene is at least 70% identical, preferably at least 80% identical, more preferably at least 90% identical, and most preferably at least 95% identical to the sequence of SEQ ID NO: 1. Further, it is preferred that the Arntl2 gene encodes a protein that is at least 70% identical, preferably at least 80% identical, more preferably at least 90% identical, and most preferably at least 95% identical to the sequence of SEQ ID NO: 2. Still further, it is preferred that the Arntl2 gene product possess aryl hydrocarbon receptor nuclear translocator activity.

In a preferred aspect of this embodiment, the control sample is obtained from the spleen of the diabetes-sensitive NOD mouse. Preferably, the control sample contains at least one type of splenic cells selected from the group consisting of CD4(+) T cells, CD8(+) T cells, B cells, and macrophages. Alternatively, it is possible that the foregoing control sample may be obtained from the thymus, pancreas, a blood sample, or a mucosa sample of the diabetes-sensitive NOD mouse.

In a preferred aspect of this embodiment, the test sample is obtained from the spleen of the diabetes-sensitive NOD mouse. Preferably, the test sample contains at least one type of splenic cells selected from the group consisting of CD4(+) T cells, CD8(+) T cells, B cells, and macrophages. Alternatively, it is possible that the foregoing test sample may be obtained from the thymus of the of the diabetes-sensitive NOD mouse. In addition, the test sample may be obtained from other tissue and/or cell sources, such as the pancreas. In addition to a tissue biopsy, the sample may also be acquired from a blood sample or a mucosa sample.

Within this embodiment, the sample may be acquired by conventional techniques that are readily known to the skilled artisan. For example, the sample may be obtained by tissue biopsy, a blood sample, or a mucosa sample.

The determination method of the expression level of the Arntl2 gene may be achieved by any known method. For example, it is possible to quantitate the amount of Arntl2 transcripts by quantitative PCR techniques using primers designed based upon the known sequence of the Arntl2 gene. Examples of suitable PCR primers include the primer pairs represented by SEQ ID NO: 11 (071-248F) and SEQ ID NO: 12 (071-334R) or SEQ ID NO: 13 (AY-56F) and SEQ ID NO: 14 (AY-136R). Additional primers suitable for use are the primer pair: 071-43F -GGGAGGATTGTTAGCACGTCT-GTGA (SEQ ID NO: 31) and 071-2122R —the reverse and complementary sequence of 5'-CACTGTACTCTTGAG-CACTGTATTG-3' (SEQ ID NO: 32).

The artisan is referred to Current Protocols in Molecular Biology, Ausubel, et al., Eds., Greene Publishing and Wiley-Interscience, New York (2000), among other well known treatises for a discussion of standard PCR protocols. Other quantitation techniques that may be used to effectuate the expression level determination include ELISA and/or Western blot techniques.

As set forth in the Examples of the present application, in subjects that are resistant to diabetes the expression level of the Arntl2 gene is significantly higher than that found in diabetes-sensitive subjects. As such, where the expression level of the Arntl2 gene in the test sample as compared to the control sample has increased due to contact with the candidate compound(s), the increased expression level of the Arntl2 gene may be correlated with an increase in insulin-dependent diabetes resistance.

In the context of the present invention a difference in expression level is considered to be "significant" when it is a reproducible and noticeable and/or measurable difference. More preferably, the term "significant" refers to a statistically significant difference. As the skilled artisan would appreciate, statistically significance can be determined by any conventional statistical analysis method. The difference is considered statistically significant when the p-value is 5%, more preferably 1%, and most preferably 0.1%.

Within this embodiment, the candidate compound(s) is not particularly limited. It is envisioned that in the present invention the candidate compound(s) may be a drug, a polynucleotide, a polypeptide, immunogenic fragments of polypeptides, a hormone, etc. or a salt thereof. Further, within this embodiment there is no particular limitation on the number of compounds that may be simultaneously administered to the subject. In other words, a compound may be separately administered or multiple compounds may be administered sequentially or simultaneously. Further, the compounds may be administered as pharmaceutical compositions containing one or more pharmaceutically acceptable carriers, diluents, excipients, and adjuvants, or mixtures of the same.

Also, the present method is adaptable to determining the effect of a wide range of dosage forms and amounts. Therefore, it is envisioned that the compound(s) may be administered via any route including orally, parenterally, intravenously, intradermally, subcutaneously, or topically, in liquid or solid form.

The time between the administration of the candidate compound(s) and the recovery of a test sample may range from instantaneous to minutes to hours to weeks. Further, the administration may be either a single administration or may include multiple repeated administration events prior to recovery of a test compound. For example, the present invention embraces repeated individual administration events of the same (or different compounds) once hourly, every four to six hours, twice daily, once daily, once weekly, etc.

The phrase "effective for treating a subject having insulin-dependent diabetes" or the term "treating" as used herein means that the administration of the compound(s) results in a reduction of symptoms associated with insulin-dependent diabetes or of at least one disorder induced, caused or mediated by insulin-induced diabetes by at least 10%, preferably at least 25%, more preferably at least 50%, still more preferably at least 75%, even more preferably at least 80%, yet more preferably at least 90%, and most preferably at least 95%.

The phrase "effective for preventing a subject having insulin-dependent diabetes" or the term "preventing" as used herein means that the administration of the compound(s) results in a reduction in the likelihood that a subject with a propensity of developing or believed to be at risk for developing insulin-dependent diabetes will indeed develop insulin-dependent diabetes. Preferably, in the context of the present invention, this phrase means that the administration of the compound(s) results in the elimination of the likelihood or probability that a subject with a propensity of developing or believed to be at risk for developing insulin-dependent diabetes will indeed develop insulin-dependent diabetes.

In another embodiment of the present invention is a method of treating insulin-dependent diabetes in a subject in need thereof by administering an effective amount of a composition containing a compound(s) that was determined to be effective for treating a subject having insulin-dependent diabetes by the method of the foregoing embodiment.

In another embodiment of the present invention is a method of preventing insulin-dependent diabetes in a subject in need thereof by administering an effective amount of a composition containing a compound(s) that was determined to be effective for preventing insulin-dependent diabetes in a subject in need thereof having by the method of the foregoing embodiment.

As used in the present application, the term "subject in need thereof" is used to designate the subject as being one with a recognized need for prophylactic and/or therapeutic treatment of at least one disorder induced, caused or mediated by insulin-induced diabetes. Within this embodiment and the present invention as a whole, the subject may be any mammal, including by not limited to: a human, a rat, and a mouse.

Within this embodiment, there is no particular limitation on the number of compounds that may be simultaneously administered to the subject. In other words, a compound may be separately administered or multiple compounds may be administered sequentially or simultaneously. Further, the compounds may be administered as pharmaceutical compositions containing one or more pharmaceutically acceptable carriers, diluents, excipients, and adjuvants, or mixtures of the same.

Also, the present method is adaptable to a wide range of dosage forms and amounts. Therefore, it is envisioned that the compound(s) may be administered via any route including orally, parenterally, intravenously, intradermally, subcutaneously, or topically, in liquid or solid form.

Within this embodiment, the composition may be administered in single or repeated dosages. For example, the composition may be administered once hourly, every four to six hours, twice daily, once daily, once weekly, etc.

Further, the term "effective amount" is any amount that results in the reduction of symptoms associated with insulin-dependent diabetes or of at least one disorder induced, caused or mediated by insulin-induced diabetes by at least 10%, preferably at least 25%, more preferably at least 50%, still more preferably at least 75%, even more preferably at least 80%, yet more preferably at least 90%, and most preferably at least 95%.

However, it is generally preferred that the nature of the compound and the nature of the administration method and dosage be tailored to that determined to be effective by the above-described identification method.

Yet another embodiment of the present invention is a method of enhancing protection against insulitis progression or autoimmune diabetes development in a subject in need thereof comprising modulating expression of a target gene of the Arntl2 gene in cells of said subject.

Suitable targets within the scope of the present invention include Pla2g4a, Gpx, Chi3l3, and Mpo (see Example 8).

Therefore, in still another embodiment of the present invention is a method of enhancing protection against insulitis progression and/or autoimmune diabetes development in a subject in need thereof by enhancing expression of the Arntl2 gene in the cells of said subject.

This embodiment is based on the observation in the Examples below that Arntl2 upregulation was not associated with changes in the expression levels of other circadian genes in the spleen, but did correlate with the upregulation of the ARNT-binding motif containing Pla2g4a gene, that has recently been described as being protective for the progression of insulitis and autoimmune diabetes in the NOD mouse. The present application provides that the HIFβ-homologous Arntl2 gene is involved in the control of type 1 diabetes. As such, enhancing the expression of the Arntl2 gene in the cells of a subject would be expected to upregulate the expression level of the Pla2g4a gene, which in turn would enhance protection against insulitis progression and/or autoimmune diabetes development.

In accordance with the definition of "subject in need thereof" defined above, within this embodiment, the subject may be any mammal, including but not limited to: a human, a rat, and a mouse.

In this embodiment, it is preferred that the Arntl2 gene is at least 70% homologous, preferably at least 80% homologous, more preferably at least 90% homologous, and most preferably at least 95% homologous to the sequence of SEQ ID NO: 1. Further, it is preferred that the Arntl2 gene encodes a protein that is at least 70% homologous, preferably at least 80% homologous, more preferably at least 90% homologous, and most preferably at least 95% homologous to the sequence of SEQ ID NO: 2. Still further, it is preferred that the Arntl2 gene product possess aryl hydrocarbon receptor nuclear translocator activity.

In this embodiment, the term "% homologous" includes "% similarity" and "% identity". Incidentally, it is preferred that the Arntl2 gene is at least 70% identical, preferably at least 80% identical, more preferably at least 90% identical, and most preferably at least 95% identical to the sequence of SEQ ID NO: 1. Further, it is preferred that the Arntl2 gene encodes a protein that is at least 70% identical, preferably at least 80% identical, more preferably at least 90% identical, and most preferably at least 95% identical to the sequence of SEQ ID NO: 2. Still further, it is preferred that the Arntl2 gene product possess aryl hydrocarbon receptor nuclear translocator activity.

In this embodiment, it is preferred that the Arntl2 gene is at least 70% homologous, preferably at least 80% homologous, more preferably at least 90% homologous, and most preferably at least 95% homologous to the sequence of SEQ ID NO: 3. Further, it is preferred that the Arntl2 gene encodes a protein that is at least 70% homologous, preferably at least 80% homologous, more preferably at least 90% homologous, and most preferably at least 95% homologous to the sequence of SEQ ID NO: 4. Still further, it is preferred that the Arntl2 gene product possess aryl hydrocarbon receptor nuclear translocator activity.

In this embodiment, the term "% homologous" includes "% similarity" and "% identity". Incidentally, it is preferred that the Arntl2 gene is at least 70% identical, preferably at least 80% identical, more preferably at least 90% identical, and most preferably at least 95% identical to the sequence of SEQ ID NO: 3. Further, it is preferred that the Arntl2 gene encodes a protein that is at least 70% identical, preferably at least 80% identical, more preferably at least 90% identical, and most preferably at least 95% identical to the sequence of SEQ ID NO: 4. Still further, it is preferred that the Arntl2 gene product possess aryl hydrocarbon receptor nuclear translocator activity.

As stated above, since the Arntl2 gene is found to be ubiquitously expressed (see, for example, Schoenhard et al, Am. J. Physiol Cell Physiol. 2002 July; 283(1):C103-114), within this embodiment and the present invention as a whole, the sample may be obtained from one of several sources. These sources include many other body tissues and/or cells. Particular exemplary cell types include: spleen, thymus, blood, mucosa, and pancreas.

In an aspect of this embodiment, the sample is obtained from the spleen. Preferably, the sample contains at least one type of splenic cells selected from the group consisting of CD4(+) T cells, CD8(+) T cells, B cells, and macrophages.

Within this embodiment, the sample may be acquired by conventional techniques that are readily known to the skilled artisan. For example, the sample may be obtained by tissue biopsy, a blood sample, or a mucosa sample.

As a means of enhancing expression of the Arntl2 gene, the following methods may be mentioned, but are not intended to be an exhaustive list of suitable methods:
 overexpression by gene therapy;
 administration of specific drugs that inhibit Arntl2 protein degradation;
 therapy to produce a stable form of Arntl2.

As used herein, the term "Arntl2" is used to designate the polynucleotide sequence of SEQ ID NO: 1 obtained from mice and SEQ ID NO: 3 obtained from humans and homologous sequences coding for polypeptides with the same function as the polypeptides shown by SEQ ID NO: 2 or 4. Specifically, the term "Arntl2" is used to designate the open-reading frame, inclusive of exons and introns. However, it is to be recognized that the protein encoded by the Arntl2 gene would constitute only the exonic regions. Where necessary to distinguish, the present application refers to the mouse Arntl2 gene as "mArntl2" and the human Arntl2 gene as "hArntl2."

The present invention also includes polynucleotides that hybridize to the complement of the polynucleotide sequence of Arntl2, or homologs and/or fragments thereof, under stringent conditions.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 5×SSC, preferably 1× to 2×SSC, (20×SSC=3.0 M NaCl/0.3 M trisodium citrate) at 50 to 68° C., preferably 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA--DNA hybrids, the Tm can be approximated from the equation of Meinkoth and Wahl, Anal. Biochem., 138:267-284 (1984): $Tm=81.5°$ $C.+16.6 (\log M)+0.41 (\% GC)-0.61 (\% form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

In the context of the present invention, a polynucleotide sequence is "homologous" with the sequence according to the invention if at least 70%, preferably at least 80%, more preferably at least 90%, most preferably at least 95% of its base composition and base sequence is identical to the sequence according to the invention (i.e., Arntl2).

Another object of the present invention are the polypeptide sequences encoded by Arntl2, or a homolog thereof. The polypeptides of the present invention exhibit aryl hydrocarbon receptor nuclear translocator activity.

According to the invention, a "homologous protein" or "homologous polypeptide" is to be understood to comprise proteins (polypeptides) which contain an amino acid sequence at least 70% of which, preferably at least 80% of which, more preferably at least 90%, most preferably at least 95% of which corresponds (i.e., is identical and/or similar) to the amino acid sequence encoded by Arntl2. It is particularly preferred that the homologous protein retain at least 50%, preferably at least 70%, more preferably at least 80%, most preferably at least 90% of the residual activity of the wild-type hydrocarbon receptor nuclear translocator activity. The homologous proteins embrace homologous and non-homologous amino acid substitutions, as well as polymorphs and alternative spliced variants.

The expression "homologous amino acids" denotes those that have corresponding properties, particularly with regard to their charge, hydrophobic character, steric properties, etc.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores. Sequence alignments can also be performed using the Align.ppc program (Mac Molly TetraLite, Mologen) or ClustalW.

One skilled in the art is also aware of conservative amino acid replacements such as the replacement of glycine by alanine or of aspartic acid by glutamic acid in proteins as "sense mutations" which do not result in any fundamental change in the activity of the protein, i.e. which are functionally neutral. It is also known that changes at the N- and/or C-terminus of a protein do not substantially impair the function thereof, and may even stabilize said function.

The term "isolated" means separated from its natural environment.

The term "polynucleotide" refers in general to polyribonucleotides and polydeoxyribonucleotides, and can denote an unmodified RNA or DNA or a modified RNA or DNA. Further, this term embraces recombinant polynucleotides. Of course, this term also embraces salt forms thereof.

The term "polypeptides" is to be understood to mean peptides or proteins that contain two or more amino acids that are bound via peptide bonds. Further, this term embraces recombinant polypeptides. Of course, this term also embraces salt forms thereof.

The present inventors have sequenced the murine gene Arntl2 in the NOD/Lt and C3HHeJ strains and identified polymorphisms between the diabetes sensitive strain NOD/Lt and the diabetes resistant strain C3HHeJ (see Example 6 and FIGS. 8-17). These polymorphs form a part of the present invention. The reference sequence NM_172309 refers to the diabetes-resistant C57BL/6J strain. It should be noticed that the present inventors have also identified alteration of transcription levels of Arntl2, which is upregulated in the diabetes resistant congenic NOD.C3H 6.VIII.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Material and Methods
RNA Preparation, cDNA Synthesis and Microarray Analysis—

Total RNA was prepared using RNABle (Eurobio). Random cDNA synthesis was carried out on 6 µg DNAseI treated total RNA using SuperScript™ II reverse transcriptase (Invitrogen) according to the manufacturer's conditions. For microarray experiments, RNA quality was examined using an Agilent 2100 Bioanalyser (Agilent). DNA-microarrays (8k mouse cDNA, Agilent) were hybridised using 10 µg of total RNA transcribed in the presence of Cy3-dCTP or Cy5-dCTP, respectively. Data were from four individual experiments, each including a dye swap, were analysed using Feature Extraction and Rosetta resolver software (p<0.05) and annotated using SOURCE software (provided by the Genetics Department, Stanford University).

Northern Blot and RACE Experiment—

Total RNA of various tissues from the 6.VIII and NOD control strains was separated in TBE on 1% agarose gels containing 1% formaldehyde and transferred on Hybond N+ membranes (Amersham). Northern blots were hybridized using a 3' NOD cDNA fragment amplified with the Arntl2 specific primers AY-555F 5'-AGGCAACACCAGAG-CACTGA-3' (SEQ ID NO: 5) and AY334R 071-334R 5'-GC-CAGGATTACAAAGTGTGCAC-3' (SEQ ID NO: 6). 5' and 3' RACE experiments were performed using both total spleen RNA extracted from NOD CO and 6.VIII strain and the GeneRacer Kit (Invitrogen).

Quantitative PCR—

Quantitative PCR was performed on an ABIPRISM 7700 Sequence detector using the SYBR Green PCR Master Mix (PE Biosystems) according to the manufacturer's conditions. Primers were designed using PrimerExpress software and used at optimal concentration. Quantification of the amplification product was carried out using the Standard curve method. For the circadian rhythm analysis we used the ΔCT method and the Gapdh gene expression as reporter. Sequences of the oligonucleotides used were as follows:

| Gene | Primer name | primer sequence | |
|---|---|---|---|
| Bcat1 | 030-263F | GGAGTGACCAGGCAGAGCA | (SEQ ID NO: 7) |
| | 030-344R | CATCCATGGTGAGGTGTCTCTC | (SEQ ID NO: 8) |
| Las1 | 032-138F | CTGTGACCTTGATTCAGGATGC | (SEQ ID NO: 9) |
| | 032-218R | GGACTTTGTTCATGCCACAGG | (SEQ ID NO: 10) |
| Arntl2 | 071-248F | GGTGACAGAGTCCTTGCCTAGC | (SEQ ID NO: 11) |
| | 071-334R | GCCAGGATTACAAAGTGTGCAC | (SEQ ID NO: 12) |
| | AY-56F | GTGGCTATGGGACGGTTGC | (SEQ ID NO: 13) |
| | AY-136R | AGTTATGAACTCAGCCGGTCTCA | (SEQ ID NO: 14) |
| BE647206 | 082-258F | TGAAGAAAAGCAGCCTTCCTTAG | (SEQ ID NO: 15) |
| | 082-338R | GGTAGGCACGTCCATTAAGGAG | (SEQ ID NO: 16) |
| Mlstd1 | 098-660F | AAAGCCTTGGGAGAGATAGTAGTGC | (SEQ ID NO: 17) |
| | 098-740R | TGCTCCCACTATGGATGGC | (SEQ ID NO: 18) |
| mCG1027210 | 106-497F | GGTCGTTCATCCTCAGTCCAC | (SEQ ID NO: 19) |
| | 106-578R | TGCAGGTGTGAAGTTTTATATCCAG | (SEQ ID NO: 20) |
| Arntl1 | mBmal1-224F | GCCCAAAGAGGACTCATCCC | (SEQ ID NO: 21) |
| | mBmal1-304R | CGATCATTCGACCTATTTTTCCTG | (SEQ ID NO: 22) |
| Per1 | mPer1-377F | TATTCCCTACCCCACCTAGTTATCC | (SEQ ID NO: 23) |
| | mPer1-460 | AGGGCGAGTGGGAAGCAG | (SEQ ID NO: 24) |
| PAI-1 | PAI-147F | GTCTGCATCCCTGTATGTCAGG | (SEQ ID NO: 25) |
| | PAI-236R | CCACTAGGCGGCAGTGTGA | (SEQ ID NO: 26) |
| Pla2g4a | 2329F | TCGTTGCTCTGTTTCCCTCA | (SEQ ID NO: 27) |
| | 2425R | ATCATCCCAGCACAGAAATTACAC | (SEQ ID NO: 28) |
| Gapdh | GAPDH-RT-F | TGCACCACCAACTGCTTAG | (SEQ ID NO: 29) |
| | GAPDH-RT-R | GATGCAGGGATGATGTTC | (SEQ ID NO: 30) |

Sequence Analysis—

DNA fragments were amplified and sequenced from genomic DNA or cDNA of the NOD.C3H strain 6.VIII and the NOD control mice. Polymporphisms were identified by sequence alignment using Megalign (DNASTAR Inc.). Potential transcription factor binding sites were identified by using the MatInspector program, which is available from Genomatix Software GmbH (Munich, Germany) (41).

Construction of Mouse Strains—

The subcongenic strains were constructed by intercrossing the Idd6 congenic NOD.C3H 6.VIII strain (6.VIII) and the NOD control congenic strain (CO), both originally derived from crosses between C3H/HeJ and NOD/Lt mice (17). Male mice heterozygous for the Idd6 interval were then backcrossed to the CO strain. Recombinant offspring were selected using the polymorphic markers D6Mit14, D6Mit15, D6Mit294 and D6Mit304. The corresponding subcongenic intervals were fixed by intercrossing of the heterozygous offspring resulting from a backcross to the CO strain.

Diabetes Assessment and Transfer Assays—

Spontaneous diabetes incidence was monitored weekly from 10 to 30 weeks of age by assessment of glucosuria (Diabur test, Roche). Splenocyte co-transfer was performed by transferring $10^7$ splenocytes from diabetic NOD mice together with $2 \times 10^7$ splenocytes from seven week old mice of various mouse strains onto five week old NOD/Scid mice. Cumulative diabetes incidence was monitored weekly throughout 10 weeks post transfer.

Statistical Analysis—

Statistics were performed by Kaplan-Meier estimation and log-rank test for group comparison. Pooled data from quantitative RT-PCR were compared as mean +/− standard deviation.

Example 1

Refinement of the Idd6 Interval by Haplotype Mapping

The original microsatellite based genotyping of the diabetes-resistant Idd6 congenic strain NOD.C3H 6.VIII (strain 6.VIII) indicated that the C3H introgressed donor sequence was located at the end of chromosome 6, distal to the microsatellite marker D6Mit113 (17, 25). Random sampling of potential SNPs listed in the genomic databases identified four polymorphisms located between bps 144,874,468 and 144, 874,516 on mouse chromosome 6. These SNPs included a SNP at bp position 144,874,516 associated with a silent amino acid exchange in the Sox5 gene, located distal to D6Mit113 (Ensembl mouse database for *Mus musculus*) (Table 1). The mapping of these newly identified SNPs allowed the Idd6 locus to be restrained from a 6.1 Mb to a 5.4 Mb interval lying in between the Sox5 locus and the telomere of mouse chromosome 6.

TABLE 1

Genes that are significantly differentially expressed in the diabetes-resistance strain 6.VIII compared to the diabetes-sensitive NOD mice at 6-7 weeks old of age. Data were pooled from the analysis of three or four pre-diabetic animals showing no signs of insulitis progression. The sequence positions shown are according to the NCBI build m34.

| Gene Name | Position in Chr. 6 (Idd6 subinterval) | Fold change in spleen 6.VIII/CO |
|---|---|---|
| Bcat1 | 145,845,604-145,922,395 (Idd6.2) | −2.1 ± 0.4 |
| Casc1 | 146,021,369-146,057,345 (Idd6.2) | +2.9 ± 0.43 |
| Arntl2 | 147,726,464-147,759,659 (Idd6.3) | +6.7 ± 1.62 |
| BE647206, AW120472 | 148,167,817-148,169,401 (Idd6.1) | +7.2 ± 4.31 |
| Mlstd1 | 148,976,675-149,116,580 (Idd6.1) | +1.5 ± 0.3[a] |
| mCG1027210 | 149,535,041-149,574,578 (Idd6.1) | absent in the NOD strain |

[a]The expression of Mlstd1 in strain 6.VIII at 4 weeks of age is 2.5 fold higher that in NOD mice.

Example 2

Construction and Diabetes Incidence of Subcongenic Strains

In order to further refine the type 1 diabetes associated Idd6 candidate region localising within 4 cM (5.4 Mb) of distal mouse chromosome 6, we constructed a series of subcongenic strains by intercrossing the Idd6 congenic NOD.C3H 6.VIII strain (6.VIII) and the NOD control congenic strain (CO), that were originally derived from crosses between the C3H/HeJ and NOD/Lt mouse strains. Heterozygous male mice resulting from the intercross were then again backcrossed to the CO strain and recombinants were selected amongst the offspring using the polymorphic markers D6Mit14, D6Mit15, D6Mit294 and D6Mit304 (FIG. 1). Out of the 200 BX1 animals that were tested three were found to be recombinants. The corresponding subcongenic intervals were fixed by further backcrossing to the CO strain and by intercrossing of the heterozygous recombinant animals. Genotyping using a large marker panel for distal chromosome 6, as shown in FIG. 1, allowed the estimation of the size of the C3H derived intervals. We noticed that all three breakpoints for recombination were located between the markers D6Mit294 and D6Mit373, suggesting that this region may recombine more frequently than others within the Idd6 interval.

Figure 2:
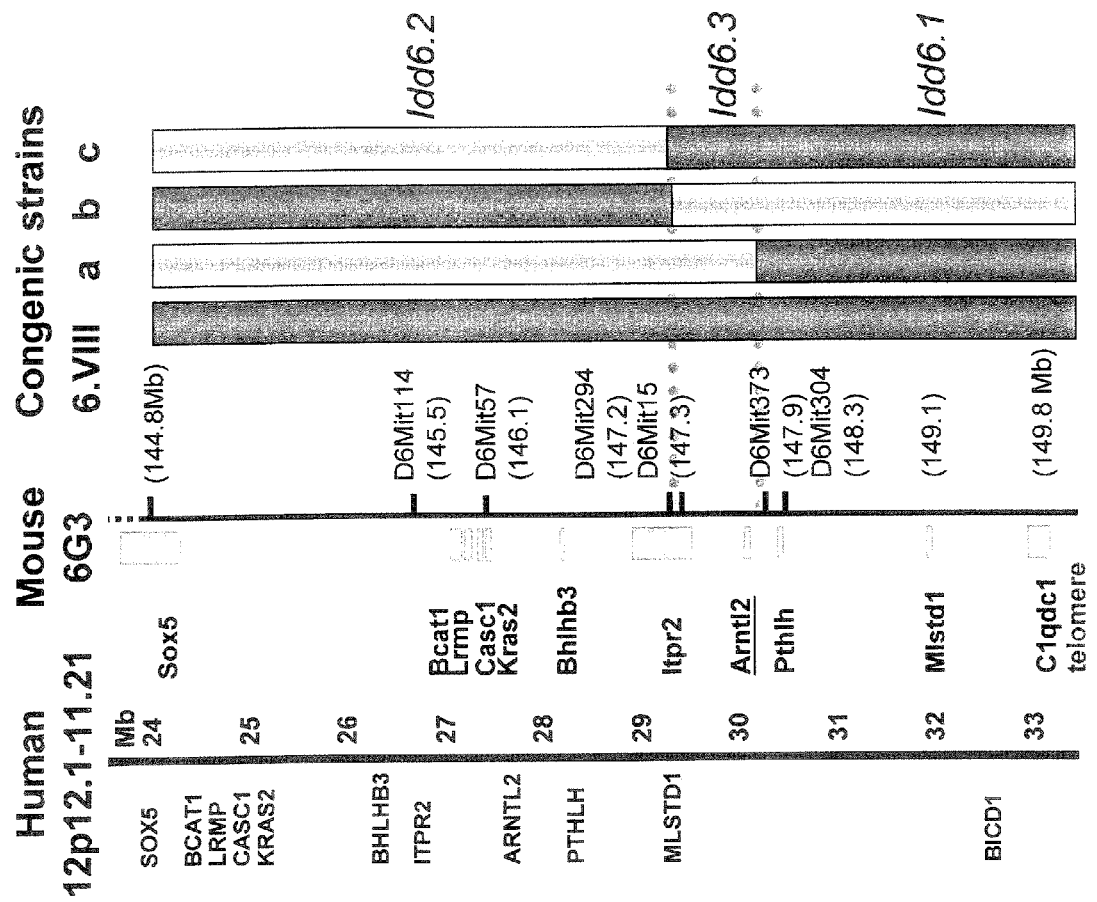
FIG. 2 shows a map of the C3H derived intervals (grey bars) on distal chromosome 6 contained in the original NOD.C3H 6.VIII and new subcongenic mouse strains 6.VIIIa, 6.VIIIb, 6.VIIIc. The localization of the newly defined candidate region for the splenocyte subphenotype (Idd6.3) is indicated by dotted lines. Based on NCBI Human version 35.1 June 2004, Mouse version 34.1 Feb. 28, 2005.

We tested the diabetes incidence weekly for all three subcongenic strains in parallel to the parental strains over a period of 30 weeks (FIG. 2). In female mice, all the newly created strains were protected compared to the CO strain, although each strain was slightly less protected than the 6.VIII strain. Data were similar for male mice, although male mice of each strain developed less diabetes than female mice. This result led us to conclude that at least two intervals (Idd6.1 and Idd6.2) and several genes in the Idd6 region contribute to the overall diabetes protection of the 6.VIII strain (Table 1).

Example 3

Analysis of Inhibition of Diabetes Transfer

We have previously shown that Idd6 modifies suppression of diabetes in co-transfer assays when using splenocytes. We tested whether this splenocyte sub-phenotype segregates with one or other of the newly derived C3H derived sub-intervals. A total of $2\times10^7$ splenocytes from 7 week-old mice were injected into NOD/Scid recipient mice together with $10^7$ total splenocytes from diabetic mice. As expected, injection of the diabetogenic cells alone resulted in the rapid induction of diabetes in the NOD/Scid recipient. Co-transfer of splenocytes inhibited significantly the diabetes transfer in all the groups tested (FIG. 2). As previously described, stronger protection was found with the 6.VIII splenocytes than with CO splenocytes. Similar significant protection was found for strain 6.VIIIc, but not for either strains 6.VIIIa or 6.VIIIb. Strain 6.VIIIc differs from strain 6.VIIIa by only a 700 kb C3H derived interval (Idd6.3) lying between the markers D6Mit294 (147.2 Mb, C3H allele in strain 6.VIIIc, NOD allele in 6.VIIIa) and D6Mit373 (147.9 Mb, C3H allele in both 6.VIIIc and 6.VIIIa).

Example 4

Transcriptional Profiling of Genes in the Idd6 Interval

Diabetes associated genes are expected to be either functional coding sequence variants or to show differential regulation between diabetes sensitive and a diabetes resistant strains. Detection of functional coding variants would require extensive sequencing efforts throughout the entire 5.4 Mb Idd6 candidate interval, which contains some hundred potential genes, which would likely through up a very large number of sequence variants for evaluation. We turned therefore first to expression analysis for the identification of potential candidate genes responsible for the susceptibility to IDDM. Potential mouse transcripts within Idd6 were identified from the Celera and public databases. Additional information was obtained by examination of the syntenic region to Idd6 in the human genome, which maps to the 12p11-p12.2 chromosomal region (NCBI version 35.1, FIG. 1).

Since our previous results had indicated that splenocytes contribute to the disease regulation mediated by Idd6, the expression profiles of potential transcripts in the spleen were examined. Those genes that were expressed in the spleen were then analysed by real time RT-PCR for differential expression in the diabetes-sensitive NOD mice and the diabetic-resistant congenic strain 6.VIII. Spleen samples from both four weeks old and six to seven weeks old mice were chosen in order to capture genes showing differences during the primary stages of disease progression before the onset of overt diabetes. Six transcripts were found to have such differential expression in spleen. These genes were Bcat1, Csac1 (Las1), Arntl2 (Bmal2), a gene of unknown function represented by two EST clones BE647206 and AW120472, Mlstd1 (Msl2), and the predicted transcript mCG1027210 (Celera database) (Table 1).

The 700 kb Idd6.3 interval contains a total of ten genes (FIG. 1, Table 2) with seven transcripts, 4933424B01Rik, Tm7sf3, Stk381, LOC232534, 1700023A16Rik, Ppfib1, and 2210417D09Rik, being unlikely candidates for IDDM because of their known role or inappropriate expression pattern. None of the genes showed however differential expression between the 6.VIII and CO strains except for the Arntl2 (Bmal2) (brain-muscle-ARNT-like protein 2) gene that was six-fold overexpressed in spleens of the 6.VIII strain. We turned therefore to a detailed analysis of Arntl2.

TABLE 2

Candidate genes in the Idd6.3 candidate region. If not otherwise stated, information concerning the expression profile was obtained from the NCBI GEO and the MGI databases.
Names of known genes are indicated in bold.
Transcripts in the Idd6.3 interval
_M. musculus_ Genome (Build 34.1), Chromosome: 6, Map: rna

| start-stop | Accession | Locus | Description |
|---|---|---|---|
| 147470323-147498450 | NM_138757.1 | 4933424B01Rik | RIKEN cDNA 4933424B01 gene strongly expressed in brain and mammary gland |
| 147498626-147519888 | NM_026218 | Fgfr1op2 | FGFR1 oncogene partner 2 ubiquitous, fusion protein associated with myeloproliferative syndrome (42) |
| 147523051-147555191 | NM_026281.1 | Tm7sf3 | Tm7sf3: Transmembrane 7 superfamily member 3 highly in diencephanlon; mainly kidney expressed (43) |
| 147563270-147571291 | NM_025315.1 | Surb7 | SRB7 (supressor of RNA polymerase B) homolog (_S. cerevisiae_) highest in brain stem; down-regulated in spleen nock-out embryonic lethal (44) |
| 147645809-147699737 | NM_172734.2 | Stk381 | serine/threonine kinase 38 like highly in bladder and olfactory system |
| 147703404-147704208 | XM_620385.1 | LOC232534 | similar to 40S ribosomal protein S2 |
| 147726464-147759659 | NM_172309.1 | Arntl2/Bmal2 | aryl hydrocarbon receptor nuclear translocator-like 2 (see detailed analysis herein) |
| 147777200-147798519 | XM_132958.2 | 1700023A16Rik | RIKEN cDNA 1700023A16 gene male genital specific |
| 147815629-147958590 | NM_026221.1 | Ppfibp1 | PTPRF interacting protein, binding protein 1 (liprin beta 1) RIKEN cDNA 1700034J05 gene absent in lymph nodes and thymus |
| 147959104-147960052 | NM_025620.1 | 2210417D09Rik | RIKEN cDNA 2210417D09 gene intestine and stomac restricted expression |

Example 5

Expression and Transcript Analysis of the Arntl2 Candidate Gene

Figure 3:
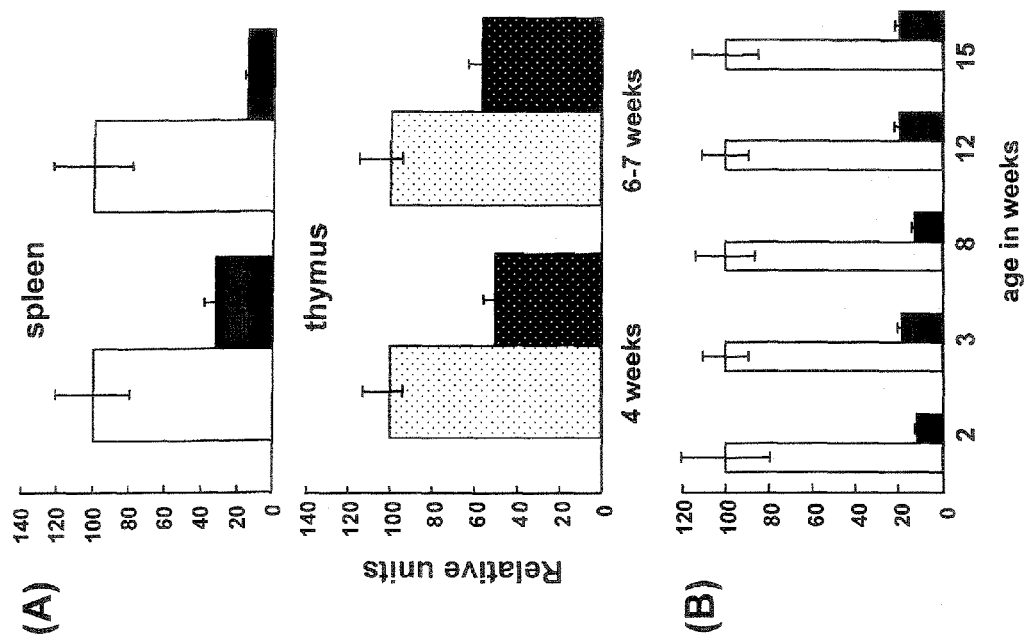
FIG. 3 shows the relative expression of Arntl2 (Bmal2) gene in strain 6.VIII (white bars) and NOD CO mice (black bars) indicated as arbitrary units. Pooled RNA from spleen and thymus of four pre-diabetic female mice (A) and spleen at different ages and 15 weeks old diabetic mice (B) were analysed for the expression of Arntl2 by Q-RT-PCR.

The Arntl2 gene encodes a basic helix-loop-helix-Per-Arnt-Sim (bHLH-PAS) transcription factor and has been functionally linked to circadian clock mediated activities and to the regulation of cell proliferation (26). The Arntl2 gene was expressed in significantly higher amounts in spleen samples obtained from either 4 weeks old or 6-7 weeks old diabetes-resistant strain 6.VIII animals than from diabetes-sensitive NOD mice (FIG. 3A). Thymi obtained from the same groups of animals showed a similar tendency, although with only two-fold difference, between the strain 6.VIII and NOD mice (FIG. 3B). Lymphocyte subsets, including B cells, CD4+ T cells, CD8+ T cells, CD4+CD25+ regulatory T cells showed similar expression differences to the whole tissue preparations. Further expression profiling of spleens showed that differential expression of Arntl2 was independent of the age of the animals and maintained from two to twelve weeks of age as well as in diabetic animals (FIG. 3C). These results suggest that the differential expression of Arntl2 in the two mouse strains is independent of disease progression.

Figure 4:
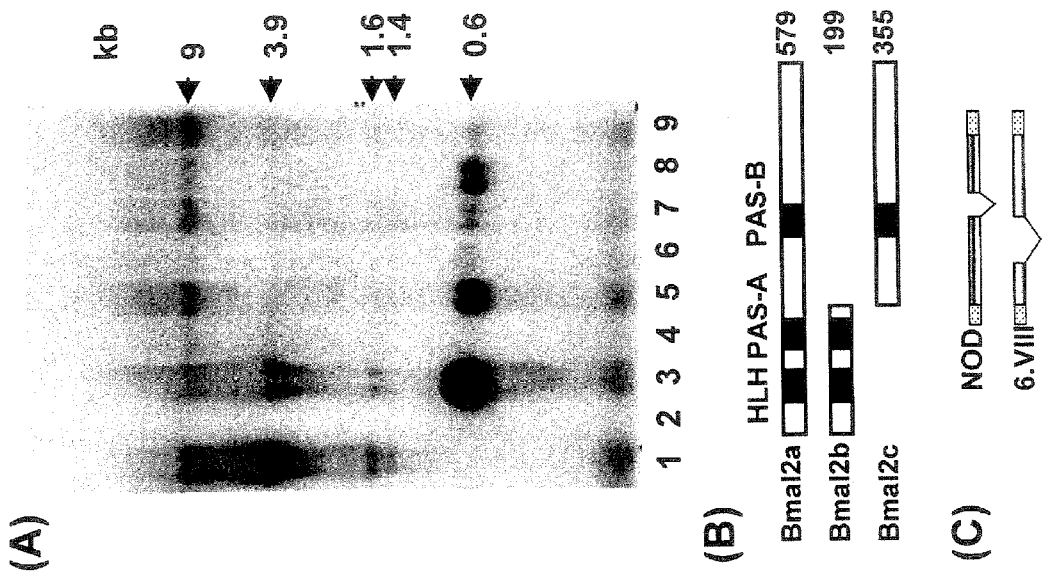
FIG. 4 shows the transcription profile and architecture of Bmal2. (A) Transcript profiles of Bmal in 6.VIII and NOD mice were identical as shown by Northern blotting. 1, thymus; 2, testis; 3, spleen; 4, skeletal muscle; 5, lung; 6, liver; 7, kidney; 8, heart; 9, brain. (B) Three isoforms Bmal2a, Bmal2b, and Bmal2c of 579, 199 and 355 amino acids length, were present in the spleen (bottom). (C) Partial sequences identified in spleen indicate the presence of strain-specific isoforms (top).

The detailed transcript pattern of Arntl2 in multiple tissues was examined in strain 6.VIII and NOD mice. For most of the organs examined such as brain or lung, the major transcripts identified were 9 kb or 0.6 kb in size. The transcript profiles of the spleen and thymus were however surprisingly varied compared to those of other organs, and additional 3.9 kb and 1.6 kb transcripts were found in both spleen and thymus. A 1.4 kb transcript was exclusively found in thymus. The common 0.6 kb transcript, present in most of organs, was not detected in the thymus (FIG. 4). Such complex transcription profiles with transcripts specific to the spleen and thymus may indicate a specific role for the Arntl2 gene in the immune system.

Prior studies have identified two protein products of Bmal2, Bmal2a and Bmal2b (27) containing respectively 579 and 199 amino acids. While examining the transcripts expressed in spleen of strain 6.VIII and NOD CO mice, a third putative alternative spliced variant, Bmal2c, was identified in a 5' RACE experiment. This transcript initiated within an intron, 100 nucleotides upstream of the start of exon 7 in the consensus mRNA (AY005163, Arntl2a mRNA). This transcript encoded a 355 amino acid protein containing only the C-terminal half of the full-length protein and was missing both the bHLH and PAS-A domains (FIG. 4B). All these transcripts were identical between 6.VIII and NOD spleen, but the analysis of partial cDNA sequences amplified from nested primers indicated the existence of transcripts specific for strains 6.VIII and NOD, generated by differential exon use (FIG. 4C).

Example 6

Sequence Polymorphisms in the Arntl2 Gene

Figure 5:
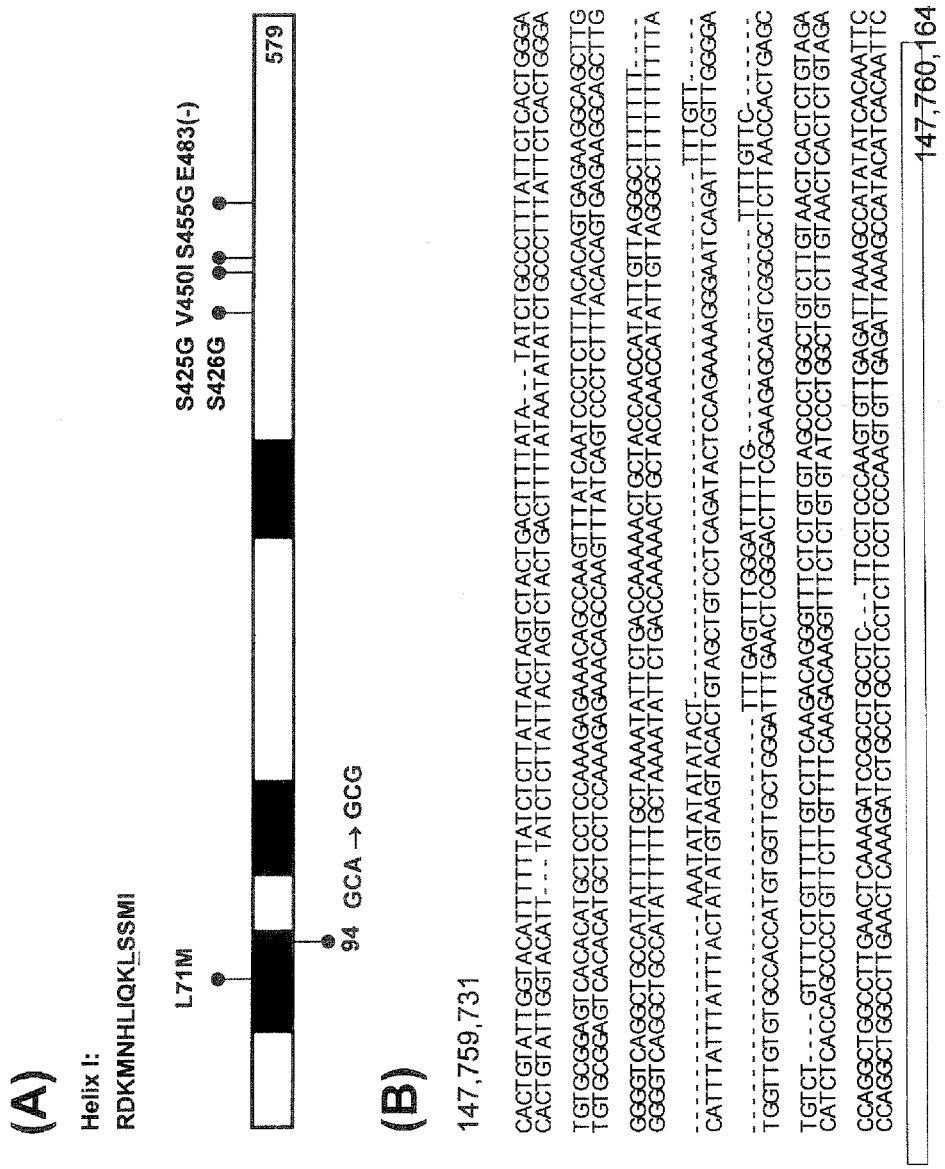
FIG. 5 shows C3H versus NOD polymorphisms within Bmal2. (A) Within the coding sequence of Bmal2, six codons at positions 71, 425, 426, 450, 455 and 483, and one synonymous mutation corresponding to codon 94 differed between the 6.VIII and NOD strains. Helix I is as shown in SEQ ID NO: 60. (B) The alignment of partial 3'UTR of the Bmal2 gene, corresponding to Ensembl Chr.6 sequence positions 147,759,731 to 147,760,164, from strain 6.VIII (upper sequence; SEQ ID NO: 61) and NOD displays significant sequence variation. The length of this region in 6.VIII is 123 bases shorter than in NOD mice (SEQ ID NO: 62).

To validate Arntl2 as a candidate gene, we analysed the sequence of its coding, 3' UTR and 5' UTR regions for polymorphisms between strain 6.VIII and NOD CO mice. Within exonic regions, one synonymous polymorphism at the wobble position of amino acid 94 (6.VIII: A and NOD mice: G), five non-synonymous polymorphisms and one insertion/deletion were identified (FIG. 5A). The leucine residue located within helix I of the HLH region at amino acid position 71 in strain 6.VIII has been replaced by a methionine in NOD mice. This leucine residue, which is highly conserved in the bHLH family, serves as an important contact site by interacting with residues in helix II in the formation of the helix structure, and is also involved in protein dimerisation (28, 29). The other polymorphisms identified were all located between the PAS-B domain and C terminus. Three serine residues in the strain 6.VIII at amino acid position 425, 426 and 455 were all replaced by glycine residues in the NOD mice. In NOD mice, the valine residue at position 450 in strain 6.VIII was replaced by isoleucine, and the glutamic acid at position 483 was deleted.

The 3' UTR sequences of the Arntl2 gene also showed striking variation. Multiple long insertion/deletions lying between the sequence position 147,759,748, located some 90 nucleotides distal to the stop codon of Arntl2, and the position 147,760,154 on mouse chromosome 6, resulted in major variation of the lengths of the DNA fragments in 6.VIII (409 bp) and in NOD (529 bp). Numerous base substitutions were also identified (FIG. 5B).

Analysis of the EST clone BY242187 allowed the identification of the upstream 5'UTR sequence of Arntl2. Two additional exons were identified between positions 147,716, 951 and 147,717,036 (E1') and between positions 147,723, 827 and 147,723,947 with the E1' exon locating about 9.4 kb upstream of the ATG. The position of the splice donor of the initial exon of AY005163 was found at position 147,726,370, some 95 nucleotides upstream of the ATG. No polymorphisms were identified within the 5'UTR region. However, numerous SNPs were identified adjacent to the E1' exon.

Figure 8:
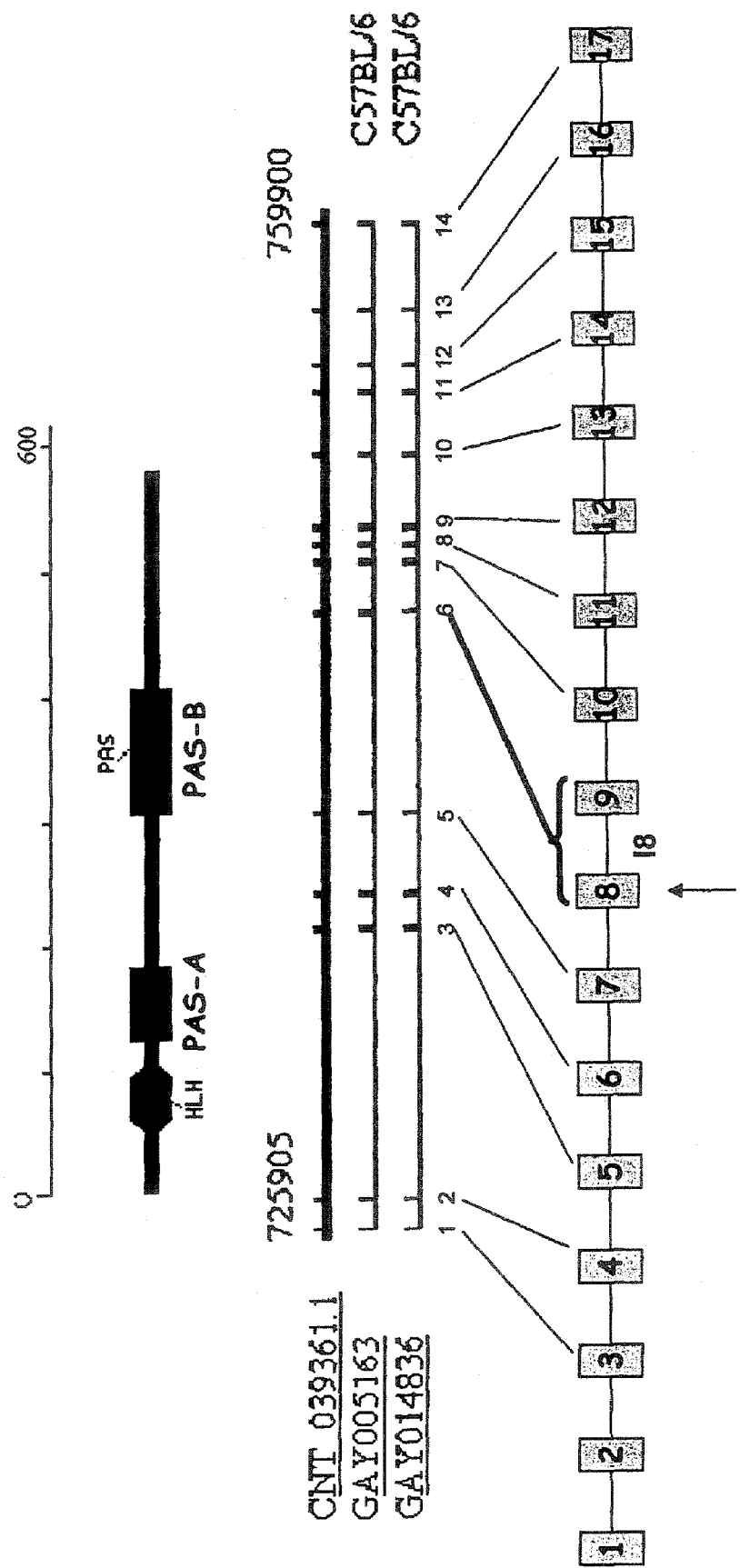
FIG. 8 shows a graphic depiction of information relevant to mBmal2.

The foregoing sequences are and explanatory information is provided in FIGS. 8-17, which correspond to the following:

FIG. 8 shows a graphic depiction of information relevant to mBmal2.

Figure 9:
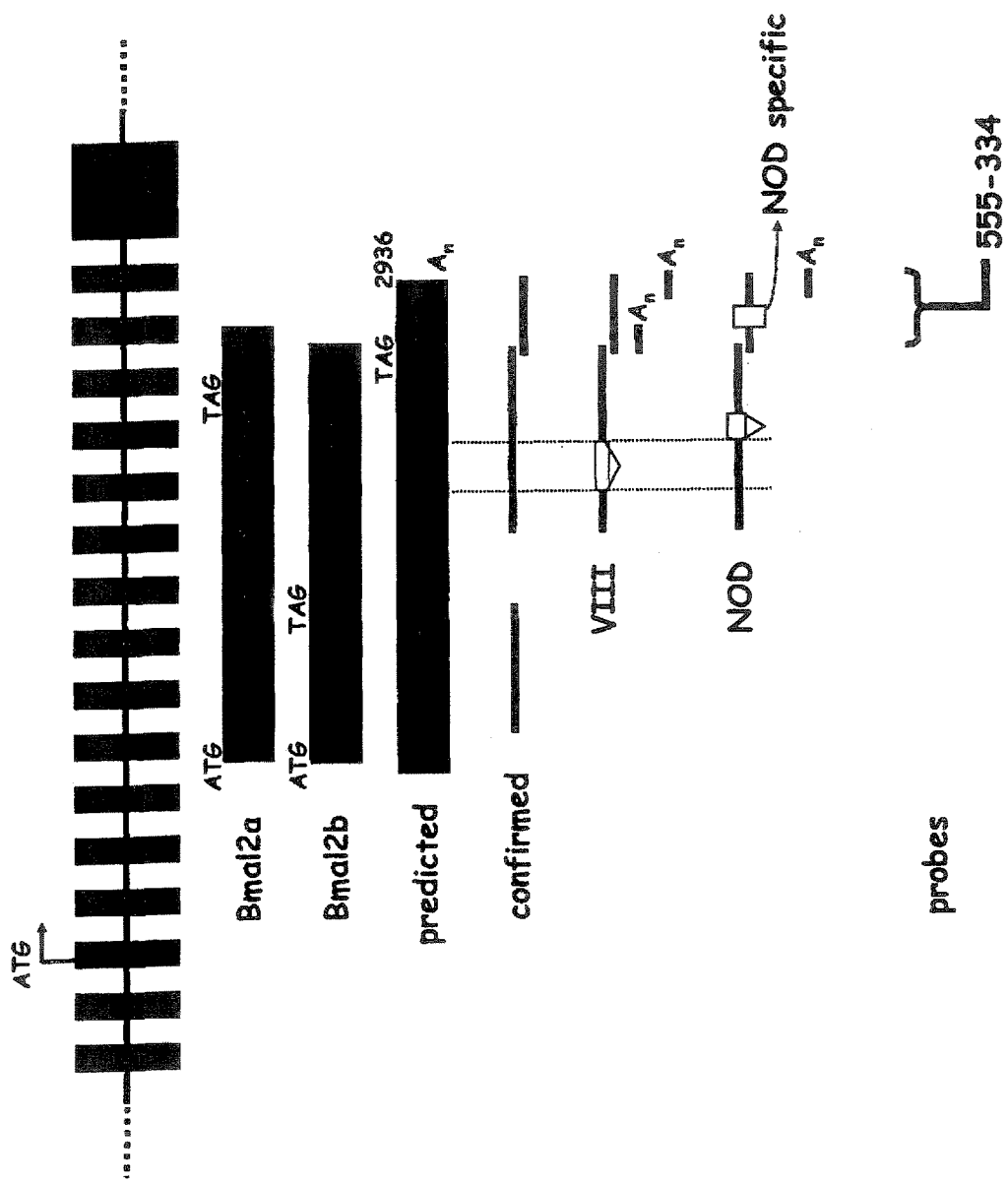
FIG. 9 shows the transcription profile of mBmal2.

FIG. 9 shows the transcription profile of mBmal2.

Figure 10:
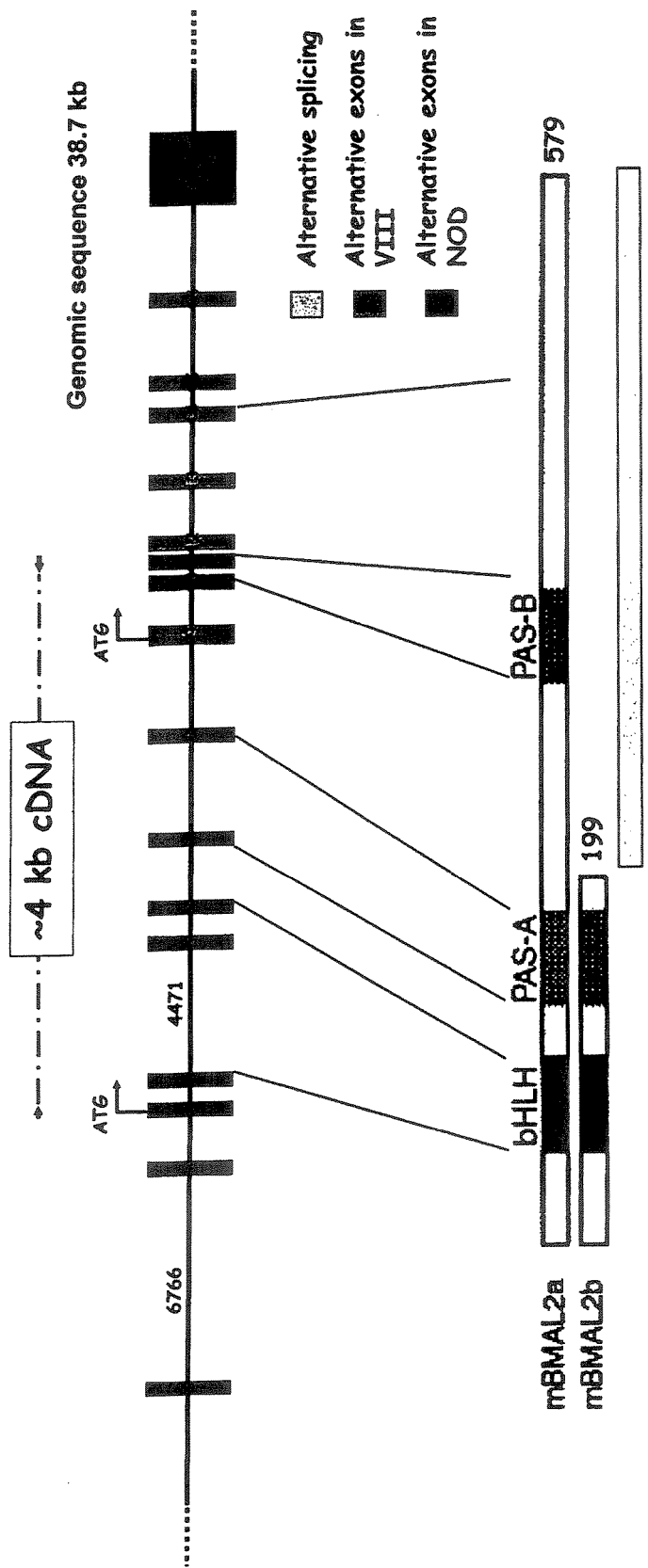
FIG. 10 shows the gene structure of mBmal2.

FIG. 10 shows the gene structure of mBmal2.

Figure 11:
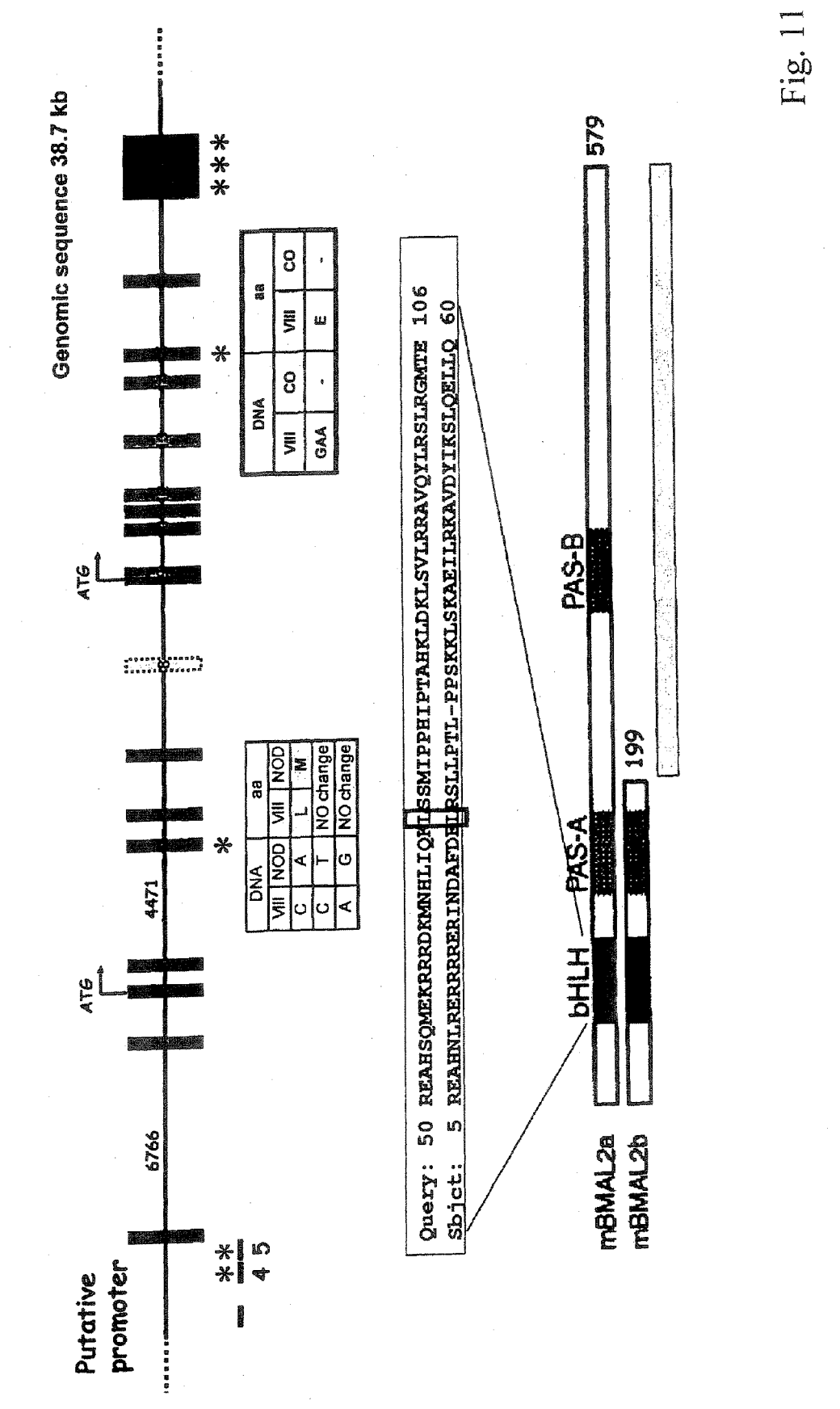

FIG. 11 shows the SNPs and Indels of mBmal2. The sequence depicted as "Query" is SEQ ID NO: 35 and the sequence depicted as "Sbjct" is SEQ ID NO: 36.

FIGS. 12A-B shows the Bmal2 coding region. NOD control is shown in SEQ ID NO: 33, while 6.VIII is shown in SEQ ID NO: 34.

FIGS. 13A-C shows the designation of the intron and exon portions of the genomic sequence. FIG. 13A: 071-E1 (118F-668R)-3 SNP (Ensembl Chr.6 147727278 to 147727780), Exon: underlined; NOD control is shown in SEQ ID NO: 37, while 6.VIII is shown in SEQ ID NO: 38. FIG. 13B: SNP35-38 (SNP35-38-64F+SNP35-38-465R)-1 SNP (Ensembl Chr.6 147746092-147746427); NOD control is shown in SEQ ID NO: 39, while 6.VIII is shown in SEQ ID NO: 40. FIG. 13C: 071-E5 (131F+465R)-5 SNPs (Ensembl Chr.6 147751781 to 147752273) Exon: underlined; NOD control is shown in SEQ ID NO: 41, while 6.VIII is shown in SEQ ID NO: 42. FIG. 13D: 071-SNP 75-80 (114F+440R)-1 SNPs (Ensembl Chr.6 starting from the 3rd base 147758806 to 147759169); NOD control is shown in SEQ ID NO: 43, while 6.VIII is shown in SEQ ID NO: 44.

FIG. 14 shows the Bmal2 coding region which marked exons. Bmal2 coding region (SEQ ID NO: 45)—exons marked by different colors (CO as example) Bold: the same exon but with splice forms (The part in bold and underlined is spliced out in mBmal2b sequence resulting in the early stop of translation. The present inventors found the same types of sequences in NOD and 6.VIII.) Underline and and italics with underline: the alternative exons of 6.VIII Italics: the alternative exons of NOD control.

FIGS. 15A-B shows the Sequencing files (071-43F to 071-2122R) corresponding to Bmal2c. More specifically, these figures show the sequencing data corresponding to Bmal2c by amplification using SEQ ID NO: 31 as the forward primer and the reverse complement of SEQ ID NO: 32 as the reverse primer. Bmal2c was cloned into a pGEM-T vector. The coding region is underlined. NOD control (FIG. 15A) is shown in SEQ ID NO: 46 with the encoded polypeptide appearing as SEQ ID NO: 47, while 6.VIII (FIG. 15B) is shown in SEQ ID NO: 48 with the encoded polypeptide appearing as SEQ ID NO: 49.

FIG. 16 shows the 3' UTR (right after the stop codon), the first base corresponds to Ensembl v37 chr.6 147759660. NOD control is shown in SEQ ID NO: 50, while 6.VIII is shown in SEQ ID NO: 51.

FIGS. 17A-D shows the upstream genomic sequence (primers: 071-16798F+071-17695R). FIG. 17A: Upstream genomic sequence (primers: 071-16798F+071-17695R)-4 SNPs (6.VIII sequence blast to Ensembl Chr.6: starting from the 100st base to the end 147715903 to 147716583- did not see the result of 1-99); NOD control is shown in SEQ ID NO: 52, while 6.VIII is shown in SEQ ID NO: 53. FIG. 17B: Upstream genomic sequence (primers: 071-17610F-18412R)-5 SNPs (Ensembl Chr.6 147716616 to 147717298); NOD control is shown in SEQ ID NO: 54, while 6.VIII is shown in SEQ ID NO: 55. FIG. 17C: Upstream genomic sequence (primers: 071-18235F-19236R)-2 SNPs (The 1$^{st}$ base=Ensembl Chr.6 147717274—the sequence has been broken to several pieces in the blast result); NOD control is shown in SEQ ID NO: 56, while 6.VIII is shown in SEQ ID NO: 57. FIG. 17D: Upstream genomic sequence (primers: 071-19129F+071-19896R)-6SNPs (The 24$^{th}$ nt to the end=Ensembl Chr.6 147718263 to 147718817); NOD control is shown in SEQ ID NO: 58, while 6.VIII is shown in SEQ ID NO: 59.

Example 7

Circadian Regulation of the Arnt2 Gene and the Circadian Genes

Figure 6:
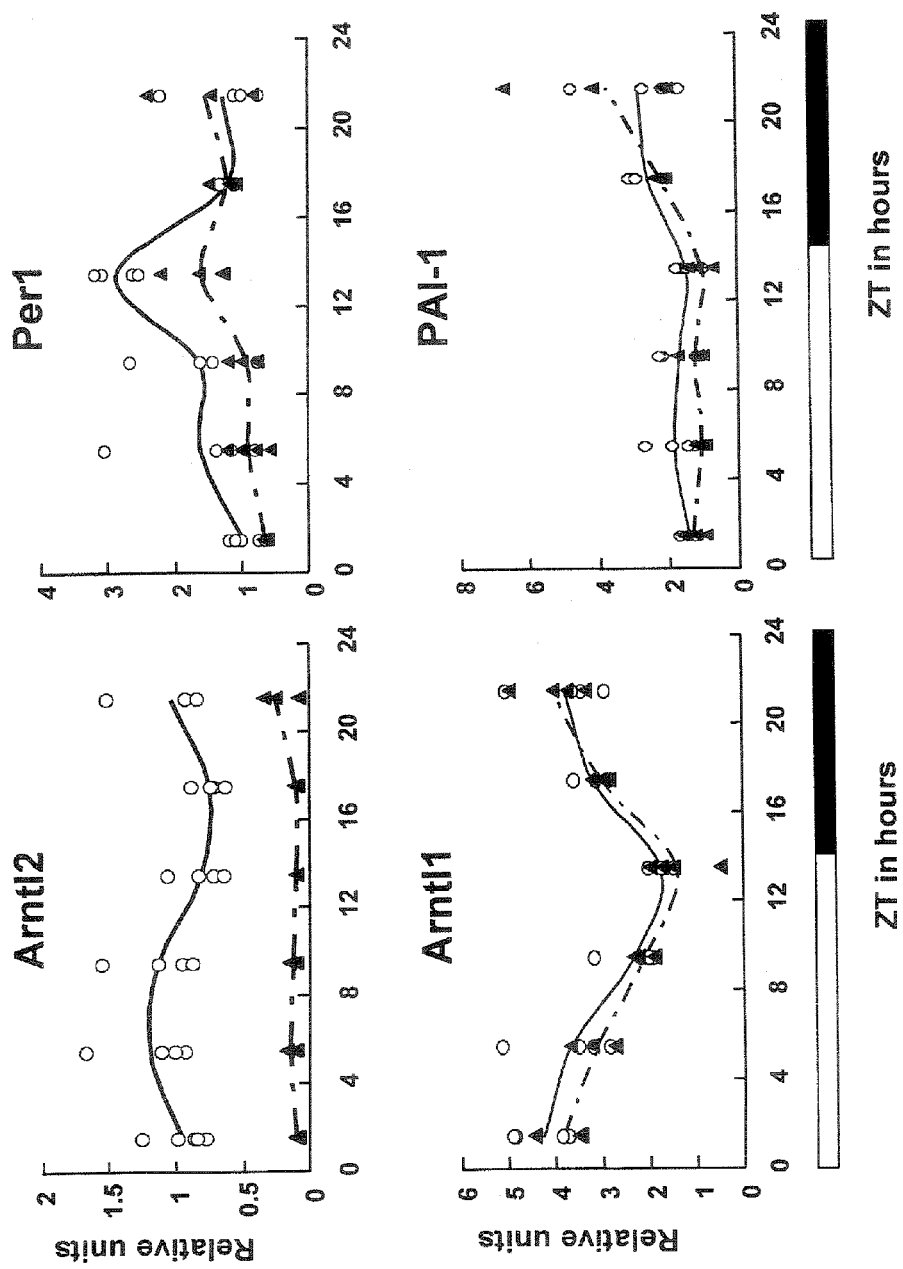
FIG. 6 shows circadian transcription profiles of Arntl2, Arntl1, Per1, and PAI-1 expression in spleens of single eight weeks old 6.VIII (white circles) and NOD (black triangles) mice housed under 14 hour light (blank bar) and 10 hour dark cycle (filled bar) which are shown as arbitrary units. ZT=zeitgeber time

The circadian expression of Arntl2 (Bmal2) in spleen was examined in mice housed under a cycle of fourteen hours artificial light and ten hours obscurity. These settings were identical to that used when diabetes incidence was monitored. Whilst splenic expression of Bmal2 oscillated moderately during the day, the differences in transcript level between strain 6.VIII and the NOD control were maintained over the whole 24-hour period (FIG. 6A). The strain difference in Bmal2 transcript levels suggested a possible alteration in the expression of other circadian genes regulated by Bmal2. Arntl1 (Bmal1), a master circadian gene and a close homolog of Bmal2, oscillated with a cycle which showed lowest expression at the beginning of the dark phase and highest at the beginning of light (FIG. 6B). No significant differences were found for either Bmal1 or for Per1, which is negatively regulated by Bmal1 (FIG. 6C). Similar results were obtained for other circadian genes involved in the autoregulatory feedback loop such as Per2, Per3, and Dec1.

In addition, the plasminogen activator inhibitor 1 (PAI-1) gene, a downstream circadian output gene regulated by Bmal2 in vitro (30), did not display strain specific differences in its transcription level (FIG. 6D). Hypoxia-inducible factor-1α (Hif-1α), a protein capable of heterodimerizing with Arntl2 in vitro (31), mediates expression of Adrenomedullin, which is in turn involved in T cell survival (32, 33). Analysis of Adrenomedullin expression failed to reveal differences between the 6.VIII strain and the NOD control spleens. We conclude that the up-regulation of Bmal2 in strain 6.VIII does not lead to a general alteration in transcription levels in the spleen of other circadian and hypoxia-induced genes.

Example 8

Cytosolic Phospholipase A2 is a Potential Downstream Target of Arntl2

From microarray experiments using pooled spleen samples from four eight-week old pre-diabetic females we concluded that the replacement of the 5.4 Mb Idd6 interval by C3H alleles resulted in a deregulation of about 5% of the transcriptome in 6.VIII mice compared to CO mice. We selected 7 downregulated and 14 upregulated transcripts with known or potential immune function to test whether their expression difference in spleen of 6.VIII mice would correlate with that of Arntl2.

Figure 7:
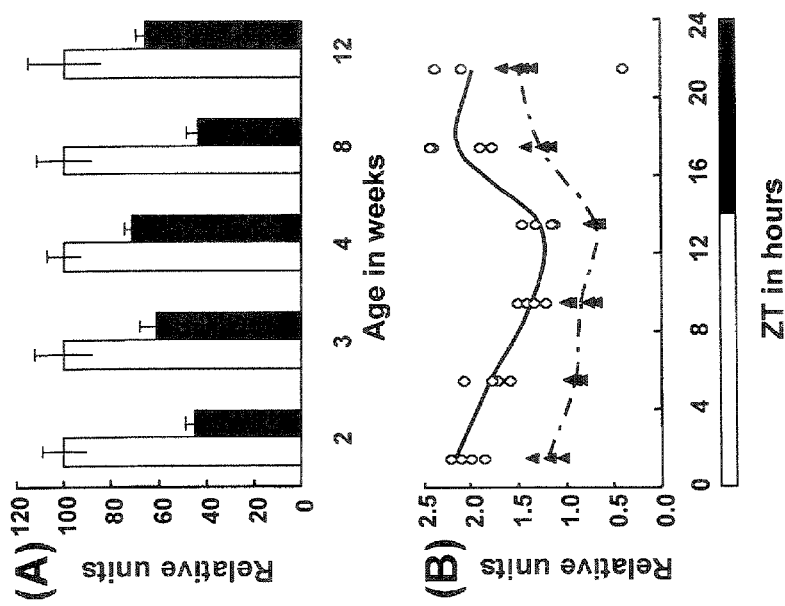
FIG. 7 shows relative expression in arbitrary units of Pla2g4a (A) in the spleens of different aged mice of 6.VIII (white bars) and NOD (black bars) strains. Data were pooled from four pre-diabetic female mice. (B) Circadian profile of Pla2g4a in spleen samples of 8 week-old 6.VIII (white circles) and NOD (black triangles) mice kept under 14 hours of light (blank bar) and 10 hours of dark (filled bar). ZT=zeitgeber time.

Real-time RT-PCR using pooled RNA from 6-7 week-old females confirmed the microarray results for two of the downregulated and nine of the upregulated genes that showed fold changes in excess of 1.5. Highest upregulation in the 6.VIII mice was found for the Chitinase 3-like 1 (Chi3l1) (5.6 fold), the Myeloperoxidase (Mpo) (2.1 fold), and Cytosolic phospholipase A2 (Pla2g4a) (1.7 fold) genes. When the genes were subject to detailed transcriptional analysis using spleen samples from mice of different ages, the hypoxia-involved Pla2g4a gene (34, 35) showed a particular interesting expression as it was, like Arntl2, upregulated in strain 6.VIII at all ages (FIG. 7). A two-fold upregulation was also measured when spleen samples from strain 6.VIIIc were compared to 6.VIIIa samples, confirming that the upregulation was at least to some extent directly to factors lying within Idd6.3.

A potential ARNT binding site (TGCGTG) was identified +101 to +106 of its transcription start site, which indicated that Pla2g4a might be a direct target of Arntl2. Similar to Arntl2, Pla2ga4a expression was upregulated in different splenic cell population, including CD4(+) T cells, CD8(+) T cell, B cells, and macrophages. We analysed its circadian profile and showed that whilst the expression of Pla2g4a oscillated mildly, the variation between strain 6.VIII and CO mice was maintained throughout the day (FIG. 7). Interestingly, the circadian profile of Pla2g4a whilst very similar to that of Arntl1 (Bmal1) and Arntl2 (Bmal2), was clearly different from those of Per1 and PAI-1. This suggests that Pla2g4a circadian expression correlates with that of the Bmal1 and Bmal2 and that it may be regulated by these transcription factors.

Example 9

Establishment of Cellular Ex Vivo Systems for Testing of the Arntl2 Gene

The present inventors were interested in exploring the adequacy of ex vivo systems in the characterization of the candidate gene. To this end the present inventors have undertaken studies on the RAW264.7 cell macrophage line and several other currently used mouse cell lines. The present inventors have been able to show that these cell lines can be used for the systematic testing of RNAi constructs cloned into the pSUPER vector system (Oligogene) prior to their subcloning into lentiviral vectors. The RAW264.7 is of particular interest for some of these studies because it can also be used for functional studies of the mediated Arntl2 pathways.

In these experiments, transient transfection using the lipofection method (jetPEI™ transfection reagent, Polyplus) of the RAW264.7 cell line results in about a 60% reduction of gene expression, when tested on Arntl2. Stable integrants can be expected to show about 90% reduction of expression. Arntl2 downregulation resulted in deregulation of other genes, known to be involved in diabetes development.

Numerous modifications and variations on the present invention are possible in light of the above teachings. It is, therefore, to be understood that within the scope of the accompanying claims, the invention may be practiced otherwise than as specifically described herein.

REFERENCES

1. Bottazzo, G. F., Todd, I., Mirakian, R., Belfiore, A. and Pujol-Borrell, R. (1986) Organ-specific autoimmunity: a 1986 overview. *Immunol Rev,* 94, 137-69.
2. Tisch, R. and McDevitt, H. (1996) Insulin-dependent diabetes mellitus. Cell, 85, 291-7.
3. Todd, J. A. and Wicker, L. S. (2001) Genetic protection from the inflammatory disease type 1 diabetes in humans and animal models. *Immunity,* 15, 387-95.
4. Serreze, D. V. and Leiter, E. H. (2001) Genes and cellular requirements for autoimmune diabetes susceptibility in nonobese diabetic mice. *Curr Dir Autoimmun,* 4, 31-67.
5. Makino, S., Kunimoto, K., Muraoka, Y., Mizushima, Y., Katagiri, K. and Tochino, Y. (1980) Breeding of a nonobese, diabetic strain of mice. *Jikken Dobutsu,* 29, 1-13.
6. Hattori, M., Buse, J. B., Jackson, R. A., Glimcher, L., Dorf, M. E., Minami, M., Makino, S., Moriwaki, K., Kuzuya, H., Imura, H. et al. (1986) The NOD mouse: recessive diabetogenic gene in the major histocompatibility complex. *Science,* 231, 733-5.
7. Deruytter, N., Boulard, O. and Garchon, H. J. (2004) Mapping non-class II H2-linked loci for type 1 diabetes in nonobese diabetic mice. *Diabetes,* 53, 3323-7.
8. Prochazka, M., Serreze, D. V., Worthen, S. M. and Leiter, E. H. (1989) Genetic control of diabetogenesis in NOD/Lt mice. Development and analysis of congenic stocks. *Diabetes,* 38, 1446-55.
9. McAleer, M. A., Reifsnyder, P., Palmer, S. M., Prochazka, M., Love, J. M., Copeman, J. B., Powell, E. E., Rodrigues, N. R., Prins, J. B., Serreze, D. V. et al. (1995) Crosses of NOD mice with the related NON strain. A polygenic model for IDDM. *Diabetes,* 44, 1186-95.
10. Wicker, L. S., Todd, J. A. and Peterson, L. B. (1995) Genetic control of autoimmune diabetes in the NOD mouse. *Annu Rev Immunol,* 13, 179-200.
11. Rogner, U. C. and Avner, P. (2003) Congenic mice: cutting tools for complex immune disorders. *Nat Rev Immunol,* 3, 243-52.
12. Lyons, P. (2002) Gene-expression profiling and the genetic dissection of complex disease. *Curr Opin Immunol,* 14, 627.
13. Eckenrode, S. E., Ruan, Q., Yang, P., Zheng, W., McIndoe, R. A. and She, J. X. (2004) Gene Expression Profiles Define a Key Checkpoint for Type 1 Diabetes in NOD Mice. *Diabetes,* 53, 366-75.
14. Ghosh, S., Palmer, S. M., Rodrigues, N. R., Cordell, H. J., Hearne, C. M., Cornall, R. J., Prins, J. B., McShane, P., Lathrop, G. M., Peterson, L. B. et al. (1993) Polygenic control of autoimmune diabetes in nonobese diabetic mice. *Nat Genet,* 4, 404-9.
15. de Gouyon, B., Melanitou, E., Richard, M. F., Requarth, M., Hahn, I. H., Guenet, J. L., Demenais, F., Julier, C., Lathrop, G. M., Boitard, C. et al. (1993) Genetic analysis of diabetes and insulitis in an interspecific cross of the nonobese diabetic mouse with Mus spretus. *Proc Natl Acad Sci USA,* 90, 1877-81.
16. Melanitou, E., Joly, F., Lathrop, M., Boitard, C. and Avner, P. (1998) Evidence for the presence of insulindependent diabetes-associated alleles on the distal part of mouse chromosome 6. *Genome Res,* 8, 608-20.
17. Rogner, U. C., Boitard, C., Morin, J., Melanitou, E. and Avner, P. (2001) Three loci on mouse chromosome 6 influence onset and final incidence of type I diabetes in NOD.C3H congenic strains. *Genomics,* 74, 163-71.
18. Carnaud, C., Gombert, J., Donnars, O., Garchon, H. and Herbelin, A. (2001) Protection against diabetes and improved NK/NKT cell performance in NOD.NK1.1 mice congenic at the NK complex. *J Immunol,* 166, 2404-11.
19. Dallas-Pedretti, A., McDuffie, M. and Haskins, K. (1995) A diabetes-associated T-cell autoantigen maps to a telomeric locus on mouse chromosome 6. *Proc Natl Acad Sci USA,* 92, 1386-90.
20. Leijon, K., Hammarstrom, B. and Holmberg, D. (1994) Non-obese diabetic (NOD) mice display enhanced immune responses and prolonged survival of lymphoid cells. *Int Immunol*, 6, 339-45.
21. Penha-Goncalves, C., Leijon, K., Persson, L. and Holmberg, D. (1995) Type 1 diabetes and the control of dexamethazone-induced apoptosis in mice maps to the same region on chromosome 6. *Genomics*, 28, 398-404.
22. Bergman, M. L., Duarte, N., Campino, S., Lundholm, M., Motta, V., Lejon, K., Penha-Goncalves, C. and Holmberg, D. (2003) Diabetes protection and restoration of thymocyte apoptosis in NOD Idd6 congenic strains. *Diabetes*, 52, 1677-82.
23. Bergman, M. L., Penha-Goncalves, C., Lejon, K. and Holmberg, D. (2001) Low rate of proliferation in immature thymocytes of the non-obese diabetic mouse maps to the Idd6 diabetes susceptibility region. *Diabetologia*, 44, 1054-61.
24. Rogner, U. C., Lepault, F., Gagnerault, M. C., Vallois, D., Morin, J., Avner, P. and Boitard, C. (2006) The Diabetes Type I Locus Idd6 Modulates Activity of CD4+CD25+ Regulatory T-Cells. *Diabetes*, 55, 186-92.
25. Grimm, C. H., Rogner, U. C. and Avner, P. (2003) Lrmp and Bcat1 are candidates for the type I diabetes susceptibly locus Idd6. *Autoimmunity*, 36, 241-246.
26. Yeh, C. T., Lu, S. C., Tseng, I. C., Lai, H. Y., Tsao, M. L., Huang, S. F. and Liaw, Y. F. (2003) Antisense overexpression of BMAL2 enhances cell proliferation. *Oncogene*, 22, 5306-14.
27. Okano, T., Yamamoto, K., Okano, K., Hirota, T., Kasahara, T., Sasaki, M., Takanaka, Y. and Fukada, Y. (2001) Chicken pineal clock genes: implication of BMAL2 as a bidirectional regulator in circadian clock oscillation. *Genes Cells*, 6, 825-36.
28. Atchley, W. R. and Fitch, W. M. (1997) A natural classification of the basic helix-loop-helix class of transcription factors. *Proc Natl Acad Sci USA*, 94, 5172-6.
29. Chavali, G. B., Vijayalakshmi, C. and Salunke, D. M. (2001) Analysis of sequence signature defining functional specificity and structural stability in helix-loop-helix proteins. *Proteins*, 42, 471-80.
30. Schoenhard, J. A., Smith, L. H., Painter, C. A., Eren, M., Johnson, C. H. and Vaughan, D. E. (2003) Regulation of the PAI-1 promoter by circadian clock components: differential activation by BMAL1 and BMAL2. *J Mol Cell Cardiol*, 35, 473-81.
31. Hogenesch, J. B., Gu, Y. Z., Moran, S. M., Shimomura, K., Radcliffe, L. A., Takahashi, J. S. and Bradfield, C. A. (2000) The basic helix-loop-helix-PAS protein MOP9 is a brain-specific heterodimeric partner of circadian and hypoxia factors. *J Neurosci*, 20, RC83.
32. Garayoa, M., Martinez, A., Lee, S., Pio, R., An, W. G., Neckers, L., Trepel, J., Montuenga, L. M., Ryan, H., Johnson, R. et al. (2000) Hypoxia-inducible factor-1 (HIF-1) up-regulates adrenomedullin expression in human tumor cell lines during oxygen deprivation: a possible promotion mechanism of carcinogenesis. *Mol Endocrinol*, 14, 848-62.
33. Makino, Y., Nakamura, H., Ikeda, E., Ohnuma, K., Yamauchi, K., Yabe, Y., Poellinger, L., Okada, Y., Morimoto, C. and Tanaka, H. (2003) Hypoxia-inducible factor regulates survival of antigen receptor-driven T cells. *J Immunol*, 171, 6534-40.
34. Ichinose, F., Ullrich, R., Sapirstein, A., Jones, R. C., Bonventre, J. V., Serhan, C. N., Bloch, K. D. and Zapol, W. M. (2002) Cytosolic phospholipase A(2) in hypoxic pulmonary vasoconstriction. *J Clin Invest*, 109, 1493-500.
35. Bazan, N. G. and Lukiw, W. J. (2002) Cyclooxygenase-2 and presenilin-1 gene expression induced by interleukin-1 beta and amyloid beta 42 peptide is potentiated by hypoxia in primary human neural cells. *J Biol Chem*, 277, 30359-67. Epub 2002 Jun. 5.
36. Schoenhard, J. A., Eren, M., Johnson, C. H. and Vaughan, D. E. (2002) Alternative splicing yields novel BMAL2 variants: tissue distribution and functional characterization. *Am J Physiol Cell Physiol*, 283, C103-14.
37. Oikawa, Y., Yamato, E., Tashiro, F., Yamamoto, M., Uozumi, N., Shimada, A., Shimizu, T. and Miyazaki, J. (2005) Protective role for cytosolic phospholipase A2alpha in autoimmune diabetes of mice. *FEBS Lett*, 579, 3975-8.
38. Fontenot, J. D., Rasmussen, J. P., Williams, L. M., Dooley, J. L., Farr, A. G. and Rudensky, A. Y. (2005) Regulatory T cell lineage specification by the forkhead transcription factor foxp3. *Immunity*, 22, 329-41.
39. Gunton, J. E., Kulkarni, R. N., Yim, S., Okada, T., Hawthorne, W. J., Tseng, Y. H., Roberson, R. S., Ricordi, C., O'Connell, P. J., Gonzalez, F. J. et al. (2005) Loss of ARNT/HIF1beta mediates altered gene expression and pancreatic-islet dysfunction in human type 2 diabetes. *Cell*, 122, 337-49.
40. Levisetti, M. G. and Polonsky, K. S. (2005) Diabetic pancreatic beta cells ARNT all they should be. *Cell Metab*, 2, 78-80.
41. Cartharius, K., Frech, K., Grote, K., Klocke, B., Haltmeier, M., Klingenhoff, A., Frisch, M., Bayerlein, M. and Werner, T. (2005) MatInspector and beyond: promoter analysis based on transcription factor binding sites. *Bioinformatics*, 21, 2933-42. Epub 2005 Apr. 28.
42. Grand, E. K., Grand, F. H., Chase, A. J., Ross, F. M., Corcoran, M. M., Oscier, D. G. and Cross, N. C. (2004) Identification of a novel gene, FGFR1OP2, fused to FGFR1 in 8p11 myeloproliferative syndrome. *Genes Chromosomes Cancer*, 40, 78-83.
43. Akashi, H., Han, H. J., Iizaka, M., Nakajima, Y., Furukawa, Y., Sugano, S., Imai, K. and Nakamura, Y. Isolation and characterization of a novel gene encoding a putative seven-span transmembrane protein, TM7SF3, 305-9.
44. Tudor, M., Murray, P. J., Onufryk, C., Jaenisch, R. and Young, R. A. (1999) Ubiquitous expression and embryonic requirement for RNA polymerase II coactivator subunit Srb7 in mice. *Genes Dev*, 13, 2365-8.

The invention claimed is:

1. A method of determining the susceptibility of a human to developing insulin-dependent diabetes comprising:
   a) acquiring a sample from said human;
   b) determining the expression level of the Arntl2 gene in said sample;
   c) comparing the expression level of the Arntl2 gene determined in (b) with that of the average expression level of the Arntl2 gene in samples of the corresponding type obtained from the population to which said human belongs, wherein an expression level of the Arntl2 gene in said human that is lower than that of the average expression level of the Arntl2 gene is correlated with an increased susceptibility in developing insulin-dependent diabetes.

2. The method of claim 1, wherein said Arntl2 gene is at least 90% homologous to the sequence of SEQ ID NO: 3.

3. The method of claim 1, wherein said Arntl2 gene is at least 95% homologous to the sequence of SEQ ID NO: 3.

4. The method of claim 1, wherein said sample comprises splenic cells.

5. The method of claim 4, wherein said splenic cells are at least one type selected from the group consisting of CD4(+) T cells, CD8(+) T cells, B cells, and macrophages.

* * * * *

SEQUENCE LISTING

<160> NUMBER OF SEQ ID NOS: 62

<210> SEQ ID NO 1
<211> LENGTH: 1740
<212> TYPE: DNA
<213> ORGANISM: Mus musculus
<220> FEATURE:
<221> NAME/KEY: CDS
<222> LOCATION: (1)..(1740)

```
<400> SEQUENCE: 1 atg gag ttt cca agg aaa cgc aga ggc aga gat tcc cag cca ctc cag      48
Met Glu Phe Pro Arg Lys Arg Arg Gly Arg Asp Ser Gln Pro Leu Gln
1               5                   10                  15 tca gaa ttc atg aca gac aca aca gtg gaa agt ctt ccc cag aat ccc      96
Ser Glu Phe Met Thr Asp Thr Thr Val Glu Ser Leu Pro Gln Asn Pro
            20                  25                  30 ttt gcc tct ctt ctt tca aca aga aca gga gta tca gcg ccc agt ggc     144
Phe Ala Ser Leu Leu Ser Thr Arg Thr Gly Val Ser Ala Pro Ser Gly
        35                  40                  45 atc agg gaa gct cac agc cag atg gaa aag cgt cgg aga gac aag atg     192
Ile Arg Glu Ala His Ser Gln Met Glu Lys Arg Arg Arg Asp Lys Met
50                  55                  60 aac cat ctg att cag aaa ctg tca tct atg atc cct cca cac atc ccc     240
Asn His Leu Ile Gln Lys Leu Ser Ser Met Ile Pro Pro His Ile Pro
65                  70                  75                  80 acg gcc cac aaa ctg gac aag ctc agc gtc ttg agg agg gcg gtg cag     288
Thr Ala His Lys Leu Asp Lys Leu Ser Val Leu Arg Arg Ala Val Gln
                85                  90                  95 tac ttg agg tct ctg aga ggc atg aca gag ctt tac tta gga gaa aac     336
Tyr Leu Arg Ser Leu Arg Gly Met Thr Glu Leu Tyr Leu Gly Glu Asn
            100                 105                 110 tct aaa cct tca ttt att cag gat aag gaa ctc agt cac tta atc ctc     384
Ser Lys Pro Ser Phe Ile Gln Asp Lys Glu Leu Ser His Leu Ile Leu
        115                 120                 125 aag gca gca gaa ggc ttc ctg ttt gtg gtt gga tgc gaa aga ggg aga     432
Lys Ala Ala Glu Gly Phe Leu Phe Val Val Gly Cys Glu Arg Gly Arg
130                 135                 140 att ttt tac gtt tct aag tct gtc tcc aaa aca ctg cgt tat gat cag     480
Ile Phe Tyr Val Ser Lys Ser Val Ser Lys Thr Leu Arg Tyr Asp Gln
145                 150                 155                 160 gct agc ttg ata gga cag aat ttg ttt gac ttc tta cac cca aaa gac     528
Ala Ser Leu Ile Gly Gln Asn Leu Phe Asp Phe Leu His Pro Lys Asp
                165                 170                 175 gtc gcc aaa gta aag gaa caa ctt tct tgt gat ggt cca cca aga gag     576
Val Ala Lys Val Lys Glu Gln Leu Ser Cys Asp Gly Ser Pro Arg Glu
            180                 185                 190 aaa cct ata gac acc aaa acc tct cag gtt tac agt cac ccc tac act     624
Lys Pro Ile Asp Thr Lys Thr Ser Gln Val Tyr Ser His Pro Tyr Thr
        195                 200                 205 ggg cga cca cgc atg cat tct ggc tcc aga cga tct ttc ttc ttt aga     672
Gly Arg Pro Arg Met His Ser Gly Ser Arg Arg Ser Phe Phe Phe Arg
210                 215                 220 atg aag agc tgt acc gtc cct gtc aaa gaa gag cag cca tgc tcg tcc     720
Met Lys Ser Cys Thr Val Pro Val Lys Glu Glu Gln Pro Cys Ser Ser
225                 230                 235                 240 tgc tca aag aag aaa gac cat aga aaa ttc cac acc gtc cat tgc act     768
Cys Ser Lys Lys Lys Asp His Arg Lys Phe His Thr Val His Cys Thr
                245                 250                 255 gga tac ttg aga agc tgg cct ctg aat gtt gtt ggc atg gag aaa gag     816
Gly Tyr Leu Arg Ser Trp Pro Leu Asn Val Val Gly Met Glu Lys Glu
            260                 265                 270 tcg ggt ggt ggg aag gac agc ggt cct ctt acc tgc ctt gtg gct atg     864
Ser Gly Gly Gly Lys Asp Ser Gly Pro Leu Thr Cys Leu Val Ala Met
        275                 280                 285 gga cgg ttg cat cca tac att gtc cct caa aag agt ggc aag atc aac     912
Gly Arg Leu His Pro Tyr Ile Val Pro Gln Lys Ser Gly Lys Ile Asn
290                 295                 300 gtg aga ccg gct gag ttc ata act cgc ttc gca atg aac ggg aaa ttc     960
```

```
Val Arg Pro Ala Glu Phe Ile Thr Arg Phe Ala Met Asn Gly Lys Phe
305                 310                 315                 320 gtc tat gtt gac caa agg gca acg gca att tta gga tac ctg cct cag       1008
Val Tyr Val Asp Gln Arg Ala Thr Ala Ile Leu Gly Tyr Leu Pro Gln
                325                 330                 335 gaa ctt ttg gga act tca tgt tat gaa tat ttt cat cag gat gac cac       1056
Glu Leu Leu Gly Thr Ser Cys Tyr Glu Tyr Phe His Gln Asp Asp His
        340                 345                 350 agt agt ttg act gac aag cac aaa gca gtt ctg cag agt aag gag aaa       1104
Ser Ser Leu Thr Asp Lys His Lys Ala Val Leu Gln Ser Lys Glu Lys
            355                 360                 365 ata ctt aca gac tca tac aaa ttc aga gtg aag gat ggt gcc ttc gtg       1152
Ile Leu Thr Asp Ser Tyr Lys Phe Arg Val Lys Asp Gly Ala Phe Val
370                 375                 380 act ctg aag agt gag tgg ttc agc ttc aca aac cct tgg acc aaa gag       1200
Thr Leu Lys Ser Glu Trp Phe Ser Phe Thr Asn Pro Trp Thr Lys Glu
385                 390                 395                 400 ctg gag tac att gtg tct gtc aac aca ttg gtt ttg ggg cgc agt gag       1248
Leu Glu Tyr Ile Val Ser Val Asn Thr Leu Val Leu Gly Arg Ser Glu
                405                 410                 415 acc agg ctg tct ttg ctt cat tgc ggc ggc agc agc cag tcc tcc gaa       1296
Thr Arg Leu Ser Leu Leu His Cys Gly Gly Ser Ser Gln Ser Ser Glu
        420                 425                 430 gac tca ttt aga caa tcc tgc atc aat gtg ccc ggt gta tcc acg ggg       1344
Asp Ser Phe Arg Gln Ser Cys Ile Asn Val Pro Gly Val Ser Thr Gly
            435                 440                 445 acc gtc ctt ggt gct ggg agt att gga aca gat att gca aat gag gtt       1392
Thr Val Leu Gly Ala Gly Ser Ile Gly Thr Asp Ile Ala Asn Glu Val
450                 455                 460 ctg agt tta cag aga tta cac tct tca tcc cca gaa gat gca agc cct       1440
Leu Ser Leu Gln Arg Leu His Ser Ser Ser Pro Glu Asp Ala Ser Pro
465                 470                 475                 480 tca gaa gaa gtg aga gat gac tgc agt gta aat ggt ggg aat gcc tat       1488
Ser Glu Glu Val Arg Asp Asp Cys Ser Val Asn Gly Gly Asn Ala Tyr
                485                 490                 495 ggg cct gca tcc act agg gag cct ttt gca gtg agc cct tct gaa aca       1536
Gly Pro Ala Ser Thr Arg Glu Pro Phe Ala Val Ser Pro Ser Glu Thr
        500                 505                 510 gag gtc ctg gag gct gcc agg caa cac cag agc act gaa ccc gcc cac       1584
Glu Val Leu Glu Ala Ala Arg Gln His Gln Ser Thr Glu Pro Ala His
            515                 520                 525 cct cac gga cca ctt ccc ggt gac agt gcc cag ctg ggt ttt gat gtc       1632
Pro His Gly Pro Leu Pro Gly Asp Ser Ala Gln Leu Gly Phe Asp Val
530                 535                 540 ctg tgt gac agt gac agc ata gac atg gct gca ttc atg aat tac ctc       1680
Leu Cys Asp Ser Asp Ser Ile Asp Met Ala Ala Phe Met Asn Tyr Leu
545                 550                 555                 560 gaa gca gag ggg ggc ctg ggt gac cct ggg gac ttc agt gac atc cag       1728
Glu Ala Glu Gly Gly Leu Gly Asp Pro Gly Asp Phe Ser Asp Ile Gln
                565                 570                 575 tgg gca ctc tag                                                        1740
Trp Ala Leu <210> SEQ ID NO 2
<211> LENGTH: 579
<212> TYPE: PRT
<213> ORGANISM: Mus musculus

<400> SEQUENCE: 2

Met Glu Phe Pro Arg Lys Arg Arg Gly Arg Asp Ser Gln Pro Leu Gln
1               5                   10                  15
```

Ser Glu Phe Met Thr Asp Thr Thr Val Glu Ser Leu Pro Gln Asn Pro
            20                  25                  30

Phe Ala Ser Leu Leu Ser Thr Arg Thr Gly Val Ser Ala Pro Ser Gly
            35                  40                  45

Ile Arg Glu Ala His Ser Gln Met Glu Lys Arg Arg Asp Lys Met
 50                  55                  60

Asn His Leu Ile Gln Lys Leu Ser Ser Met Ile Pro Pro His Ile Pro
 65                  70                  75                  80

Thr Ala His Lys Leu Asp Lys Leu Ser Val Leu Arg Arg Ala Val Gln
                85                  90                  95

Tyr Leu Arg Ser Leu Arg Gly Met Thr Glu Leu Tyr Leu Gly Glu Asn
            100                 105                 110

Ser Lys Pro Ser Phe Ile Gln Asp Lys Glu Leu Ser His Leu Ile Leu
            115                 120                 125

Lys Ala Ala Glu Gly Phe Leu Phe Val Val Gly Cys Glu Arg Gly Arg
            130                 135                 140

Ile Phe Tyr Val Ser Lys Ser Val Ser Lys Thr Leu Arg Tyr Asp Gln
145                 150                 155                 160

Ala Ser Leu Ile Gly Gln Asn Leu Phe Asp Phe Leu His Pro Lys Asp
                165                 170                 175

Val Ala Lys Val Lys Glu Gln Leu Ser Cys Asp Gly Ser Pro Arg Glu
            180                 185                 190

Lys Pro Ile Asp Thr Lys Thr Ser Gln Val Tyr Ser His Pro Tyr Thr
            195                 200                 205

Gly Arg Pro Arg Met His Ser Gly Ser Arg Arg Ser Phe Phe Phe Arg
            210                 215                 220

Met Lys Ser Cys Thr Val Pro Val Lys Glu Gln Pro Cys Ser Ser
225                 230                 235                 240

Cys Ser Lys Lys Lys Asp His Arg Lys Phe His Thr Val His Cys Thr
                245                 250                 255

Gly Tyr Leu Arg Ser Trp Pro Leu Asn Val Val Gly Met Glu Lys Glu
            260                 265                 270

Ser Gly Gly Gly Lys Asp Ser Gly Pro Leu Thr Cys Leu Val Ala Met
            275                 280                 285

Gly Arg Leu His Pro Tyr Ile Val Pro Gln Lys Ser Gly Lys Ile Asn
290                 295                 300

Val Arg Pro Ala Glu Phe Ile Thr Arg Phe Ala Met Asn Gly Lys Phe
305                 310                 315                 320

Val Tyr Val Asp Gln Arg Ala Thr Ala Ile Leu Gly Tyr Leu Pro Gln
            325                 330                 335

Glu Leu Leu Gly Thr Ser Cys Tyr Glu Tyr Phe His Gln Asp Asp His
            340                 345                 350

Ser Ser Leu Thr Asp Lys His Lys Ala Val Leu Gln Ser Lys Glu Lys
            355                 360                 365

Ile Leu Thr Asp Ser Tyr Lys Phe Arg Val Lys Asp Gly Ala Phe Val
            370                 375                 380

Thr Leu Lys Ser Glu Trp Phe Ser Phe Thr Asn Pro Trp Thr Lys Glu
385                 390                 395                 400

Leu Glu Tyr Ile Val Ser Val Asn Thr Leu Val Leu Gly Arg Ser Glu
                405                 410                 415

Thr Arg Leu Ser Leu Leu His Cys Gly Gly Ser Ser Gln Ser Ser Glu
            420                 425                 430

Asp Ser Phe Arg Gln Ser Cys Ile Asn Val Pro Gly Val Ser Thr Gly

```
                435                440                445
Thr Val Leu Gly Ala Gly Ser Ile Gly Thr Asp Ile Ala Asn Glu Val
            450                455                460
Leu Ser Leu Gln Arg Leu His Ser Ser Pro Glu Asp Ala Ser Pro
465                470                475                480
Ser Glu Glu Val Arg Asp Asp Cys Ser Val Asn Gly Asn Ala Tyr
                485                490                495
Gly Pro Ala Ser Thr Arg Glu Pro Phe Ala Val Ser Pro Ser Glu Thr
            500                505                510
Glu Val Leu Glu Ala Ala Arg Gln His Gln Ser Thr Glu Pro Ala His
    515                520                525
Pro His Gly Pro Leu Pro Gly Asp Ser Ala Gln Leu Gly Phe Asp Val
            530                535                540
Leu Cys Asp Ser Asp Ser Ile Asp Met Ala Ala Phe Met Asn Tyr Leu
545                550                555                560
Glu Ala Glu Gly Gly Leu Gly Asp Pro Gly Asp Phe Ser Asp Ile Gln
                565                570                575
Trp Ala Leu

<210> SEQ ID NO 3
<211> LENGTH: 1930
<212> TYPE: DNA
<213> ORGANISM: Homo sapiens
<220> FEATURE:
<221> NAME/KEY: CDS
<222> LOCATION: (19)..(1929)

<400> SEQUENCE: 3
gaccaagtgg ctcctgcg atg gcg gcg gaa gag gag gct gcg gcg gga ggt    51
                    Met Ala Ala Glu Glu Glu Ala Ala Ala Gly Gly
                     1               5                  10 aaa gtg ttg aga gag gag aac cag tgc att gct cct gtg gtt tcc agc    99
Lys Val Leu Arg Glu Glu Asn Gln Cys Ile Ala Pro Val Val Ser Ser
             15                  20                  25 cgc gtg agt cca ggg aca aga cca aca gct atg ggg tct ttc agc tca   147
Arg Val Ser Pro Gly Thr Arg Pro Thr Ala Met Gly Ser Phe Ser Ser
         30                  35                  40 cac atg aca gag ttt cca cga aaa cgc aaa gga agt gat tca gac cca   195
His Met Thr Glu Phe Pro Arg Lys Arg Lys Gly Ser Asp Ser Asp Pro
     45                  50                  55 tcc cag tca gga atc atg aca gaa aaa gtg gtg gaa aag ctt tct cag   243
Ser Gln Ser Gly Ile Met Thr Glu Lys Val Val Glu Lys Leu Ser Gln
 60                  65                  70                  75 aat ccc ctt acc tat ctt ctt tca aca agg ata gaa ata tca gcc tcc   291
Asn Pro Leu Thr Tyr Leu Leu Ser Thr Arg Ile Glu Ile Ser Ala Ser
                 80                  85                  90 agt ggc agc aga gtg gaa gat ggt gaa cac caa gtt aaa atg aag gcc   339
Ser Gly Ser Arg Val Glu Asp Gly Glu His Gln Val Lys Met Lys Ala
             95                 100                 105 ttc aga gaa gct cat agc caa act gaa aag cgg agg aga gat aaa atg   387
Phe Arg Glu Ala His Ser Gln Thr Glu Lys Arg Arg Arg Asp Lys Met
        110                 115                 120 aat aac ctg att gaa gaa ctg tct gca atg atc cct cag tgc aac ccc   435
Asn Asn Leu Ile Glu Glu Leu Ser Ala Met Ile Pro Gln Cys Asn Pro
    125                 130                 135 atg gcg cgt aaa ctg gac aaa ctt aca gtt tta aga atg gct gtt caa   483
Met Ala Arg Lys Leu Asp Lys Leu Thr Val Leu Arg Met Ala Val Gln
140                 145                 150                 155 cac ttg aga tct tta aaa ggc ttg aca aat tct tat gtg gga agt aat   531
```

```
                His Leu Arg Ser Leu Lys Gly Leu Thr Asn Ser Tyr Val Gly Ser Asn
                                160                 165                 170 tat aga cca tca ttt ctt cag gat aat gag ctc aga cat tta atc ctt        579
Tyr Arg Pro Ser Phe Leu Gln Asp Asn Glu Leu Arg His Leu Ile Leu
            175                 180                 185 aag act gca gaa ggc ttc tta ttt gtg gtt gga tgt gaa aga gga aaa        627
Lys Thr Ala Glu Gly Phe Leu Phe Val Val Gly Cys Glu Arg Gly Lys
            190                 195                 200 att ctc ttc gtt tct aag tca gtc tcc aaa ata ctt aat tat gat cag        675
Ile Leu Phe Val Ser Lys Ser Val Ser Lys Ile Leu Asn Tyr Asp Gln
        205                 210                 215 gct agt ttg act gga caa agc tta ttt gac ttc tta cat cca aaa gat        723
Ala Ser Leu Thr Gly Gln Ser Leu Phe Asp Phe Leu His Pro Lys Asp
220                 225                 230                 235 gtt gcc aaa gta aag gaa caa ctt tct tct ttt gat att tca cca aga        771
Val Ala Lys Val Lys Glu Gln Leu Ser Ser Phe Asp Ile Ser Pro Arg
                240                 245                 250 gaa aag cta ata gat gcc aaa act ggt ttg caa gtt cac agt aat ctc        819
Glu Lys Leu Ile Asp Ala Lys Thr Gly Leu Gln Val His Ser Asn Leu
                255                 260                 265 cac gct gga agg aca cgt gtg tat tct ggc tca aga cga tct ttt ttc        867
His Ala Gly Arg Thr Arg Val Tyr Ser Gly Ser Arg Arg Ser Phe Phe
            270                 275                 280 tgt cgg ata aag agt tgt aaa atc tct gtc aaa gaa gag cat gga tgc        915
Cys Arg Ile Lys Ser Cys Lys Ile Ser Val Lys Glu Glu His Gly Cys
        285                 290                 295 tta ccc aac tca aag aag aaa gag cac aga aaa ttc tat act atc cat        963
Leu Pro Asn Ser Lys Lys Lys Glu His Arg Lys Phe Tyr Thr Ile His
300                 305                 310                 315 tgc act ggt tac ttg aga agc tgg cct cca aat att gtt gga atg gaa       1011
Cys Thr Gly Tyr Leu Arg Ser Trp Pro Pro Asn Ile Val Gly Met Glu
                320                 325                 330 gaa gaa agg aac agt aag aaa gac aac agt aat ttt acc tgc ctt gtg       1059
Glu Glu Arg Asn Ser Lys Lys Asp Asn Ser Asn Phe Thr Cys Leu Val
                335                 340                 345 gcc att gga aga tta cag cca tat att gtt cca cag aac agt gga gag       1107
Ala Ile Gly Arg Leu Gln Pro Tyr Ile Val Pro Gln Asn Ser Gly Glu
            350                 355                 360 att aat gtg aaa cca act gaa ttt ata acc cgg ttt gca gtg aat gga       1155
Ile Asn Val Lys Pro Thr Glu Phe Ile Thr Arg Phe Ala Val Asn Gly
        365                 370                 375 aaa ttt gtc tat gta gat caa agg gca aca gcg att tta gga tat ctg       1203
Lys Phe Val Tyr Val Asp Gln Arg Ala Thr Ala Ile Leu Gly Tyr Leu
380                 385                 390                 395 cct cag gaa ctt ttg gga act tct tgt tat gaa tat ttt cat caa gat       1251
Pro Gln Glu Leu Leu Gly Thr Ser Cys Tyr Glu Tyr Phe His Gln Asp
                400                 405                 410 gac cac aat aat ttg act gac aag cac aaa gca gtt cta cag agt aag       1299
Asp His Asn Asn Leu Thr Asp Lys His Lys Ala Val Leu Gln Ser Lys
                415                 420                 425 gag aaa ata ctt aca gat tcc tac aaa ttc aga gca aaa gat ggc tct       1347
Glu Lys Ile Leu Thr Asp Ser Tyr Lys Phe Arg Ala Lys Asp Gly Ser
            430                 435                 440 ttt gta act tta aaa agc caa tgg ttt agt ttc aca aat cct tgg aca       1395
Phe Val Thr Leu Lys Ser Gln Trp Phe Ser Phe Thr Asn Pro Trp Thr
        445                 450                 455 aaa gaa ctg gaa tat att gta tct gtc aac act tta gtt ttg gga cat       1443
Lys Glu Leu Glu Tyr Ile Val Ser Val Asn Thr Leu Val Leu Gly His
460                 465                 470                 475 agt gag cct gga gaa gca tca ttt tta cct tgt agc tct caa tca tca       1491
```

```
Ser Glu Pro Gly Glu Ala Ser Phe Leu Pro Cys Ser Ser Gln Ser Ser
            480                 485                 490 gaa gaa tcc tct aga cag tcc tgt atg agt gta cct gga atg tct act      1539
Glu Glu Ser Ser Arg Gln Ser Cys Met Ser Val Pro Gly Met Ser Thr
            495                 500                 505 gga aca gta ctt ggt gct ggt agt att gga aca gat att gca aat gaa      1587
Gly Thr Val Leu Gly Ala Gly Ser Ile Gly Thr Asp Ile Ala Asn Glu
            510                 515                 520 att ctg gat tta cag agg tta cag tct tct tca tac ctt gat gat tcg      1635
Ile Leu Asp Leu Gln Arg Leu Gln Ser Ser Ser Tyr Leu Asp Asp Ser
525                 530                 535 agt cca aca ggt tta atg aaa gat act cat act gta aac tgc agg agt      1683
Ser Pro Thr Gly Leu Met Lys Asp Thr His Thr Val Asn Cys Arg Ser
540                 545                 550                 555 atg tca aat aag gag ttg ttt cca cca agt cct tct gaa atg ggg gag      1731
Met Ser Asn Lys Glu Leu Phe Pro Pro Ser Pro Ser Glu Met Gly Glu
                560                 565                 570 cta gag gct acc agg caa aac cag agt act gtt gct gtc cac agc cat      1779
Leu Glu Ala Thr Arg Gln Asn Gln Ser Thr Val Ala Val His Ser His
            575                 580                 585 gag cca ctc ctc agt gat ggt gca cag ttg gat ttc gat gcc cta tgt      1827
Glu Pro Leu Leu Ser Asp Gly Ala Gln Leu Asp Phe Asp Ala Leu Cys
            590                 595                 600 gac aat gat gac aca gcc atg gct gca ttt atg aat tac tta gaa gca      1875
Asp Asn Asp Asp Thr Ala Met Ala Ala Phe Met Asn Tyr Leu Glu Ala
605                 610                 615 gag ggg ggc ctg gga gac cct ggg gac ttc agt gac atc cag tgg acc      1923
Glu Gly Gly Leu Gly Asp Pro Gly Asp Phe Ser Asp Ile Gln Trp Thr
620                 625                 630                 635 ctc tag c                                                            1930
Leu

<210> SEQ ID NO 4
<211> LENGTH: 636
<212> TYPE: PRT
<213> ORGANISM: Homo sapiens

<400> SEQUENCE: 4

Met Ala Ala Glu Glu Ala Ala Ala Gly Gly Lys Val Leu Arg Glu
1               5                   10                  15

Glu Asn Gln Cys Ile Ala Pro Val Val Ser Ser Arg Val Ser Pro Gly
            20                  25                  30

Thr Arg Pro Thr Ala Met Gly Ser Phe Ser Ser His Met Thr Glu Phe
        35                  40                  45

Pro Arg Lys Arg Lys Gly Ser Asp Ser Asp Pro Ser Gln Ser Gly Ile
    50                  55                  60

Met Thr Glu Lys Val Val Glu Lys Leu Ser Gln Asn Pro Leu Thr Tyr
65                  70                  75                  80

Leu Leu Ser Thr Arg Ile Glu Ile Ser Ala Ser Ser Gly Ser Arg Val
                85                  90                  95

Glu Asp Gly Glu His Gln Val Lys Met Lys Ala Phe Arg Glu Ala His
            100                 105                 110

Ser Gln Thr Glu Lys Arg Arg Arg Asp Lys Met Asn Asn Leu Ile Glu
        115                 120                 125

Glu Leu Ser Ala Met Ile Pro Gln Cys Asn Pro Met Ala Arg Lys Leu
    130                 135                 140

Asp Lys Leu Thr Val Leu Arg Met Ala Val Gln His Leu Arg Ser Leu
145                 150                 155                 160
```

```
Lys Gly Leu Thr Asn Ser Tyr Val Gly Ser Asn Tyr Arg Pro Ser Phe
            165                 170                 175

Leu Gln Asp Asn Glu Leu Arg His Leu Ile Leu Lys Thr Ala Glu Gly
            180                 185                 190

Phe Leu Phe Val Val Gly Cys Glu Arg Gly Lys Ile Leu Phe Val Ser
            195                 200                 205

Lys Ser Val Ser Lys Ile Leu Asn Tyr Asp Gln Ala Ser Leu Thr Gly
            210                 215                 220

Gln Ser Leu Phe Asp Phe Leu His Pro Lys Asp Val Ala Lys Val Lys
225                 230                 235                 240

Glu Gln Leu Ser Ser Phe Asp Ile Ser Pro Arg Glu Lys Leu Ile Asp
                    245                 250                 255

Ala Lys Thr Gly Leu Gln Val His Ser Asn Leu His Ala Gly Arg Thr
            260                 265                 270

Arg Val Tyr Ser Gly Ser Arg Arg Ser Phe Phe Cys Arg Ile Lys Ser
            275                 280                 285

Cys Lys Ile Ser Val Lys Glu Glu His Gly Cys Leu Pro Asn Ser Lys
            290                 295                 300

Lys Lys Glu His Arg Lys Phe Tyr Thr Ile His Cys Thr Gly Tyr Leu
305                 310                 315                 320

Arg Ser Trp Pro Pro Asn Ile Val Gly Met Glu Glu Arg Asn Ser
                    325                 330                 335

Lys Lys Asp Asn Ser Asn Phe Thr Cys Leu Val Ala Ile Gly Arg Leu
            340                 345                 350

Gln Pro Tyr Ile Val Pro Gln Asn Ser Gly Glu Ile Asn Val Lys Pro
            355                 360                 365

Thr Glu Phe Ile Thr Arg Phe Ala Val Asn Gly Lys Phe Val Tyr Val
            370                 375                 380

Asp Gln Arg Ala Thr Ala Ile Leu Gly Tyr Leu Pro Gln Glu Leu Leu
385                 390                 395                 400

Gly Thr Ser Cys Tyr Glu Tyr Phe His Gln Asp Asp His Asn Asn Leu
                    405                 410                 415

Thr Asp Lys His Lys Ala Val Leu Gln Ser Lys Glu Lys Ile Leu Thr
            420                 425                 430

Asp Ser Tyr Lys Phe Arg Ala Lys Asp Gly Ser Phe Val Thr Leu Lys
            435                 440                 445

Ser Gln Trp Phe Ser Phe Thr Asn Pro Trp Thr Lys Glu Leu Glu Tyr
            450                 455                 460

Ile Val Ser Val Asn Thr Leu Val Leu Gly His Ser Glu Pro Gly Glu
465                 470                 475                 480

Ala Ser Phe Leu Pro Cys Ser Ser Gln Ser Ser Glu Glu Ser Ser Arg
                    485                 490                 495

Gln Ser Cys Met Ser Val Pro Gly Met Ser Thr Gly Thr Val Leu Gly
            500                 505                 510

Ala Gly Ser Ile Gly Thr Asp Ile Ala Asn Glu Ile Leu Asp Leu Gln
            515                 520                 525

Arg Leu Gln Ser Ser Ser Tyr Leu Asp Asp Ser Pro Thr Gly Leu
            530                 535                 540

Met Lys Asp Thr His Thr Val Asn Cys Arg Ser Met Ser Asn Lys Glu
545                 550                 555                 560

Leu Phe Pro Pro Ser Pro Ser Glu Met Gly Glu Leu Glu Ala Thr Arg
                    565                 570                 575

Gln Asn Gln Ser Thr Val Ala Val His Ser His Glu Pro Leu Leu Ser
            580                 585                 590
```

Asp Gly Ala Gln Leu Asp Phe Asp Ala Leu Cys Asp Asn Asp Thr
            595                 600                 605

Ala Met Ala Ala Phe Met Asn Tyr Leu Glu Ala Glu Gly Gly Leu Gly
            610                 615                 620

Asp Pro Gly Asp Phe Ser Asp Ile Gln Trp Thr Leu
625                 630                 635

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
aggcaacacc agagcactga                                              20

<210> SEQ ID NO 6
<211> LENGTH: 22
<212> TYPE: DNA
<213> ORGANISM: Artificial Sequence
<220> FEATURE:
<223> OTHER INFORMATION: Synthetic DNA

<400> SEQUENCE: 6
gccaggatta caaagtgtgc ac                                           22

<210> SEQ ID NO 7
<211> LENGTH: 19
<212> TYPE: DNA
<213> ORGANISM: Artificial Sequence
<220> FEATURE:
<223> OTHER INFORMATION: Synthetic DNA

<400> SEQUENCE: 7
ggagtgacca ggcagagca                                               19

<210> SEQ ID NO 8
<211> LENGTH: 22
<212> TYPE: DNA
<213> ORGANISM: Artificial Sequence
<220> FEATURE:
<223> OTHER INFORMATION: Synthetic DNA

<400> SEQUENCE: 8
catccatggt gaggtgtctc tc                                           22

<210> SEQ ID NO 9
<211> LENGTH: 22
<212> TYPE: DNA
<213> ORGANISM: Artificial Sequence
<220> FEATURE:
<223> OTHER INFORMATION: Synthetic DNA

<400> SEQUENCE: 9
ctgtgacctt gattcaggat gc                                           22

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10
ggactttgtt catgccacag g                    21

<210> SEQ ID NO 11
<211> LENGTH: 22
<212> TYPE: DNA
<213> ORGANISM: Artificial Sequence
<220> FEATURE:
<223> OTHER INFORMATION: Synthetic DNA

<400> SEQUENCE: 11
ggtgacagag tccttgccta gc                   22

<210> SEQ ID NO 12
<211> LENGTH: 22
<212> TYPE: DNA
<213> ORGANISM: Artificial Sequence
<220> FEATURE:
<223> OTHER INFORMATION: Synthetic DNA

<400> SEQUENCE: 12
gccaggatta caaagtgtgc ac                   22

<210> SEQ ID NO 13
<211> LENGTH: 19
<212> TYPE: DNA
<213> ORGANISM: Artificial Sequence
<220> FEATURE:
<223> OTHER INFORMATION: Synthetic DNA

<400> SEQUENCE: 13
gtggctatgg gacggttgc                       19

<210> SEQ ID NO 14
<211> LENGTH: 23
<212> TYPE: DNA
<213> ORGANISM: Artificial Sequence
<220> FEATURE:
<223> OTHER INFORMATION: Synthetic DNA

<400> SEQUENCE: 14
agttatgaac tcagccggtc tca                  23

<210> SEQ ID NO 15
<211> LENGTH: 23
<212> TYPE: DNA
<213> ORGANISM: Artificial Sequence
<220> FEATURE:
<223> OTHER INFORMATION: Synthetic DNA

<400> SEQUENCE: 15
tgaagaaaag cagccttcct tag                  23

<210> SEQ ID NO 16
<211> LENGTH: 22
<212> TYPE: DNA
<213> ORGANISM: Artificial Sequence
<220> FEATURE:
<223> OTHER INFORMATION: Synthetic DNA

<400> SEQUENCE: 16
ggtaggcacg tccattaagg ag                   22

<210> SEQ ID NO 17
<211> LENGTH: 25
<212> TYPE: DNA
<213> ORGANISM: Artificial Sequence
<220> FEATURE:

<223> OTHER INFORMATION: Synthetic DNA

<400> SEQUENCE: 17
aaagccttgg gagagatagt agtgc                                  25

<210> SEQ ID NO 18
<211> LENGTH: 19
<212> TYPE: DNA
<213> ORGANISM: Artificial Sequence
<220> FEATURE:
<223> OTHER INFORMATION: Synthetic DNA

<400> SEQUENCE: 18
tgctcccact atggatggc                                         19

<210> SEQ ID NO 19
<211> LENGTH: 21
<212> TYPE: DNA
<213> ORGANISM: Artificial Sequence
<220> FEATURE:
<223> OTHER INFORMATION: Synthetic DNA

<400> SEQUENCE: 19
ggtcgttcat cctcagtcca c                                      21

<210> SEQ ID NO 20
<211> LENGTH: 25
<212> TYPE: DNA
<213> ORGANISM: Artificial Sequence
<220> FEATURE:
<223> OTHER INFORMATION: Synthetic DNA

<400> SEQUENCE: 20
tgcaggtgtg aagttttata tccag                                  25

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA

<400> SEQUENCE: 21
gcccaaagag gactcatccc                                        20

<210> SEQ ID NO 22
<211> LENGTH: 24
<212> TYPE: DNA
<213> ORGANISM: Artificial Sequence
<220> FEATURE:
<223> OTHER INFORMATION: Synthetic DNA

<400> SEQUENCE: 22
cgatcattcg acctattttt cctg                                   24

<210> SEQ ID NO 23
<211> LENGTH: 25
<212> TYPE: DNA
<213> ORGANISM: Artificial Sequence
<220> FEATURE:
<223> OTHER INFORMATION: Synthetic DNA

<400> SEQUENCE: 23
tattccctac cccacctagt tatcc                                  25

<210> SEQ ID NO 24

```
<211> LENGTH: 18
<212> TYPE: DNA
<213> ORGANISM: Artificial Sequence
<220> FEATURE:
<223> OTHER INFORMATION: Synthetic DNA

<400> SEQUENCE: 24
agggcgagtg ggaagcag                                                     18

<210> SEQ ID NO 25
<211> LENGTH: 22
<212> TYPE: DNA
<213> ORGANISM: Artificial Sequence
<220> FEATURE:
<223> OTHER INFORMATION: Synthetic DNA

<400> SEQUENCE: 25
gtctgcatcc ctgtatgtca gg                                                22

<210> SEQ ID NO 26
<211> LENGTH: 19
<212> TYPE: DNA
<213> ORGANISM: Artificial Sequence
<220> FEATURE:
<223> OTHER INFORMATION: Synthetic DNA

<400> SEQUENCE: 26
ccactaggcg gcagtgtga                                                    19

<210> SEQ ID NO 27
<211> LENGTH: 20
<212> TYPE: DNA
<213> ORGANISM: Artificial Sequence
<220> FEATURE:
<223> OTHER INFORMATION: Synthetic DNA

<400> SEQUENCE: 27
tcgttgctct gtttccctca                                                   20

<210> SEQ ID NO 28
<211> LENGTH: 24
<212> TYPE: DNA
<213> ORGANISM: Artificial Sequence
<220> FEATURE:
<223> OTHER INFORMATION: Synthetic DNA

<400> SEQUENCE: 28
atcatcccag cacagaaatt acac                                              24

<210> SEQ ID NO 29
<211> LENGTH: 19
<212> TYPE: DNA
<213> ORGANISM: Artificial Sequence
<220> FEATURE:
<223> OTHER INFORMATION: Synthetic DNA

<400> SEQUENCE: 29
tgcaccacca actgcttag                                                    19

<210> SEQ ID NO 30
<211> LENGTH: 18
<212> TYPE: DNA
<213> ORGANISM: Artificial Sequence
<220> FEATURE:
<223> OTHER INFORMATION: Synthetic DNA

<400> SEQUENCE: 30
```

|  |  |
|---|---|
| gatgcaggga tgatgttc | 18 |

<210> SEQ ID NO 31
<211> LENGTH: 25
<212> TYPE: DNA
<213> ORGANISM: Artificial Sequence
<220> FEATURE:
<223> OTHER INFORMATION: Synthetic DNA

<400> SEQUENCE: 31

|  |  |
|---|---|
| gggaggattg ttagcacgtc tgtga | 25 |

<210> SEQ ID NO 32
<211> LENGTH: 25
<212> TYPE: DNA
<213> ORGANISM: Artificial Sequence
<220> FEATURE:
<223> OTHER INFORMATION: Synthetic DNA

<400> SEQUENCE: 32

|  |  |
|---|---|
| cactgtactc ttgagcactg tattg | 25 |

<210> SEQ ID NO 33
<211> LENGTH: 1737
<212> TYPE: DNA
<213> ORGANISM: Artificial Sequence
<220> FEATURE:
<223> OTHER INFORMATION: Synthetic DNA

<400> SEQUENCE: 33

|  |  |
|---|---|
| atggagtttc caaggaaacg cagaggcaga gattcccagc cactccagtc agaattcatg | 60 |
| acagacacaa cagtggaaag tcttccccag aatccctttg cctctcttct ttcaacaaga | 120 |
| acaggagtat cggcgcccag tggcatcagg gaagctcaca gccagatgga aaagcgtcgg | 180 |
| agagacaaga tgaaccatct gattcagaaa atgtcatcta tgatccctcc acacatcccc | 240 |
| acggcccaca aactggacaa gctcagcgtc ttgaggaggg cggtgcagta cttgaggtct | 300 |
| ctgagaggca tgacagagct ttacttagga gaaaactcta aaccttcatt tattcaggat | 360 |
| aaggaactca gtcacttaat cctcaaggca gcagaaggct tcctgtttgt ggttggatgc | 420 |
| gaaagaggga aattttttta cgtttctaag tctgtctcca aaacactgcg ttatgatcag | 480 |
| gctagcttga tgggacagaa tttgtttgac ttcttacacc aaaagacgt cgccaaagta | 540 |
| aaggaacaac tttcttgtga tggttcacca agagagaaac ctatagacac caaaacctct | 600 |
| caggtttaca gtcaccccca cactgggcga ccacgcgtgc attctggctc agacgatct | 660 |
| ttcttctttta gaatgaagag ctgtaccgtc cctgtcaaag aagagcagcc atgctcgtcc | 720 |
| tgctcaaaga agaaagacca tagaaaattc cacaccgtcc attgcactgg atacttgaga | 780 |
| agctggcctc tgaatgttgt tggcatggag aaagagtcgg tggtgggaa ggacagcggt | 840 |
| cctcttacct gccttgtggc tatgggacgg ttgcatccat acattgtccc tcaaaagagt | 900 |
| ggcaagatca acgtgagacc ggctgagttc ataactcgct tcgcaatgaa cgggaaattc | 960 |
| gtctatgttg accaaagggc aacggcaatt ttaggatacc tgcctcagga actttggga | 1020 |
| acttcatgtt atgaatattt tcatcaggat gaccacagta gtttgactga caagcacaaa | 1080 |
| gcagttctgc agagtaagga gaaaatactt acagactcat acaaattcag agtgaaggat | 1140 |
| ggtgccttcg tgactctgaa gagtgagtgg ttcagcttca caaacccttg gaccaaagag | 1200 |
| ctggagtaca ttgtgtctgt caacacgttg gttttgggc gcagtgagac caggctgtct | 1260 |
| ttgcttcagt gcggcggcag cagccagtcc tcggaagact catttagaca atcctgcatc | 1320 |

| | |
|---|---|
| aatgtgcccg gcgtatccac ggggaccatc cttggtgctg ggggtattgg aacagatatt | 1380 |
| gcaaatgagg ttctgagttt acagagatta cactcttcat ccccagaaga tgcaaaccct | 1440 |
| tcagaagtga gagatgactg cagtgtaaac ggtgggagcg cctatgggcc tgcatccact | 1500 |
| agggagcttt ttgcagtgag tccttctaaa acagaggtcc tggaggctgc caggcaacac | 1560 |
| cagagcactg aacccgccca ccctcacgga ccacttccca gtgacagtgc ccagctgggt | 1620 |
| tttgatgtcc tgtgtgacag tgacagcata gacatggctg cattcatgaa ttacctcgaa | 1680 |
| gcagagggg gcctgggtga ccctggggac ttcagtgaca tccagtgggc actctag | 1737 |

<210> SEQ ID NO 34
<211> LENGTH: 1740
<212> TYPE: DNA
<213> ORGANISM: Artificial Sequence
<220> FEATURE:
<223> OTHER INFORMATION: Synthetic DNA

<400> SEQUENCE: 34

| | |
|---|---|
| atggagtttc caaggaaacg cagaggcaga gattcccagc cactccagtc agaattcatg | 60 |
| acagacacaa cagtggaaag tcttccccag aatccctttg cctctcttct ttcaacaaga | 120 |
| acaggagtat cggcgcccag tggcatcagg gaagctcaca gccagatgga aaagcgtcgg | 180 |
| agagacaaga tgaaccatct gattcagaaa ctgtcatcta tgatccctcc acacatcccc | 240 |
| acggcccaca aactggacaa gctcagcgtc ttgaggaggg cagtgcagta cttgaggtct | 300 |
| ctgagaggca tgacagagct ttacttagga gaaaactcta accttcatt tattcaggat | 360 |
| aaggaactca gtcacttaat cctcaaggca gcagaaggct tcctgtttgt ggttggatgc | 420 |
| gaaagaggga gattttttta cgtttctaag tctgtctcca aaacactgcg ttatgatcag | 480 |
| gctagcttga tgggacagaa tttgtttgac ttcttacacc aaaagacgt cgccaaagta | 540 |
| aggaacaac tttcttgtga tggttcacca agagagaaac ctatagacac caaaacctct | 600 |
| caggtttaca gtcaccccca cactgggcga ccacgcgtgc attctggctc agacgatct | 660 |
| ttcttcttta gaatgaagag ctgtaccgtc cctgtcaaag aagagcagcc atgctcgtcc | 720 |
| tgctcaaaga agaaagacca tagaaaattc cacaccgtcc attgcactgg atacttgaga | 780 |
| agctggcctc tgaatgttgt tggcatggag aaagagtcgg gtggtgggaa ggacagcggt | 840 |
| cctcttacct gccttgtggc tatgggacgg ttgcatccat acattgtccc tcaaaagagt | 900 |
| ggcaagatca acgtgagacc ggctgagttc ataactcgct tcgcaatgaa cgggaaattc | 960 |
| gtctatgttg accaaagggc aacggcaatt ttaggatacc tgcctcagga acttttggga | 1020 |
| acttcatgtt atgaatattt tcatcaggat gaccacagta gtttgactga caagcacaaa | 1080 |
| gcagttctgc agagtaagga gaaaatactt acagactcat acaaattcag agtgaaggat | 1140 |
| ggtgccttcg tgactctgaa gagtgagtgg ttcagcttca caaacccttg gaccaaagag | 1200 |
| ctggagtaca ttgtgtctgt caacacgttg gttttgggc gcagtgagac caggctgtct | 1260 |
| ttgcttcagt gcagcagcag cagccagtcc tcggaagact catttagaca atcctgcatc | 1320 |
| aatgtgcccg gcgtatccac ggggaccgtc cttggtgctg ggagtattgg aacagatatt | 1380 |
| gcaaatgagg ttctgagttt acagagatta cactcttcat ccccagaaga tgcaaaccct | 1440 |
| tcagaagaag tgagagatga ctgcagtgta acggtggga gcgccatgg gcctgcatcc | 1500 |
| actagggagc ttttgcagt gagtccttct aaaacagagg tcctggaggc tgccaggcaa | 1560 |
| caccagagca ctgaacccgc ccaccctcac ggaccacttc ccagtgacag tgcccagctg | 1620 |
| ggttttgatg tcctgtgtga cagtgacagc atagacatgg ctgcattcat gaattacctc | 1680 |

```
gaagcagagg ggggcctggg tgaccctggg gacttcagtg acatccagtg ggcactctag    1740
```

<210> SEQ ID NO 35
<211> LENGTH: 57
<212> TYPE: PRT
<213> ORGANISM: Artificial Sequence
<220> FEATURE:
<223> OTHER INFORMATION: Synthetic Peptide

<400> SEQUENCE: 35

Arg Glu Ala His Ser Gln Met Glu Lys Arg Arg Asp Lys Met Asn
1               5                   10                  15

His Leu Ile Gln Lys Leu Ser Ser Met Ile Pro Pro His Ile Pro Thr
            20                  25                  30

Ala His Lys Leu Asp Lys Leu Ser Val Leu Arg Arg Ala Val Gln Tyr
        35                  40                  45

Leu Arg Ser Leu Arg Gly Met Thr Glu
    50                  55

<210> SEQ ID NO 36
<211> LENGTH: 56
<212> TYPE: PRT
<213> ORGANISM: Artificial Sequence
<220> FEATURE:
<223> OTHER INFORMATION: Synthetic Peptide

<400> SEQUENCE: 36

Arg Glu Ala His Asn Leu Arg Glu Arg Arg Arg Arg Glu Arg Ile Asn
1               5                   10                  15

Asp Ala Phe Asp Glu Leu Arg Ser Leu Leu Pro Thr Leu Pro Pro Ser
            20                  25                  30

Lys Lys Leu Ser Lys Ala Glu Ile Leu Arg Lys Ala Val Asp Tyr Ile
        35                  40                  45

Lys Ser Leu Gln Glu Leu Leu Gln
    50                  55

<210> SEQ ID NO 37
<211> LENGTH: 504
<212> TYPE: DNA
<213> ORGANISM: Artificial Sequence
<220> FEATURE:
<223> OTHER INFORMATION: Synthetic DNA
<220> FEATURE:
<221> NAME/KEY: exon
<222> LOCATION: (87)..(188)

<400> SEQUENCE: 37

```
catctcctag atgactgtaa atgtcatcaa ggtgaagatg agattcacc actcccaggg    60 gtgaccggag acctcctttc ttccag gtc aga att cat gac aga cac aac agt   113
                              Val Arg Ile His Asp Arg His Asn Ser
                                1               5 gga aag tct tcc cca gaa tcc ctt tgc ctc tct tct ttc aac aag aac    161
Gly Lys Ser Ser Pro Glu Ser Leu Cys Leu Ser Ser Phe Asn Lys Asn
 10              15                  20                  25 agg agt atc ggc gcc cag tgg cat cag gtaagtttcc ctgctgatct           208
Arg Ser Ile Gly Ala Gln Trp His Gln
                30 ccctgccatg aagaggctg ctcctcagag tttcgccctg gccagttct cctctgctcc    268 caccatttta tgtgatttct cagactgtag ttcttgccaa atgctggatg tttgtgatat   328 ctcacccagg gtgagaaagg cagtccaggg acgtatgagc attttgtgc ccatagcccc    388 agacttttttt taatacttgt aaagaagatc ccatgagaat ggccactttc ttgtggtcct  448
```

```
attggctttg ggtagatagc tgatcctctc aaagagatgg tgaccagatt cctgtg        504
```

<210> SEQ ID NO 38
<211> LENGTH: 504
<212> TYPE: DNA
<213> ORGANISM: Artificial Sequence
<220> FEATURE:
<223> OTHER INFORMATION: Synthetic DNA
<220> FEATURE:
<221> NAME/KEY: exon
<222> LOCATION: (86)..(188)

<400> SEQUENCE: 38

```
catctcctag atgactgtaa atgtcatcaa ggtgaagatg gagattcacc actcccaggg    60
gtgaccggag acctcctttc ttcca ggt cag aat tca tga cag aca caa cag    112
                              Gly Gln Asn Ser     Gln Thr Gln Gln
                              1                5 tgg aaa gtc ttc ccc aga atc cct ttg cct ctc ttc ttt caa caa gaa    160
Trp Lys Val Phe Pro Arg Ile Pro Leu Pro Leu Phe Phe Gln Gln Glu
     10                  15                  20 cag gag tat cgg cgc cca gtg gca tca g gtaagtttcc ctgctgatct         208
Gln Glu Tyr Arg Arg Pro Val Ala Ser
25                  30 ccctgccatg gaagaggctg ctcctcagag ttttgccctg cccagttct cctctgctcc    268 caccatttta tgtgatttct cagactgtag ttcttgccaa atgctggatg tttgtgatat    328
ctcacccagg gtgagaaagg cagtccaggg acgtatgagc attttttgtgc ccatagcccc  388 agactttttt taatacttgt aaagaagatc ccatgagaat gaccactttc ttgtggtcct   448
attggctttg ggtagatagc tgatcctctc aaaaagatgg tgaccagatt cctgtg        504
```

<210> SEQ ID NO 39
<211> LENGTH: 332
<212> TYPE: DNA
<213> ORGANISM: Artificial Sequence
<220> FEATURE:
<223> OTHER INFORMATION: Synthetic DNA

<400> SEQUENCE: 39

```
gcacacacag gcatgcactt ggtacataga cattcacttg gatgaacaca acacacataa    60
aataaacata gttttttaaaa gttaaagaaa taatgatcta accagttttt aattttttgtt  120 tgagacaggt tttactatgt agcctttgct ggtctgtagc tccttatgta gaccaggctg    180
gctttgaact cactccctga aggaagtctt aagataaatt gcaagtgttt taaattgttg    240
agtgtggtga tccatgcctg caactccaac actctaaagt ttgagccccc cacccccag    300 acctacactc tctcctcgaa aacaaaacac tg                                 332
```

<210> SEQ ID NO 40
<211> LENGTH: 332
<212> TYPE: DNA
<213> ORGANISM: Artificial Sequence
<220> FEATURE:
<223> OTHER INFORMATION: Synthetic DNA

<400> SEQUENCE: 40

```
gcacacacag gcatgcactt ggtacataga cattcacttg gatgaacaca acacacataa    60
aataaacgta gttttttaaaa gttaaagaaa taatgatcta accagttttt aattttttgtt  120 tgagacaggt tttactatgt agcctttgct ggtctgtagc tccttatgta gaccaggctg    180
gctttgaact cactccctga aggaagtctt aagataaatt gcaagtgttt taaattgttg    240
```

```
agtgtggtga tccatgcctg caactccaac actctaaagt ttgagccccc cacccccag     300 acctacactc tctcctcgaa aacaaaacac tg                                  332

<210> SEQ ID NO 41
<211> LENGTH: 493
<212> TYPE: DNA
<213> ORGANISM: Artificial Sequence
<220> FEATURE:
<223> OTHER INFORMATION: Synthetic DNA
<220> FEATURE:
<221> NAME/KEY: exon
<222> LOCATION: (163)..(224)

<400> SEQUENCE: 41
tgagaccact ggggcatttg ccatagatcc tgatcttagc tgaagtgaac aataaaatac    60
aaatgagtgg aaatttggca atcaaatac ttggagccaa catggatgca ttaatagatt    120
ccctgcccct cagggagtgt catgtgcttt tctgacctcc ag ggg gcg cag tga      174
                                                 Gly Ala Gln
                                                 1 gac cag gct gtc ttt gct tca gtg cgg cgg cag cag cca gtc ctc gga    222
Asp Gln Ala Val Phe Ala Ser Val Arg Arg Gln Gln Pro Val Leu Gly
    5                   10                  15 ag gtaagacgga gcttcaggtc aggcgtggta actcagatgc atcatccggt           274
aaggattcca tgaagacgtg cttttctgtc taagaatgga gaaactttcc agggaaagtt   334
agaaaacatt ttgactggac aggtccgtgc actgggctat aggaggagat aggggcagga   394
gaggtggttc agaaattccg ggcccttctt gtatacagat actgatctga gtttaatctc   454
caaaacatac atgaaggtag aaggaaagga ctgacatca                          493

<210> SEQ ID NO 42
<211> LENGTH: 493
<212> TYPE: DNA
<213> ORGANISM: Artificial Sequence
<220> FEATURE:
<223> OTHER INFORMATION: Synthetic DNA
<220> FEATURE:
<221> NAME/KEY: exon
<222> LOCATION: (163)..(224)

<400> SEQUENCE: 42
tgagaccact ggggcatttg ccacagatcc tgatcttagc tgaagtgaac aataaaatac    60
aaatgagtgg aaatttggca atcaaatac ttggagccaa cgtggatgca ttaatagatt    120
ccctgcccct cagggagtgt catgtgcttt tctgacctcc ag ggg gcg cag tga      174
                                                 Gly Ala Gln
                                                 1 gac cag gct gtc ttt gct tca gtg cag cag cag cag cca gtc ctc gga    222
Asp Gln Ala Val Phe Ala Ser Val Gln Gln Gln Gln Pro Val Leu Gly
    5                   10                  15 ag gtaagacgga gcttcaggtc aggcgtggta actcagatgc atcatccggt           274
aaggattcca tgaagacgtg cttttctgtc taagaatgga gaaactttcc agggaaagtt   334
agaaaacatt ttgactggac aggtccgtgc actgggctat aggaggagat aggggcagga   394
gaggtggttc agaaagtccg ggcccttctt gtatacagat actgatctga gtttaatctc   454
caaaacatac atgaaggtag aaggaaagga ctgacatca                          493

<210> SEQ ID NO 43
<211> LENGTH: 367
<212> TYPE: DNA
<213> ORGANISM: Artificial Sequence
<220> FEATURE:
```

<223> OTHER INFORMATION: Synthetic DNA

<400> SEQUENCE: 43

```
tcgctcactg agactctcct cccaggttct agattgcagc aaattgacat ttaaagctaa      60
gacttggggg ctggagaaat gtctcaatgg ctaagagcac tgactgttct tccgagagga     120
tctgggttca atctccagca cccacatggc agctcaccac tgtctgtacc tccaatattt     180
gacaccctca catcagacat atgtggaggc aaaacaccaa tgcagataaa ataaaataaa     240
acgctaagcc tcacccaggt ttacctcttg tatcccgggt tgggctctca catgtctgta     300
gctaaagatc acctggaact tctggttctc ccacctcatg ctggggttgc aggtgtatac     360
caccatg                                                                367
```

<210> SEQ ID NO 44
<211> LENGTH: 367
<212> TYPE: DNA
<213> ORGANISM: Artificial Sequence
<220> FEATURE:
<223> OTHER INFORMATION: Synthetic DNA

<400> SEQUENCE: 44

```
tcgctcactg agactctcct cccaggttct agattgcagc aaattgacat ttaaagctaa      60
gacttggggg ctggagaaat gtctcaatgg ctaagagcac tgactgttct tccgagagga     120
tctgggttca atctccagca cccacatggc agctcaccac tgtctgtacc tccaatattt     180
gacaccctca caccagacat atgtggaggc aaaacaccaa tgcagataaa ataaaataaa     240
acgctaagcc tcacccaggt ttacctcttg tatcccgggt tgggctctca catgtctgta     300
gctaaagatc acctggaact tctggttctc ccacctcatg ctggggttgc aggtgtatac     360
caccatg                                                                367
```

<210> SEQ ID NO 45
<211> LENGTH: 1737
<212> TYPE: DNA
<213> ORGANISM: Artificial Sequence
<220> FEATURE:
<223> OTHER INFORMATION: Synthetic DNA

<400> SEQUENCE: 45

```
atggagtttc caaggaaacg cagaggcaga gattcccagc cactccagtc agaattcatg      60
acagacacaa cagtggaaag tcttccccag aatccctttg cctctcttct ttcaacaaga     120
acaggagtat cggcgcccag tggcatcagg gaagctcaca gccagatgga aaagcgtcgg     180
agagacaaga tgaaccatct gattcagaaa atgtcatcta tgatccctcc acacatcccc     240
acggcccaca aactggacaa gctcagcgtc ttgaggaggg cggtgcagta cttgaggtct     300
ctgagaggca tgacagagct ttacttagga gaaaactcta accttcatt tattcaggat     360
aaggaactca gtcacttaat cctcaaggca gcagaaggct tcctgtttgt ggttggatgc     420
gaaagaggga gattttttta cgtttctaag tctgtctcca aaacactgcg ttatgatcag     480
gctagcttga tgggacagaa tttgtttgac ttcttacacc aaaagacgt cgccaaagta     540
aaggaacaac tttcttgtga tggttcacca agagagaaac ctatagacac caaaacctct     600
caggtttaca gtcaccccca cactgggcga ccacgcgtgc attctggctc agacgatct     660
ttcttcttta gaatgaagag ctgtaccgtc cctgtcaaag aagagcagcc atgctcgtcc     720
tgctcaaaga gaaagaccca tagaaaattc cacaccgtcc attgcactgg atacttgaga     780
agctggcctc tgaatgttgt tggcatggag aaagagtcgg gtggtgggaa ggacagcggt     840
```

```
cctcttacct gccttgtggc tatgggacgg ttgcatccat acattgtccc tcaaaagagt    900
ggcaagatca acgtgagacc ggctgagttc ataactcgct tcgcaatgaa cgggaaattc    960
gtctatgttg accaaagggc aacggcaatt ttaggatacc tgcctcagga acttttggga   1020
acttcatgtt atgaatattt tcatcaggat gaccacagta gtttgactga caagcacaaa   1080
gcagttctgc agagtaagga gaaatactt acagactcat acaaattcag agtgaaggat    1140
ggtgccttcg tgactctgaa gagtgagtgg ttcagcttca caaacccttg gaccaaagag   1200
ctggagtaca ttgtgtctgt caacacgttg gttttggggc gcagtgagac caggctgtct   1260
ttgcttcagt gcggcggcag cagccagtcc tcggaagact catttagaca atcctgcatc   1320
aatgtgcccg gcgtatccac ggggaccatc cttggtgctg ggggtattgg aacagatatt   1380
gcaaatgagg ttctgagttt acagagatta cactcttcat ccccagaaga tgcaaaccct   1440
tcagaagtga gagatgactg cagtgtaaac ggtgggagcg cctatgggcc tgcatccact   1500
agggagcttt ttgcagtgag tccttctaaa acagaggtcc tggaggctgc caggcaacac   1560
cagagcactg aacccgccca ccctcacgga ccacttccca gtgacagtgc ccagctgggt   1620
tttgatgtcc tgtgtgacag tgacagcata gacatggctg cattcatgaa ttacctcgaa   1680
gcagaggggg gcctgggtga ccctggggac ttcagtgaca tccagtgggc actctag     1737
```

<210> SEQ ID NO 46
<211> LENGTH: 1280
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (135)..(1199)

<400> SEQUENCE: 46

```
gggaggattg ttagcacgtc tgtgattatt ctgttctcat tcctgctgct gtgaaagcct     60
ctcaggttta cagtcacccc cacactgggc gaccacgcgt gcattctggc tccagacgat    120 cttttcttctt taga atg aag agc tgt acc gtc cct gtc aaa gaa gag cag     170
                Met Lys Ser Cys Thr Val Pro Val Lys Glu Glu Gln
                1               5                   10 cca tgc tcg tcc tgc tca aag aag aaa gac cat aga aaa ttc cac acc      218
Pro Cys Ser Ser Cys Ser Lys Lys Lys Asp His Arg Lys Phe His Thr
        15                  20                  25 gtc cat tgc act gga tac ttg aga agc tgg cct ctg aat gtt gtt ggc      266
Val His Cys Thr Gly Tyr Leu Arg Ser Trp Pro Leu Asn Val Val Gly
    30                  35                  40 atg gag aaa gag tcg ggt ggt ggg aag gac agc ggt cct ctt acc tgc      314
Met Glu Lys Glu Ser Gly Gly Gly Lys Asp Ser Gly Pro Leu Thr Cys
45                  50                  55                  60 ctt gtg gct atg gga cgg ttg cat cca tac att gtc cct caa aag agt      362
Leu Val Ala Met Gly Arg Leu His Pro Tyr Ile Val Pro Gln Lys Ser
                65                  70                  75 ggc aag atc aac gtg aga ccg gct gag ttc ata act cgc ttc gca atg      410
Gly Lys Ile Asn Val Arg Pro Ala Glu Phe Ile Thr Arg Phe Ala Met
            80                  85                  90 aac ggg aaa ttc gtc tat gtt gac caa agg gca acg gca att tta gga      458
Asn Gly Lys Phe Val Tyr Val Asp Gln Arg Ala Thr Ala Ile Leu Gly
        95                  100                 105 tac ctg cct cag gaa ctt ttg gga act tca tgt tat gaa tat ttt cat      506
Tyr Leu Pro Gln Glu Leu Leu Gly Thr Ser Cys Tyr Glu Tyr Phe His
    110                 115                 120 cag gat gac cac agt agt ttg act gac aag cac aaa gca gtt ctg cag      554
```

```
Gln Asp Asp His Ser Ser Leu Thr Asp Lys His Lys Ala Val Leu Gln
125                 130                 135                 140 agt aag gag aaa ata ctt aca gac tca tac aaa ttc aga gtg aag gat      602
Ser Lys Glu Lys Ile Leu Thr Asp Ser Tyr Lys Phe Arg Val Lys Asp
            145                 150                 155 ggt gcc ttc gtg act ctg aag agt gag tgg ttc agc ttc aca aac cct      650
Gly Ala Phe Val Thr Leu Lys Ser Glu Trp Phe Ser Phe Thr Asn Pro
                160                 165                 170 tgg acc aaa gag ctg gag tac att gtg tct gtc aac acg ttg gtt ttg      698
Trp Thr Lys Glu Leu Glu Tyr Ile Val Ser Val Asn Thr Leu Val Leu
            175                 180                 185 ggg cgc agt gag acc agg ctg tct ttg ctt cag tgc ggc ggc agc agc      746
Gly Arg Ser Glu Thr Arg Leu Ser Leu Leu Gln Cys Gly Gly Ser Ser
        190                 195                 200 cag tcc tcg gaa gac tca ttt aga caa tcc tgc atc aat gtg ccc ggc      794
Gln Ser Ser Glu Asp Ser Phe Arg Gln Ser Cys Ile Asn Val Pro Gly
205                 210                 215                 220 gta tcc acg ggg acc atc ctt ggt gct ggg ggt att gga aca gat att      842
Val Ser Thr Gly Thr Ile Leu Gly Ala Gly Gly Ile Gly Thr Asp Ile
                225                 230                 235 gca aat gag gtt ctg agt tta cag aga tta cac tct tca tcc cca gaa      890
Ala Asn Glu Val Leu Ser Leu Gln Arg Leu His Ser Ser Ser Pro Glu
            240                 245                 250 gat gca aac cct tca gaa gtg aga gat gac tgc agt gta aac ggt ggg      938
Asp Ala Asn Pro Ser Glu Val Arg Asp Asp Cys Ser Val Asn Gly Gly
        255                 260                 265 agc gcc tat ggg cct gca tcc act agg gag ctt ttt gca gtg agt cct      986
Ser Ala Tyr Gly Pro Ala Ser Thr Arg Glu Leu Phe Ala Val Ser Pro
270                 275                 280 tct aaa aca gag gtc ctg gag gct gcc agg caa cac cag agc act gaa     1034
Ser Lys Thr Glu Val Leu Glu Ala Ala Arg Gln His Gln Ser Thr Glu
285                 290                 295                 300 ccc gcc cac cct cac gga cca ctt ccc agt gac agt gcc cag ctg ggt     1082
Pro Ala His Pro His Gly Pro Leu Pro Ser Asp Ser Ala Gln Leu Gly
            305                 310                 315 ttt gat gtc ctg tgt gac agt gac agc ata gac atg gct gca ttc atg     1130
Phe Asp Val Leu Cys Asp Ser Asp Ser Ile Asp Met Ala Ala Phe Met
        320                 325                 330 aat tac ctc gaa gca gag ggg ggc ctg ggt gac cct ggg gac ttc agt     1178
Asn Tyr Leu Glu Ala Glu Gly Gly Leu Gly Asp Pro Gly Asp Phe Ser
335                 340                 345 gac atc cag tgg gca ctc tag cattttggct ttgtacttta acatgagaat        1229
Asp Ile Gln Trp Ala Leu
        350 catttcagag tgtttcattg acaaaacact gtactcttga gcactgtatt g            1280

<210> SEQ ID NO 47
<211> LENGTH: 354
<212> TYPE: PRT
<213> ORGANISM: Artificial Sequence
<220> FEATURE:
<223> OTHER INFORMATION: Synthetic Construct

<400> SEQUENCE: 47

Met Lys Ser Cys Thr Val Pro Val Lys Glu Glu Gln Pro Cys Ser Ser
1               5                   10                  15

Cys Ser Lys Lys Lys Asp His Arg Lys Phe His Thr Val His Cys Thr
            20                  25                  30

Gly Tyr Leu Arg Ser Trp Pro Leu Asn Val Val Gly Met Glu Lys Glu
        35                  40                  45
```

```
Ser Gly Gly Gly Lys Asp Ser Gly Pro Leu Thr Cys Leu Val Ala Met
 50                  55                  60

Gly Arg Leu His Pro Tyr Ile Val Pro Gln Lys Ser Gly Lys Ile Asn
 65                  70                  75                  80

Val Arg Pro Ala Glu Phe Ile Thr Arg Phe Ala Met Asn Gly Lys Phe
                 85                  90                  95

Val Tyr Val Asp Gln Arg Ala Thr Ala Ile Leu Gly Tyr Leu Pro Gln
                100                 105                 110

Glu Leu Leu Gly Thr Ser Cys Tyr Glu Tyr Phe His Gln Asp His
            115                 120                 125

Ser Ser Leu Thr Asp Lys His Lys Ala Val Leu Gln Ser Lys Glu Lys
130                 135                 140

Ile Leu Thr Asp Ser Tyr Lys Phe Arg Val Lys Asp Gly Ala Phe Val
145                 150                 155                 160

Thr Leu Lys Ser Glu Trp Phe Ser Phe Thr Asn Pro Trp Thr Lys Glu
                165                 170                 175

Leu Glu Tyr Ile Val Ser Val Asn Thr Leu Val Leu Gly Arg Ser Glu
                180                 185                 190

Thr Arg Leu Ser Leu Leu Gln Cys Gly Gly Ser Ser Gln Ser Ser Glu
            195                 200                 205

Asp Ser Phe Arg Gln Ser Cys Ile Asn Val Pro Gly Val Ser Thr Gly
210                 215                 220

Thr Ile Leu Gly Ala Gly Gly Ile Gly Thr Asp Ile Ala Asn Glu Val
225                 230                 235                 240

Leu Ser Leu Gln Arg Leu His Ser Ser Pro Glu Asp Ala Asn Pro
                245                 250                 255

Ser Glu Val Arg Asp Asp Cys Ser Val Asn Gly Gly Ser Ala Tyr Gly
            260                 265                 270

Pro Ala Ser Thr Arg Glu Leu Phe Ala Val Ser Pro Ser Lys Thr Glu
            275                 280                 285

Val Leu Glu Ala Ala Arg Gln His Gln Ser Thr Glu Pro Ala His Pro
290                 295                 300

His Gly Pro Leu Pro Ser Asp Ser Ala Gln Leu Gly Phe Asp Val Leu
305                 310                 315                 320

Cys Asp Ser Asp Ser Ile Asp Met Ala Ala Phe Met Asn Tyr Leu Glu
                325                 330                 335

Ala Glu Gly Gly Leu Gly Asp Pro Gly Asp Phe Ser Asp Ile Gln Trp
                340                 345                 350

Ala Leu

<210> SEQ ID NO 48
<211> LENGTH: 1283
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (135)..(1202)

<400> SEQUENCE: 48
gggaggattg ttagcacgtc tgtgattatt ctgttctcat tcctgctgct gtgaaagcct    60
ctcaggttta cagtcacccc cacactgggc gaccacgcgt gcattctggc tccagacgat   120
ctttcttctt taga atg aag agc tgt acc gtc cct gtc aaa gaa gag cag     170
              Met Lys Ser Cys Thr Val Pro Val Lys Glu Glu Gln
                1               5                   10
```

|     |     |     |     |     |     |     |     |     |     |     |     |     |     |     |     |       |
| --- | --- | --- | --- | --- | --- | --- | --- | --- | --- | --- | --- | --- | --- | --- | --- | ----- |
| cca | tgc | tcg | tcc | tgc | tca | aag | aag | aaa | gac | cat | aga | aaa | ttc | cac | acc | 218 |
| Pro | Cys | Ser | Ser | Cys | Ser | Lys | Lys | Lys | Asp | His | Arg | Lys | Phe | His | Thr | |
|     |     | 15  |     |     |     |     | 20  |     |     |     |     | 25  |     |     |     | |
| gtc | cat | tgc | act | gga | tac | ttg | aga | agc | tgg | cct | ctg | aat | gtt | gtt | ggc | 266 |
| Val | His | Cys | Thr | Gly | Tyr | Leu | Arg | Ser | Trp | Pro | Leu | Asn | Val | Val | Gly | |
|     | 30  |     |     |     | 35  |     |     |     |     | 40  |     |     |     |     |     | |
| atg | gag | aaa | gag | tcg | ggt | ggt | ggg | aag | gac | agc | ggt | cct | ctt | acc | tgc | 314 |
| Met | Glu | Lys | Glu | Ser | Gly | Gly | Gly | Lys | Asp | Ser | Gly | Pro | Leu | Thr | Cys | |
| 45  |     |     |     | 50  |     |     |     |     | 55  |     |     |     |     |     | 60  | |
| ctt | gtg | gct | atg | gga | cgg | ttg | cat | cca | tac | att | gtc | cct | caa | aag | agt | 362 |
| Leu | Val | Ala | Met | Gly | Arg | Leu | His | Pro | Tyr | Ile | Val | Pro | Gln | Lys | Ser | |
|     |     |     |     | 65  |     |     |     |     | 70  |     |     |     |     | 75  |     | |
| ggc | aag | atc | aac | gtg | aga | ccg | gct | gag | ttc | ata | act | cgc | ttc | gca | atg | 410 |
| Gly | Lys | Ile | Asn | Val | Arg | Pro | Ala | Glu | Phe | Ile | Thr | Arg | Phe | Ala | Met | |
|     |     |     | 80  |     |     |     |     | 85  |     |     |     |     | 90  |     |     | |
| aac | ggg | aaa | ttc | gtc | tat | gtt | gac | caa | agg | gca | acg | gca | att | tta | gga | 458 |
| Asn | Gly | Lys | Phe | Val | Tyr | Val | Asp | Gln | Arg | Ala | Thr | Ala | Ile | Leu | Gly | |
|     |     | 95  |     |     |     |     | 100 |     |     |     |     | 105 |     |     |     | |
| tac | ctg | cct | cag | gaa | ctt | ttg | gga | act | tca | tgt | tat | gaa | tat | ttt | cat | 506 |
| Tyr | Leu | Pro | Gln | Glu | Leu | Leu | Gly | Thr | Ser | Cys | Tyr | Glu | Tyr | Phe | His | |
|     | 110 |     |     |     |     | 115 |     |     |     |     | 120 |     |     |     |     | |
| cag | gat | gac | cac | agt | agt | ttg | act | gac | aag | cac | aaa | gca | gtt | ctg | cag | 554 |
| Gln | Asp | Asp | His | Ser | Ser | Leu | Thr | Asp | Lys | His | Lys | Ala | Val | Leu | Gln | |
| 125 |     |     |     |     | 130 |     |     |     |     | 135 |     |     |     |     | 140 | |
| agt | aag | gag | aaa | ata | ctt | aca | gac | tca | tac | aaa | ttc | aga | gtg | aag | gat | 602 |
| Ser | Lys | Glu | Lys | Ile | Leu | Thr | Asp | Ser | Tyr | Lys | Phe | Arg | Val | Lys | Asp | |
|     |     |     |     | 145 |     |     |     |     | 150 |     |     |     |     | 155 |     | |
| ggt | gcc | ttc | gtg | act | ctg | aag | agt | gag | tgg | ttc | agc | ttc | aca | aac | cct | 650 |
| Gly | Ala | Phe | Val | Thr | Leu | Lys | Ser | Glu | Trp | Phe | Ser | Phe | Thr | Asn | Pro | |
|     |     |     |     | 160 |     |     |     |     | 165 |     |     |     |     | 170 |     | |
| tgg | acc | aaa | gag | ctg | gag | tac | att | gtg | tct | gtc | aac | acg | ttg | gtt | ttg | 698 |
| Trp | Thr | Lys | Glu | Leu | Glu | Tyr | Ile | Val | Ser | Val | Asn | Thr | Leu | Val | Leu | |
|     |     | 175 |     |     |     |     | 180 |     |     |     |     | 185 |     |     |     | |
| ggg | cgc | agt | gag | acc | agg | ctg | tct | ttg | ctt | cag | tgc | agc | agc | agc | agc | 746 |
| Gly | Arg | Ser | Glu | Thr | Arg | Leu | Ser | Leu | Leu | Gln | Cys | Ser | Ser | Ser | Ser | |
|     | 190 |     |     |     |     | 195 |     |     |     |     | 200 |     |     |     |     | |
| cag | tcc | tcg | gaa | gac | tca | ttt | aga | caa | tcc | tgc | atc | aat | gtg | ccc | ggc | 794 |
| Gln | Ser | Ser | Glu | Asp | Ser | Phe | Arg | Gln | Ser | Cys | Ile | Asn | Val | Pro | Gly | |
| 205 |     |     |     |     | 210 |     |     |     |     | 215 |     |     |     |     | 220 | |
| gta | tcc | acg | ggg | acc | gtc | ctt | ggt | gct | ggg | agt | att | gga | aca | gat | att | 842 |
| Val | Ser | Thr | Gly | Thr | Val | Leu | Gly | Ala | Gly | Ser | Ile | Gly | Thr | Asp | Ile | |
|     |     |     | 225 |     |     |     |     | 230 |     |     |     |     | 235 |     |     | |
| gca | aat | gag | gtt | ctg | agt | tta | cag | aga | tta | cac | tct | tca | tcc | cca | gaa | 890 |
| Ala | Asn | Glu | Val | Leu | Ser | Leu | Gln | Arg | Leu | His | Ser | Ser | Ser | Pro | Glu | |
|     |     |     | 240 |     |     |     |     | 245 |     |     |     |     | 250 |     |     | |
| gat | gca | aac | cct | tca | gaa | gaa | gtg | aga | gat | gac | tgc | agt | gta | aac | ggt | 938 |
| Asp | Ala | Asn | Pro | Ser | Glu | Glu | Val | Arg | Asp | Asp | Cys | Ser | Val | Asn | Gly | |
|     |     | 255 |     |     |     |     | 260 |     |     |     |     | 265 |     |     |     | |
| ggg | agc | gcc | tat | ggg | cct | gca | tcc | act | agg | gag | ctt | ttt | gca | gtg | agt | 986 |
| Gly | Ser | Ala | Tyr | Gly | Pro | Ala | Ser | Thr | Arg | Glu | Leu | Phe | Ala | Val | Ser | |
|     | 270 |     |     |     |     | 275 |     |     |     |     | 280 |     |     |     |     | |
| cct | tct | aaa | aca | gag | gtc | ctg | gag | gct | gcc | agg | caa | cac | cag | agc | act | 1034 |
| Pro | Ser | Lys | Thr | Glu | Val | Leu | Glu | Ala | Ala | Arg | Gln | His | Gln | Ser | Thr | |
| 285 |     |     |     |     | 290 |     |     |     |     | 295 |     |     |     |     | 300 | |
| gaa | ccc | gcc | cac | cct | cac | gga | cca | ctt | ccc | agt | gac | agt | gcc | cag | ctg | 1082 |
| Glu | Pro | Ala | His | Pro | His | Gly | Pro | Leu | Pro | Ser | Asp | Ser | Ala | Gln | Leu | |
|     |     |     |     | 305 |     |     |     |     | 310 |     |     |     |     | 315 |     | |
| ggt | ttt | gat | gtc | ctg | tgt | gac | agt | gac | agc | ata | gac | atg | gct | gca | ttc | 1130 |
| Gly | Phe | Asp | Val | Leu | Cys | Asp | Ser | Asp | Ser | Ile | Asp | Met | Ala | Ala | Phe | |
|     |     + 320 |     |     |     |     | 325 |     |     |     |     | 330 |     |     |     | |

```
atg aat tac ctc gaa gca gag ggg ggc ctg ggt gac cct ggg gac ttc      1178
Met Asn Tyr Leu Glu Ala Glu Gly Gly Leu Gly Asp Pro Gly Asp Phe
        335                 340                 345 agt gac atc cag tgg gca ctc tag cattttggct ttgtacttta acatgagaat     1232
Ser Asp Ile Gln Trp Ala Leu
        350             355 catttcagag tgtttcattg acaaaacact gtactcttga gcactgtatt g             1283
```

<210> SEQ ID NO 49
<211> LENGTH: 355
<212> TYPE: PRT
<213> ORGANISM: Artificial Sequence
<220> FEATURE:
<223> OTHER INFORMATION: Synthetic Construct

<400> SEQUENCE: 49

```
Met Lys Ser Cys Thr Val Pro Val Lys Glu Glu Gln Pro Cys Ser Ser
1               5                   10                  15

Cys Ser Lys Lys Lys Asp His Arg Lys Phe His Thr Val His Cys Thr
            20                  25                  30

Gly Tyr Leu Arg Ser Trp Pro Leu Asn Val Val Gly Met Glu Lys Glu
        35                  40                  45

Ser Gly Gly Lys Asp Ser Gly Pro Leu Thr Cys Leu Val Ala Met
    50                  55                  60

Gly Arg Leu His Pro Tyr Ile Val Pro Gln Lys Ser Gly Lys Ile Asn
65              70                  75                  80

Val Arg Pro Ala Glu Phe Ile Thr Arg Phe Ala Met Asn Gly Lys Phe
                85                  90                  95

Val Tyr Val Asp Gln Arg Ala Thr Ala Ile Leu Gly Tyr Leu Pro Gln
            100                 105                 110

Glu Leu Leu Gly Thr Ser Cys Tyr Glu Tyr Phe His Gln Asp Asp His
        115                 120                 125

Ser Ser Leu Thr Asp Lys His Lys Ala Val Leu Gln Ser Lys Glu Lys
    130                 135                 140

Ile Leu Thr Asp Ser Tyr Lys Phe Arg Val Lys Asp Gly Ala Phe Val
145                 150                 155                 160

Thr Leu Lys Ser Glu Trp Phe Ser Phe Thr Asn Pro Trp Thr Lys Glu
                165                 170                 175

Leu Glu Tyr Ile Val Ser Val Asn Thr Leu Val Leu Gly Arg Ser Glu
            180                 185                 190

Thr Arg Leu Ser Leu Leu Gln Cys Ser Ser Ser Gln Ser Ser Glu
        195                 200                 205

Asp Ser Phe Arg Gln Ser Cys Ile Asn Val Pro Gly Val Ser Thr Gly
    210                 215                 220

Thr Val Leu Gly Ala Gly Ser Ile Gly Thr Asp Ile Ala Asn Glu Val
225                 230                 235                 240

Leu Ser Leu Gln Arg Leu His Ser Ser Pro Glu Asp Ala Asn Pro
                245                 250                 255

Ser Glu Glu Val Arg Asp Asp Cys Ser Val Asn Gly Gly Ser Ala Tyr
            260                 265                 270

Gly Pro Ala Ser Thr Arg Glu Leu Phe Ala Val Ser Pro Ser Lys Thr
        275                 280                 285

Glu Val Leu Glu Ala Ala Arg Gln His Gln Ser Thr Glu Pro Ala His
    290                 295                 300

Pro His Gly Pro Leu Pro Ser Asp Ser Ala Gln Leu Gly Phe Asp Val
305                 310                 315                 320
```

```
Leu Cys Asp Ser Asp Ser Ile Asp Met Ala Ala Phe Met Asn Tyr Leu
            325                 330                 335

Glu Ala Glu Gly Gly Leu Gly Asp Pro Gly Asp Phe Ser Asp Ile Gln
        340                 345                 350

Trp Ala Leu
        355

<210> SEQ ID NO 50
<211> LENGTH: 636
<212> TYPE: DNA
<213> ORGANISM: Artificial Sequence
<220> FEATURE:
<223> OTHER INFORMATION: Synthetic DNA
<220> FEATURE:
<221> NAME/KEY: 3'UTR
<222> LOCATION: (72)..(628)

<400> SEQUENCE: 50
cattttggct tgtacttta acatgagaat catttcagag tgtttcattg acaaaacact      60
gtactcttga gcactgtatt ggtacattta tctcttatta ctagtctact gactttata    120 atatatctgc cctttattct cactgggatg tgcggagtca cacatgctcc tccaaagaga   180
aacagccaag tttatcagtc cctctttaca cagtgagaag gcagcttggg ggtcaggctg   240
ccatattttt gctaaaatat tctgaccaaa aactgctacc aaccatattg ttagggcttt   300 ttttttttaca tttatttatt tactatatgt aagtacactg tagctgtcct cagatactcc  360
agaaaaggga atcagattc gttggggatg gttgtgtgcc accatgtggt tgctgggatt    420
tgaactcggg actttcggaa gagcagtcgg cgctcttaac cactgagcca tctcaccagc   480
ccctgttctt gttttcaaga caaggtttct ctgtgtatcc ctggctgtct tgtaactcac   540
tctgtagacc aggctggcct tgaactcaaa gatctgcctg cctcctcttc ctcccaagtg   600
ttgagattaa agccatacat cacaattccc agctta                            636

<210> SEQ ID NO 51
<211> LENGTH: 513
<212> TYPE: DNA
<213> ORGANISM: Artificial Sequence
<220> FEATURE:
<223> OTHER INFORMATION: Synthetic DNA
<220> FEATURE:
<221> NAME/KEY: 3'UTR
<222> LOCATION: (72)..(505)

<400> SEQUENCE: 51
cattttggct tgtacttta acatgagaat catttcagag tgtttcattg acaaaacact      60
gtactcttga gcactgtatt ggtacatttt tatctctta ttactagtct actgactttt    120
atatatctgc cctttattct cactgggatg tgcggagtca cacatgctcc tccaaagaga   180
aacagccaag tttatcaatc cctctttaca cagtgagaag gcagcttggg ggtcaggctg   240
ccatattttt gctaaaatat tctgaccaaa aactgctacc aaccatattg ttagggcttt   300
ttttaaatat atatatactt tgttttttga gtttgggatt tttgttttgt tctgtctgtt  360
ttctgttttt gtcttcaaga cagggtttct ctgtgtagcc ctggctgtct tgtaactcac   420
tctgtagacc aggctggcct tgaactcaaa gatccgcctg cctcttcctc ccaagtgttg   480
agattaaagc catatatcac aattcccagc tta                              513

<210> SEQ ID NO 52
<211> LENGTH: 774
<212> TYPE: DNA
<213> ORGANISM: Artificial Sequence
```

<220> FEATURE:
<223> OTHER INFORMATION: Synthetic DNA

<400> SEQUENCE: 52

```
ttactggagg gattacagat aggtgggttt ggagtcaccc ggttggagga ggaaagacag      60
gggaaggtgg aagaacggga agagaaagga agctgccatg agaggagatg gaccacaagc     120
acgtggccag gagaaacagc aagtatcccg ggtacatccc tggggaggta gccaggccag     180
cagttagaag agtagattag gggtgacctc ccagtaattt tcaaagccaa ataaaataac     240
catagtttga gtctcattta tttgtaagct agtctgggat aagcttacat tgcttgcact     300
acaagatttc ctccggttct gcagtgctca tttcttagac tttccccgac tgagaaaaca     360
gaagcgaatg ggtgggtgtt cattcatttc ggcggtggct gagggaatgg ctgggtgaca     420
gaggtaaggg cagcattgtg cagtcaggac aggataactc tgcctcgctg ctggagtgga     480
acttcgatca agctcctgtc cacgaggctt ggtctctctc tgaacaacgg tctgtctaga     540
aagccagagt ttcgggcgac ctgggtggat ctccgaccta tgcggcagag tcggtgagtt     600
ctttctgagc tgtagtttat tagctttcgg ggttttgagt ggttttttgcg tgtgatagga     660
acagcagctt gggaacccat ttgccacact gtattaacta agaaggtcca caccctcttg     720
ccctctggac ctaacaaaaa gagtgtgcga cccagtcctt ggagatccag tgac           774
```

<210> SEQ ID NO 53
<211> LENGTH: 775
<212> TYPE: DNA
<213> ORGANISM: Artificial Sequence
<220> FEATURE:
<223> OTHER INFORMATION: Synthetic DNA

<400> SEQUENCE: 53

```
ttactggagg gattacagat aggtgggttt ggagtcaccc ggttggagga ggaaagacag      60
gggaaggtgg aagaacggga agagaaagga agctgccatg agaggagatg gaccacaagc     120
acgtggccag gagaaacagc aagtatcccg ggtacatccc tggggaggta gccaggccag     180
cagttagaag agtagattag gggtgacctc ccagtaattt tcaaagccaa ataaaataac     240
catagtttga gtctcattta tttgtaagct agtcagggat aagcttacat tgcttgcact     300
acaagatttc ctccagttct gcagtgttca tttcttagac tttccccgac tgagaaaaca     360
gaagcgaatg ggtgggtgtt cattcatttc tggcggtggc tgagggaatg gctgggtgac     420
agaggtaagg gcagcattgt gcagtcagga caggataact ctgcctcgct gctggagtgg     480
aacttcgatc aagctcctgt ccacgaggct tggtctctct ctgaacaacg tctgtctag      540
aaagccagag tttcgggcga cctgggtgga tctccgacct atgcggcaga gtcggtgagt     600
tctttctgag ctgtagttta ttagctttcg gggttttgag tggttttttgc gtgtgatagg     660
aacagcagct tgggaaccca tttgccacac tgtattaact aagaaggtcc acaccctctt     720
gccctctgga cctaacaaaa agagtgtgcg acccagtcct tggagatcca gtgac          775
```

<210> SEQ ID NO 54
<211> LENGTH: 683
<212> TYPE: DNA
<213> ORGANISM: Artificial Sequence
<220> FEATURE:
<223> OTHER INFORMATION: Synthetic DNA

<400> SEQUENCE: 54

```
atttatgtgg gcagagtgag tgtaactgag gaatccccct cgcgaccgta ggatgaaggg      60
agctccggag ctccaaggag tcttggttac atatgtgcct aactgttaca ggagtccctg     120
```

```
gggcggttgt aaaaagaaaa gggtcaggac cacagaccag tctttcttgc accatgaagg    180
gtctccctgt cctccacctc ttgctttccc tcttgccttt tcagcgccac tgagggcgtt    240
cctcttggtt tagggcggat ctcaacgctg ctccgccagc ctctgcgctt ggggctctgc    300
tgaggctccg ccgtgcggg tgccttgtcc cgcccggggc tggctagggc tgccgggcct    360
gcgatgccca agccctgtgc gccagggccg aatgcaggga gccgcggggc tgcagctcca    420
ggtgagtggc ttgtcgagac cccgaaactg tgtcgggcgt ccttgacagc aagccagtac    480
cccattccaa gctgggggag gggtccccgc atgtctacac cagggtctca tctgatggct    540
gtggatcaag gcggtaggtt cgcacagccc cagcgcagtt gtatcacctc cgggacccag    600
tccggcgtgt ggggtccagt cccagctgcg tcctacagtg ggcgagctgc gggtacaatc    660
cagagtctgc atactctaca gtt                                            683
```

<210> SEQ ID NO 55
<211> LENGTH: 683
<212> TYPE: DNA
<213> ORGANISM: Artificial Sequence
<220> FEATURE:
<223> OTHER INFORMATION: Synthetic DNA

<400> SEQUENCE: 55

```
atttatgtgg gcagagtgag tgtaactgag gaatccccct cgcgaccgta ggatgaaggg     60
agctccggag ctccaaggag tcttgattac atatgtgcct aactgttaca ggagtccctg    120
gggcggttgt aaaaagaaaa gggtcaggac cacagaccag tctttcttgc accatgaagg    180
gtctccctgt cctccacctc ttgctttccc tcttgccttt tcagcgccac tgagggcgtt    240
cctcttggtt tagggcggat ctcaacgctg ctccgccagc ctctgcgctt ggggctctgc    300
tgaggctccg ccgtgcggg tgccttgtcc cgcccggggc tggctagggc tgccgggcct    360
gcgatgccca agccctgtgc gccagggccg aatgcaggga gccgcggggc tgcagctcca    420
ggtgagtggc ttgtcgagac cccgaaactg tgtcgggcgt ccttgacagc aagccagtac    480
cccattacaa gctggaggag gggtccccgc atgtctacac cagggtctca tctgatggct    540
gtggatcaag gcggtaggtt cgcacagccc cagcgcagtt gtatcacctc cgggacccag    600
tccggcgtgt ggggtccagt cccagctgcg tcctacagtg ggcgagctgc gggtacaatc    660
cagagtctgc atactctaca gtt                                            683
```

<210> SEQ ID NO 56
<211> LENGTH: 867
<212> TYPE: DNA
<213> ORGANISM: Artificial Sequence
<220> FEATURE:
<223> OTHER INFORMATION: Synthetic DNA

<400> SEQUENCE: 56

```
tccagagtct gcatactcta cagtttgctc ctctctggaa gaagcaccag gatccagggt     60
gctgctggag gcctcgttgt gctgcgttcc aatggccaag tccaggcctg gggagtgcag    120
aggcgcgcgc aagcaccctc ttatcacggt ctctctgggc ttgtggtggg aatggggaag    180
caaacctctt atcttccggg gctgggtatt gaacccagga ctccaggcta gtactgtaat    240
ctctgctcct tcatttttgt gagtcaagtt gggagttttg cctcacctgt cctttctgtt    300
gctctcagtg ataaactggg aggtgtctcc ctgggaacat ggtgaccatt atttcacaga    360
ggataatcat aaaaagctgt tatttatggc aggcggaagt caggaagaaa agaacacacc    420
aataaataaa agcaggcatg gaagtcaagg tcacagttat tttgattaac agactagctg    480
```

```
gctgactgag attgatgctt gattgattgg ttgattgatt ggttgattgg ttgattgatt    540
gattaattga ttgattgatg tgtagccttt ggctagcctg taacttgctg taccaccaac    600
ttaacctgga cttgcatctg aagagctggc tacaggtttg tctcatcttt ctggtgtaac    660
tttaatcaat gatggggaaa tttctgtctg tgacctttca agggttcctg tggtctccct    720
gcctgcatgg tgctcaaatc cattttgcta aaaagaaggt cccttcttgc tctaagctct    780
gcttcactct cttctgggtg cctcagtttc ctccctgtaa tatgggggta atgactacat    840
aggtctctgc attctgcaac tgtaagg                                         867

<210> SEQ ID NO 57
<211> LENGTH: 867
<212> TYPE: DNA
<213> ORGANISM: Artificial Sequence
<220> FEATURE:
<223> OTHER INFORMATION: Synthetic DNA

<400> SEQUENCE: 57
tccagagtct gcatactcta cagtttgctc ctctctggaa gaagcaccag gatccagggt     60
gctgctggag gcctcgttgt gctgcgttcc aatggccaag tccaggcctg gggagtgcag    120
aggcgcgcgc aagcaccctc ttatcacggt ctctctgggc ttgtggtggg agtggggaag    180
caaacctctt atcttccggg gctgggtatt gaacccagga ctccaggcta gtactgtaat    240
ctctgctcct ttcattttgt gagtcaagtt gggagttttg cctcacctgt cctttctgtt    300
gctctcagtg ataaactggg aggtgtctcc ctgggaacat ggtgaccatt atttcacaga    360
ggataatcat aaaaagctgt tatttatggc aggcggaagt caggaagaaa agaacacacc    420
aataaataaa agcaggcatg gaagtcaagg tcacagttat tttgattaac agactagctg    480
gctgactgag attgatgctt gattgattgg ttgattgatt ggttgattgg ttgattgatt    540
gattaattga ttgattgatg tgtagccttt ggctagcctg taacttgctg taccaccaac    600
ttaacctgga cttgcatctg aagagctggc tacaggtttg tctcatcttt ctggtgtaac    660
tttaatcaat gatggggaaa tttctgtctg tgacctttca agggttcctg tggtctccct    720
gcctgcatgg tgctcaaatc cattttgcta aaaagaaggt cccttcttgc tctaagctct    780
gcttcactct cttctgggtg cctcagtttc ctccctgtaa gatggggggta atgactacat    840 aggtctctgc attctgcaac tgtaagg                                         867

<210> SEQ ID NO 58
<211> LENGTH: 577
<212> TYPE: DNA
<213> ORGANISM: Artificial Sequence
<220> FEATURE:
<223> OTHER INFORMATION: Synthetic DNA

<400> SEQUENCE: 58
acacacacac acacacacac actaggtggg gccaaacata actgcctgct cagttaacat     60
tttatgagag cagcttatgg attagacact gatgctgagc ctgctgccct gcccagcagt    120
tgagcatcct cttggaagac ggtcccagaa cccttggagc tagagggagg acccttccag    180
aaagccacac actggccaga atcgcctgca gggcagctt ctttaatagc atctcacctc    240
ctccccttct cagctgctca tctcttctgt gatgttactg gacctagctc ttttgagttg    300
tcgtttttgc aacggtggtg gcttaaattc atgctcctga ctcagaaggc atcccaatct    360
gctttgcata aactgttgtt cctggcctgt gtgtcctagg cagttccttc caggagtgca    420
tcacacaagc taatccagga tgggcttggg ccctgacttg ctctggtgtg gggatcgagt    480
```

-continued

```
tcattagtca gcccagaacc ctctcgacat tatcagggac tcagtgttgg cctataaggc    540
ccaaaggaag ctgagccatc tgcctgccct gaaggtt                              577

<210> SEQ ID NO 59
<211> LENGTH: 577
<212> TYPE: DNA
<213> ORGANISM: Artificial Sequence
<220> FEATURE:
<223> OTHER INFORMATION: Synthetic DNA

<400> SEQUENCE: 59
acacacacac acacacacac acaaggtggg gccaaacata actgcctgct cagttaacat     60
tttatgagag cagcttatgg attagacact gatgctgagc ctgctgccct gcccagcagt    120
tgagcatcct cttggaagac ggtcccagaa cccttggagc tagagggagg acccttccag    180
aaagctacac agtggccaga agcgcctgca ggggcagctt ctttaacagc atctcacctc    240 ctcccttct cagctgctca tctcttctgt gatgttattg gacctagctc ttttgagttg     300 tcgttttgc aacggtggtg gcttaaattc atgctcctga ctcagaaggc atcccaatct    360
gctttgcata aactgttgtt cctggcctgt gtgtcctagg cagttccttc caggagtgca    420
tcacacaagc taatccagga tgggcttggg ccctgacttg ctctggtgtg gggatcgagt    480
tcattagtca gcccagaacc ctctcgacat tatcagggac tcagtgttgg cctataaggc    540
ccaaaggaag ctgagccatc tgcctgccct gaaggtt                              577

<210> SEQ ID NO 60
<211> LENGTH: 15
<212> TYPE: PRT
<213> ORGANISM: Artificial Sequence
<220> FEATURE:
<223> OTHER INFORMATION: Synthetic Construct

<400> SEQUENCE: 60

Arg Asp Lys Met Asn His Leu Ile Gln Lys Leu Ser Ser Met Ile
1               5                   10                  15

<210> SEQ ID NO 61
<211> LENGTH: 434
<212> TYPE: DNA
<213> ORGANISM: Artificial Sequence
<220> FEATURE:
<223> OTHER INFORMATION: Synthetic DNA

<400> SEQUENCE: 61
cactgtattg gtacattttt tatctcttat tactagtcta ctgactttta tatatctgcc     60
ctttattctc actgggatgt gcggagtcac acatgctcct ccaaagagaa acagccaagt    120
ttatcaatcc ctctttacac agtgagaagg cagcttgggg gtcaggctgc catattttg    180 ctaaaatatt ctgaccaaaa actgctacca accatattgt tagggctttt tttaaatata    240
tatatacttt tgttttttgag tttgggattt ttgttttgtt ctgtctgttt tctgttttg    300 tcttcaagac agggtttctc tgtgtagccc tggctgtctt gtaactcact ctgtagacca    360
ggctggcctt gaactcaaag atccgcctgc ctcttcctcc caagtgttga gattaaagcc    420
atatatcaca attc                                                      434

<210> SEQ ID NO 62
<211> LENGTH: 557
<212> TYPE: DNA
<213> ORGANISM: Artificial Sequence
<220> FEATURE:
```

```
<223> OTHER INFORMATION: Synthetic DNA

<400> SEQUENCE: 62
cactgtattg gtacatttat ctcttattac tagtctactg acttttataa tatatctgcc      60
ctttattctc actgggatgt gcggagtcac acatgctcct ccaaagagaa acagccaagt     120
ttatcagtcc ctctttacac agtgagaagg cagcttgggg gtcaggctgc catatttttg     180
ctaaaatatt ctgaccaaaa actgctacca accatattgt tagggctttt tttttttacat   240 ttatttattt actatatgta agtacactgt agctgtcctc agatactcca gaaaagggaa    300
tcagatttcg ttggggatgg ttgtgtgcca ccatgtggtt gctgggattt gaactcggga    360
ctttcggaag agcagtcggc gctcttaacc actgagccat ctcaccagcc cctgttcttg    420
ttttcaagac aaggtttctc tgtgtatccc tggctgtctt gtaactcact ctgtagacca    480
ggctggcctt gaactcaaag atctgcctgc ctcctcttcc tcccaagtgt tgagattaaa    540
gccatacatc acaattc                                                   557
```